US006303772B1

(12) United States Patent
Sherr et al.

(10) Patent No.: US 6,303,772 B1
(45) Date of Patent: Oct. 16, 2001

(54) CYCLIN D BINDING FACTOR, AND USES THEREOF

(75) Inventors: Charles J. Sherr, Memphis, TN (US); Hiroshi Hirai, Ibaraki (JP); Sara M. Bodner, New Haven, CT (US); Kazushi Inoue, Memphis, TN (US)

(73) Assignee: St. Jude Children's Research Hospital, Memphis, TN (US)

(*) Notice: Subject to any disclaimer, the term of this patent is extended or adjusted under 35 U.S.C. 154(b) by 0 days.

(21) Appl. No.: 09/280,590

(22) Filed: Mar. 29, 1999

Related U.S. Application Data

(63) Continuation-in-part of application No. 08/928,941, filed on Sep. 12, 1997, now Pat. No. 6,180,763, which is a continuation-in-part of application No. 08/857,011, filed on May 15, 1997, now abandoned.

(60) Provisional application No. 60/017,815, filed on May 16, 1996.

(51) Int. Cl.[7] .............................. C07K 1/22; C07K 14/39; C07K 14/435; C07K 16/14

(52) U.S. Cl. ....................... 536/23.7; 536/23.1; 536/24.5; 530/350; 530/413; 435/69.1; 435/6; 435/69.7; 435/320.1

(58) Field of Search ......................... 530/350; 424/185.1; 435/320.1, 455, 6, 91.1; 536/23.1, 23.7, 24.5

(56) References Cited

U.S. PATENT DOCUMENTS 5,635,601 * 6/1997 Moyle et al. ..................... 530/388.2

FOREIGN PATENT DOCUMENTS

9743415 * 11/1997 (WO) ............................ C12N/15/12

OTHER PUBLICATIONS

Inoue et al., "Induction of ARF tumor suppressor gene expression and cell cycle arrest by transcription factor DMP1", Proc. Natl. Acad. Science, vol. 96 (7), pp. 3993–3998, 1999.*

Andrews et al. 1991. Nuc Acids Res 19:2499–2510.

Anton et al. 1988. Tryptophans in myb proteins. Nature 336:719.

Baldin et al. 1993. Genes & Devel 7:812–821.

Biedenkapp et al. 1988. Nature 335:835–837.

Davis et al. 1996. Gene 171:265–9.

Ewen et al. 1993. Cell 73:487–497.

Gabrielson et al. 1991. Science 253:1140–1143.

Gonda et al. 1985. ENBO J 4:2003–2008.

Kato et al. 1993. Genes & Devel 7:331–342.

Klempnauer et al. 1982. Cell 31:453–463.

Klempnauer et al. 1987. EMBO J 6:2719–2725.

Macleod et al. 1992. The ets gene family. Trends Biochem Sci 17:251–256.

Matsushime et al. 1992.Cell 71:323–334.

Matsushime et al. 1994. Mol Cell Biol 14:2066–2076.

Matsushime et al. 1991. Cell 65:701–713.

Matsushime et al. 1991. In Anonymous, The Cell Cycle. Cold Spring Harbor Symp Quant Biol, Cold Spring Harbor, NY, p. 69–74.

Meyerson et al. 1994. Mol Cell Biol 14:2077–2086.

Nakagoshi et al. 1990. J. Biol Chem 265:3479–3483.

Ness et al. 1989. Cell 59:1115–1125.

Ogata et al. 1994. Cell 79:639–648.

Rosson et al. 1986. Nature 319:604–606.

Tice–Baldwin et al. 1989. Science 246:931–935.

Wasylyk et al. 1993. Eur J Biochem 211:7–18.

Weston et al. 1989. Cell 58:85–93.

Hirai et al. (1996) Mol. Cell. Biol. 16:6457–67.

Robinson et al. (1996) Oncogene 12:1855–64.

Sala et al. (1992) Proc. Natl. Acad. Sci. USA 89:10415–9.

Sherr, C.J. (1996) Science 274:1672–7.

Bates et al., (1998) Nature 395:124–5.

De Stanchina et al., (1998) Genes Dev. 12:2434–42.

Evan et al., (1992) Cell 69:119–28.

Kamijo et al., (1997) Cell 91:649–59.

Quell et al., (1995) Cell 83:993–1000.

Zindy et al., (1998) Genes Dev. 12:2424–33.

Grasser et al., 1991, Mol. Cell. Biol. 11/8, pp. 3987–3996.

Database Swiss Prot on STN, Accession No. PO1103, Apr. 1, 1988.

* cited by examiner

*Primary Examiner*—Karen Cochrane Carlson
*Assistant Examiner*—Patricia Robinson
(74) *Attorney, Agent, or Firm*—Klauber & Jackson

(57) ABSTRACT

The invention discloses a direct interaction between D-type cyclins and a novel myb-like transcription factor, DMP1, which specifically interacts with cyclin D2. The present invention also provides evidence that D-type cyclins regulate gene expression in an RB-independent manner. Also included is DMP1, the transcription factor composed of a central DNA-binding domain containing three atypical myb repeats flanked by highly acidic segments located at its amino- and carboxyterminal ends. The invention includes amino acid sequences coding for DMP1, and DNA and RNA nucleotide sequences that encode the amino acid sequences. A use of DMP1 as a transcription factor is disclosed due to its specificity in binding to oligonucleotides containing the nonamer consensus sequence CCCG(G/T)ATGT. In this aspect of the invention, DMP1 when transfected into mammalian cells, activates the transcription of a reporter gene driven by a minimal promoter containing concatamerized DMP1 binding sites.

45 Claims, 23 Drawing Sheets

FIG.1A

| | | | |
|---|---|---|---|
| MSTVEEDSDT | VTVETVNSVT | FTQDTDGNLI | 30 |
| LHCPQNDPDE | VDSEDSTEPP | HKRLCLSSED | 60 |
| DQSIDDATPC | ISVVALPLSE | NDQSFEVTMT | 90 |
| ATTEVADDEL | SEGTVTQIQI | LQNDQLDEIS | 120 |
| PLGTEEVSAV | SQAWFTTKED | KDSLTNKGHK | 150 |
| WKQGMWSKEE | IDILMNNIER | YLKARGIKDA | 180 |
| TEIIFEMSKD | ERKDFYRTIA | WGLNRPLFAV | 210 |
| YRRVLRMYDD | RNHVGKYTPE | EIEKLKELRI | 240 |
| KHGNDWATIG | AALGRSASSV | KDRCRLMKDT | 270 |
| CNTGKWTEEE | EKRLAEVVHE | LTSTEPGDIV | 300 |
| TQGVSWAAVA | ERVGTRSEKQ | CRSKWLNYLN | 330 |
| WKQSGGTEWT | KEDEINLILR | IAELDVADEN | 360 |
| DINWDLLAEG | WSSVRSPQWL | RSKWWTIKRQ | 390 |
| IANHKDVSFP | VLIKGLKQLH | ENQKNNPVLL | 420 |
| ENKSGSGVPN | SNCNSSVQHV | QIRVARLEDN | 450 |
| TAISPSPMAA | LQIPVQITHV | SSTDSPAASA | 480 |
| DSETITLNSG | TLQTFEILPS | FPLQPTGTPG | 510 |
| TYLLQTSSSQ | GLPLTLTTNP | TLTLAAAAPA | 540 |
| SPEQIIVHAL | SPEHLLNTSD | NVTVQCHTPR | 570 |
| VIIQTVATED | ITSSLSQEEL | TVDSDLHSSD | 600 |
| FPEPPDALEA | DTFPDEIPRP | KMTIQPSFNN | 630 |
| AHVSKFSDQN | STELMNSVMV | RTEEEIADTD | 660 |
| LKQEEPPSDL | ASAYVTEDLE | SPTIVHQVHQ | 690 |
| TIDDETILIV | PSPHGFIQAS | DVIDTESVLP | 720 |
| LTTLTDPIFQ | HHQEASNIIG | SSLGSPVSED | 750 |
| SKDVEDLVNC | H | | 761 |

FIG.1B

```
DMP1   VGK--YTPEEIEKLKELRIKHGN-DWATIGAALGRSASSVKDRCRLMKDTCNT  273
        ||   | || |||| |     | ||  |   |        |    |  |
C-MYB  LGKTRWTREEDEKLKKLVEQNGTDDWKVIANYLPNRTD-VQCQHRWQKVLNPE   89

                           11AA                   ****  * *
DMP1   ---GKWTEEEEKRLAEVVHEL^GVSWAAVAERVGTRSEKQCRSKWLNYLNWKQ  333
          | ||||| |    |         |   |     |  ||||  |  | ||
C-MYB  LIKGPWTKEEDQRVIKLVQKYGPKRWSVIAKHLKGRIGKQCRERWHNHLNPE  141

                               6AA
DMP1   SGGTEWTKEDEINLILRIAELDVA^WDLLAEGWSSVRSPQWLRSKWWTIKRQIA  392
          | || |           |    |   |                   |    |
C-MYB  VKKTSWTEEEDRIIYQAHKRLGNR-WAEIAKLLPGRTDNAI-KNHWNSTMRRKV  193
```

FIG.5A

| | | | | | | | | | | | | | |
|---|---|---|---|---|---|---|---|---|---|---|---|---|---|
| A | 04 | 11 | 00 | 03 | 01 | 00 | 00 | 27 | 00 | 02 | 01 | 11 | 10 |
| G | 09 | 06 | 04 | 02 | 02 | 27 | 20 | 00 | 00 | 23 | 04 | 07 | 12 |
| C | 01 | 06 | 21 | 22 | 24 | 00 | 00 | 00 | 00 | 01 | 02 | 03 | 03 |
| T | 13 | 04 | 02 | 00 | 00 | 00 | 07 | 00 | 27 | 01 | 20 | 06 | 02 |
| CONSENSUS: | | | C | C | C | G | G/T | A | T | G | T | | |
| PERCENT: | | | 78 | 81 | 89 | 100 | | 100 | 100 | 85 | 74 | | |

FIG.5B

| | FLANK | CONSENSUS | FLANK | PREDICTED BINDING: |
|---|---|---|---|---|
| BS1 | AATTGA | CCCGGATGT | AGGTACGC | DMP1 AND ETS |
| BS2 | | CCCGTATGT | | DMP1 ONLY |
| M1 | | CCCTGCGGT | | NONE |
| M2 | | TTTGGATGT | | |
| M3 | | CCCGGAAGT | | ETS ONLY |
| M4 | | CCAGGATGT | | ETS |

ANTISERUM

FIG. 11A

```
                .         .         .         .         .
  1 MSTVEEDSDTVTVETVNSVTLTQDTEGNLILHCPQNEADEIDSEDSIEPP  50
    |||||||||||||||||||| ||||:||||||||||: ||:||||| |||
  1 MSTVEEDSDTVTVETVNSVTFTQDTDGNLILHCPQNDPDEVDSEDSTEPP  50
                .         .         .         .         .
 51 HKRLCLSSEDDQSIDDSTPCISVVALPLSENDQSFEVTMTATTEVADDEV 100
    ||||||||||||||||.|||||||||||||||||||||||||||||||||.
 51 HKRLCLSSEDDQSIDDATPCISVVALPLSENDQSFEVTMTATTEVADDEL 100
                .         .         .         .         .
101 TEGTVTQIQILQNEQLDEISPLGNEEVSAVSQAWFTTKEDKDSLTNKGHK 150
    .||||||||||||:|||||||||| ||||||||||||||||||||||||||
101 SEGTVTQIQILQNDQLDEISPLGTEEVSAVSQAWFTTKEDKDSLTNKGHK 150
                .         .         .         .         .
151 WKQGMWSKEEIDILMNNIERYLKARGIKDATEIIFEMSKDERKDFYRTIA 200
    ||||||||||||||||||||||||||||||||||||||||||||||||||
151 WKQGMWSKEEIDILMNNIERYLKARGIKDATEIIFEMSKDERKDFYRTIA 200
                .         .         .         .         .
201 WGLNRPLFAVYRRVLRMYDDRNHVGKYTPEEIEKLKELRIKHGNDWATIG 250
    ||||||||||||||||||||||||||||||||||||||||||||||||||
201 WGLNRPLFAVYRRVLRMYDDRNHVGKYTPEEIEKLKELRIKHGNDWATIG 250
                .         .         .         .         .
251 AALGRSASSVKDRCRLMKDTCNTGKWTEEEEKRLAEVVHELTSTEPGDIV 300
    ||||||||||||||||||||||||||||||||||||||||||||||||||
251 AALGRSASSVKDRCRLMKDTCNTGKWTEEEEKRLAEVVHELTSTEPGDIV 300
                .         .         .         .         .
301 TQGVSWAAVAERVGTRSEKQCRSKWLNYLNWKQSGGTEWTKEDEINLILR 350
    ||||||||||||||||||||||||||||||||||||||||||||||||||
301 TQGVSWAAVAERVGTRSEKQCRSKWLNYLNWKQSGGTEWTKEDEINLILR 350
                .         .         .         .         .
351 IAELDVADENDINWDLLAEGWSSVRSPQWLRSKWWTIKRQIANHKDVSFP 400
    ||||||||||||||||||||||||||||||||||||||||||||||||||
351 IAELDVADENDINWDLLAEGWSSVRSPQWLRSKWWTIKRQIANHKDVSFP 400
```

FIG. 11B

```
401 VLIKGLKQLHENQKNNPTLLENKSGSGVPNSNTNSSVQHVQIRVARLEDN 450
    ||||||||||||||||| |||||||||||||| |||||||||||||||||
401 VLIKGLKQLHENQKNNPVLLENKSGSGVPNSNCNSSVQHVQIRVARLEDN 450

451 TAISSSPMAALQIPVQITHVSSADSP-ATVDSETITLNSGTLQTFEILPS 499
    |||| ||||||||||||||||| ||| |. ||||||||||||||||||||
451 TAISPSPMAALQIPVQITHVSSTDSPAASADSETITLNSGTLQTFEILPS 500

500 FHLQPTGTPGTYLLQTSSSQGLPLTLTASPTVTLTAAAPASPEQIIVHAL 549
    | |||||||||||||||||||||||||. ||.|| |||||||||||||||
501 FPLQPTGTPGTYLLQTSSSQGLPLTLTTNPTLTLAAAAPASPEQIIVHAL 550

550 SPEHLLNTSDNVTVQCHTPRVIIQTVATEDITSSISQAELTVDSDIQSSD 599
    ||||||||||||||||||||||||||||||||||:|| |||||||: |||
551 SPEHLLNTSDNVTVQCHTPRVIIQTVATEDITSSLSQEELTVDSDLHSSD 600

600 FPEPPDALEADTFPDEIHHPKMTVEPSFNDAHVSKFSDQNSTELMNSVMV 649
    |||||||||||||||||  ||||::||||.||||||||||||||||||||
601 FPEPPDALEADTFPDEIPRPKMTIQPSFNNAHVSKFSDQNSTELMNSVMV 650

650 RTEEEISDTDLKQEESPSDLASAYVTEGLESPTIEEQVDQTIDDETILIV 699
    ||||||.|||||||| ||||||||||| ||||||  || |||||||||||
651 RTEEEIADTDLKQEEPPSDLASAYVTEDLESPTIVHQVHQTIDDETILIV 700

700 PSPHGFIQASDVIDTESVLPLTTLTDPILQHHQEESNIIGSSLGSPVSED 749
    |||||||||||||||||||||||||||| ||||| |||||||||||||||
701 PSPHGFIQASDVIDTESVLPLTTLTDPIFQHHQEASNIIGSSLGSPVSED 750

750 SKDVEDLVNCH* 761
    ||||||||||||
751 SKDVEDLVNCH* 762
```

FIG. 13

```
                 Sp1
-300    GCTAGGGGGC  GGGCGGTGCG  CACGCGTCCC

-270    GCGGCGCTGG  CTGTCACCGC  GATGGGTGGC

                      -225→ BamHI
-240    GAGCGAAGCG  AGCGGGATCC  GGAGCGTGCC

          (-)E2F                (+)DMP1/ETS
-210    CTGCGCGGGA  GGCAGCGGGA  CCCCGGATGC

-180    GGCAGGGCCC  GCGCGCGCCT  CCCCCTGGGC

                        (+)E2F
-150    GCCTCTGGGA  AGCTTTCCCG  CGCGACTGGG

-120    GACCGCGCGC  CTTGGGAGTC  GGGGGCGCGC

            Sp1
-90     CTGAGGGCGG  AGATGGGCGT  GGAGCAAAGA

               Sp1
-60     TGGGCCGGGG  GCGGCGCGTG  GGTCTCGAGG

                                    Sp1
-30     TGCCTCAACG  CCGAAGGGGC  TGGGGGCGGC

+1      GCTTCTCACC  TCGCTTGTCA  CGGTGAGGCC

                                 ←   Met
+31     GCCGCTGAGG  GAGTACAGCA  GCGGGAGCATG
```

CYCLIN D BINDING FACTOR, AND USES THEREOF

CROSS-REFERENCE TO RELATED APPLICATIONS

The present Application is a Continuation-In-Part of U.S. Ser. No. 08/928,941 filed Sep. 12, 1997 U.S. Pat. No. 6,180,763, which is a Continuation-In-Part of U.S. Ser. No. 08/857,011 filed May 15, 1997, now abandoned, which is a non-provisional application claiming the priority of provisional U.S. Ser. No. 60/017,815 filed May 16, 1996, the disclosures of which are hereby incorporated by reference in their entireties. Applicants claim the benefits of these Applications under 35 U.S.C. §§120 and 119(e).

RESEARCH SUPPORT

The research leading to the present invention was supported in part by the National Cancer Institute grants CA 20180, CA 21765, CA-56819 and CA-71907, and by the American Lebanese Syrian Associated Charities (ALSAC) of St. Jude Children's Research Hospital. The government may have certain rights in the present invention. Support for this invention was also provided by The Howard Hughes Medical Institute and the AMERICAN LEBANESE SYRIAN ASSOCIATED CHARITIES.

FIELD OF THE INVENTION

This invention relates generally to a novel myb-like protein that interacts with cyclin D. The interaction involves the regulation of RNA transcription. The invention relates to the protein, polypeptide, including biologically active or antigenic fragments thereof, and analogs and derivatives thereof, and to methods of making and using the same, including diagnostic and therapeutic uses. The invention further includes the corresponding amino acid and nucleotide sequences.

BACKGROUND OF THE INVENTION

The cell cycle for growing cells can be divided into two periods: (1) the cell division period, when the cell divides and separates, with each daughter cell receiving identical copies of the DNA; and (2) the period of growth, known as the interphase period. For the cell cycle of eucaryotes, the cell division period is labeled the M (mitotic) period. The interphase period in eucaryotes is further divided into three successive phases: G1 (gap 1) phase, which directly follows the M period; S (synthetic) phase, which follows G1; and G2 (gap 2) phase, which follows the S phase, and immediately precedes the M period. During the two gap phases no net change in DNA occurs, though damaged DNA may be repaired. On the other hand, throughout the interphase period there is continued cellular growth and continued synthesis of other cellular components. Towards the end of the G1 phase, the cell passes a restrictive (R) point and becomes committed to duplicate its DNA. At this point, the cell is also committed to divide. During the S phase, the cell replicates DNA. The net result is that during the G2 phase, the cell contains two copies of all of the DNA present in the G1 phase. During the subsequent M period, the cells divide with each daughter cell receiving identical copies of the DNA. Each daughter cell starts the next round of the growth cycle by entering the G1 phase.

The G1 phase represents the interval in which cells respond maximally to extracellular signals, including mitogens, anti-proliferative factors, matrix adhesive substances, and intercellular contacts. Passage through the R point late in G1 phase defines the time at which cells lose their dependency on mitogenic growth factors for their subsequent passage through the cycle and, conversely, become insensitive to anti-proliferative signals induced by compounds such as transforming growth factor, cyclic AMP analogs, and rapamycin. Once past the R point, cells become committed to duplicating their DNA and undergoing mitosis, as noted above, and the programs governing these processes are largely cell autonomous.

In mammalian cells, a molecular event that temporally coincides with passage through the R point is the phosphorylation of the retinoblastoma protein (RB). In its hypophosphorylated state, RB prevents the cell from exiting the G1 phase by combining with transcription factors such as E2F to actively repress transcription from promoters containing E2F binding sites. However, hyperphosphorylation of RB late in G1 phase prevents its interaction with E2F, thus allowing E2F to activate transcription of the same target genes. As many E2F-regulated genes encode proteins that are essential for DNA synthesis, RB phosphorylation at the R point helps convert cells to a pre-replicative state that anticipates the actual G1/S transition by several hours. Cells that completely lack the RB function have a reduced dependency on mitogens but remain growth factor-dependent, indicating that cancellation of the RB function is not sufficient for passage through the R point.

Phosphorylation of RB at the R point is initially triggered by holoenzymes composed of regulatory D-type cyclin subunits and their associated cyclin-dependent kinases, CDK4 and CDK6. The D-type cyclins are induced and assembled into holoenzymes as cells enter the cycle in response to mitogenic stimulation. Acting as growth factor sensors, they are continuously synthesized as long as mitogenic stimulation continues, and are rapidly degraded after mitogens are withdrawn. In fibroblasts, inhibition of cyclin D-dependent CDK activity prior to the R point, either by microinjection or by scrape loading of antibodies directed against cyclin D1 or by expression of CDK4 and CDK6 inhibitors (INK4 proteins) prevents entry into S phase. However, such manipulations have no effect in cells lacking functional RB, implying that RB is the only substrate of the cyclin D-dependent kinases whose phosphorylation is necessary for exiting the G1 phase.

Since RB-mediated controls are not essential to the cell cycle per se it is difficult to understand why mammalian cells contain three distinct D-type cyclins (D1, D2, and D3), at least two cyclin D-dependent kinases (CDK4 and CDK6), and four INK4 proteins, all, purportedly, for the sole purpose of regulating RB phosphorylation. This apparent redundancy has been explained as a method to govern transitions through the R point in different cell types responding to a plethora of distinct extracellular signals.

Alternatively, cyclin D-dependent kinases, or the cyclins alone could also be involved in the regulation of RB-independent events, perhaps linking them temporally to cell cycle controls. One mechanism for this regulation could involve the direct interaction between a cyclin, such as a D-type cyclin, and a specific transcription factor, which would allow the cyclins to regulate gene expression in an RB-independent manner. However, up until now, no such RB-independent transcription factor has been identified.

The citation of any reference herein should not be deemed as an admission that such reference is available as prior art to the instant invention.

SUMMARY OF THE INVENTION

The present invention provides a new, cyclin D-associated transcription factor. The transcription factor is an amino acid polymer which specifically binds D-type cyclins in vitro, specifically binds a DNA nucleotide sequence, and is involved in the regulation of genes that prevent cell proliferation. In one embodiment the cyclin D-associated transcription factor is a substrate of cyclin D2-CDK4 kinase. In another embodiment, the transcription factor consists of about 760 amino acids.

More particularly, the present invention includes an amino acid polymer that has a binding affinity for one or more D-type cyclins, and one or more of the following characteristics in addition to the property described above:

(1) The relative binding affinity of the amino acid polymer for cyclin D2, as compared to that for a cyclin D2 mutant that is disrupted in an amino-terminal LEU-X-CYS-X-GLU pentapeptide, (SEQ ID NO:9) is minimally less disparate than the relative binding affinity of retinoblastoma protein for cyclin D2 as compared to that for the same cyclin D2 mutant.

(2) The amino acid polymer remains able to detectably interact with a cyclin D2 mutant, containing substitutions in the amino-terminal LEU-X-CYS-X-GLU pentapeptide, (SEQ ID NO:9) under conditions where the binding of retinoblastoma protein to that same cyclin D2 mutant is essentially undetectable.

(3) The amino acid polymer binds preferentially to a specific DNA nucleotide sequence.

(4) The amino acid polymer is a substrate of the cyclin D2-CDK4 complex.

(5) The amino acid polymer contains three atypical tandem myb repeats.

(6) D-type cyclins bind less avidly to the amino acid polymer than to retinoblastoma protein, both in vitro and in Sf9 cells.

(7) Cyclin D-CDK4-dependent phosphorylation of retinoblastoma protein proceeds to a much higher stoichiometry than the comparative phosphorylation of the amino acid polymer under standard conditions for cyclin D-CDK4 kinase reactions.

(8) Cyclin D-dependent kinases phosphorylate the amino acid polymer at an atypical recognition sequence.

(9) The amino acid polymer binds preferentially to nucleic acids containing the nonamer sequence CCCG-TATGT.

(10) Relative to the cyclin D-CDK4 complex, cyclin E-CDK2 complexes phosphorylate the amino acid polymer poorly, if at all.

(11) A catalytically-inactive CDK4 does not enter into a stable ternary complex with cyclin D and the amino acid polymer under conditions where retinoblastoma protein, cyclin D and the identical catalytically-inactive CDK4 form stable ternary complexes.

(12) Cyclin D mutants which do not bind to CDK4 still interact with the amino acid polymer at unreduced efficiency.

(13) Overexpression of the amino acid polymer can arrest the cell cycle in G1 phase preventing proliferating cells from replicating their chromosomal DNA.

(14) The activity of the amino acid polymer in arresting cell growth in G1 phase depends both upon its ability (a) to bind DNA and (b) to activate transcription, and mutants defective in either of these properties are unable to prevent cells from entering S phase.

(15) Enforced transient expression of cyclin D2 or D2-CDK4 in mammalian cells negatively regulate the ability of the amino acid polymer to transactivate reporter gene expression. p1 (16) The amino acid polymer activates transcription more readily in quiescent cells lacking cyclin D expression, than in proliferating cells containing cyclin D.

(17) Enforced expression of cyclin D-CDK4 does not influence the stability of the amino acid polymer.

(18) Enforced expression of cyclin D-CDK4 does not influence the ability of the amino acid polymer to preferentially localize to the nucleus of transfected mammalian cells. Although any person having skill in the art would know that many of the above characteristics may be determined in vitro, the present invention includes the same or analogous characteristics that are determined either in situ or in vivo.

(19) Cyclin D binding to the amino acid polymer inhibits its ability to induce cell cycle arrest.

In one aspect of the present invention the amino acid polymer binds preferentially to a DNA nucleotide sequence, termed herein the cyclin D-associated transcription factor binding site or the DMP1 binding site. In a more specific embodiment, the binding site has the core trinucleotide sequence GTA. In some embodiments the nucleotide sequence contains a nonamer consensus sequence CCCG(G/T)ATGT. In other embodiments the nucleotide sequences contain multiple concatamers of the nonamer consensus sequence. In preferred embodiments the nucleotide sequence contains the nonamer consensus sequence CCCG-TATGT.

The present invention provides an isolated amino acid polymer obtained from animal cells, produced recombinantly, or prepared by chemical synthesis. In preferred embodiments the amino acid polymer is mammalian. In a more preferred embodiment the amino acid polymer is a primate protein. In the most preferred embodiments, the amino acid polymer is human. In a specific example, the amino acid polymer is obtained from a murine cell and has the amino acid sequence of SEQ ID NO:1. In a related embodiment the amino acid polymer has an amino acid sequence of SEQ ID NO:1 having one or more conservative amino acid substitutions. In another embodiment, the amino acid polymer is obtained from a human cell and contains the amino acid sequence of SEQ ID NO:24. In a related embodiment, the amino acid polymer has an amino acid sequence of SEQ ID NO:24 having one or more conservative amino acid substitutions. In a preferred embodiment, the amino acid polymer has the amino acid sequence of SEQ ID NO:29. In a related embodiment, the amino acid polymer has an amino acid sequence of SEQ ID NO:29 having one or more conservative amino acid substitutions. In a related embodiment the isolated amino acid polymer is obtained from a human cell, is encoded on human chromosome 7 at a position which corresponds to $7_q21$, and contains about 760 amino acids including the 262 amino acids of SEQ ID NO:24.

The present invention relates to the identification and elucidation of a direct interaction between D-type cyclins and a novel myb-like transcription factor termed herein DMP1. This novel factor has been found to specifically interact with cyclin D2. This present invention also describes the regulation of gene expression by D-type cyclins, and other related methods of use, in an RB-independent manner.

As shown in the Examples, infra, DMP1 includes a central DNA-binding domain containing three atypical myb repeats flanked by highly acidic segments located at its amino- and carboxylterminal ends. The present invention includes amino acid sequences coding for DMP1, including amino acid sequences containing conservative substitutions of such amino acids.

The present invention also includes peptides containing portions of amino acid polymers of the present invention, including fragments of the amino acid polymers. One such peptide corresponds to the DNA-binding domain of the amino acid polymer of the present invention. In one specific embodiment of this type, the peptide has an amino acid sequence of SEQ ID NO:16. In another such embodiment the peptide has an amino acid sequence of SEQ ID NO:16 having one or more conservative amino acid substitutions. The present invention also includes a peptide that corresponds to the transactivation domain of the amino acid polymer of the present invention. In one specific embodiment of this type, the peptide has an amino acid sequence of SEQ ID NO:18. In another such embodiment the peptide has an amino acid sequence of SEQ ID NO:18 having one or more conservative amino acid substitutions. In yet another specific embodiment of this type, the peptide has an amino acid sequence of SEQ ID NO:20. In still another such embodiment the peptide has an amino acid sequence of SEQ ID NO:20 having one or more conservative amino acid substitutions. In yet another specific embodiment of this type, the peptide has an amino acid sequence consisting of SEQ ID NO: 18 and SEQ ID NO:20. In still another such embodiment the peptide consisting of an amino acid sequence of SEQ ID NO: 18 and SEQ ID NO:20, having one or more conservative amino acid substitutions. The present invention further includes a peptide that corresponds to the D-type cyclin binding domain of the amino acid polymer of the present invention. In one specific embodiment of this type, the peptide has an amino acid sequence of SEQ ID NO:22. In another such embodiment the peptide has an amino acid sequence of SEQ ID NO:22 having one or more conservative amino acid substitutions. DNA and RNA nucleotide sequences that encode for the amino acid polymers of the present invention, and methods of use thereof are also included.

One method of the invention includes the use of DMP1 as a transcription factor due to its specificity in binding to oligonucleotides containing the nonamer consensus sequence CCCG(G/T)ATGT. A recombinant expression vector comprising the foregoing consensus sequence operably associated with a gene for expression can be prepared. In this aspect of the invention, DMP1 activates the transcription of a heterologous gene including reporter genes driven by a minimal promoter containing concatamerized DMP1 binding sites. If necessary, the invention provides for expression of DMP1 with the foregoing expression vector in order to enhance DMP1-mediated transcription from the expression vector.

Another aspect of the present invention includes fusion proteins. All of the amino acids polymers and peptides of the present invention may contain a fusion peptide (e.g. FLAG) or protein (e.g. GST or green fluorescent protein). Such examples include GST-DMP1 or green fluorescent protein-DMP1. These fusion proteins may be used to bind directly to D-type cyclins in vitro, including radiolabeled D-type cyclins.

In addition, all of the nucleic acids of the present invention can be combined with heterologous nucleotide sequences. For example, the present invention provides a nucleic acid consisting of a nucleotide sequence encoding the amino acid sequence of SEQ ID NO:29 and a heterologous nucleotide sequence. Such a nucleic acid can encode a fusion peptide and fusion protein discussed above, for example.

In still another aspect of the invention, complexes between full-length DMP1 and D-type cyclins readily form in intact Sf9 insect cells engineered to co-express both proteins under baculovirus vector control.

A further aspect of the invention includes the use of detectable labels, such as but not limited to a protein including an enzyme, a radioactive element, a bioluminescent, a chromophore that absorbs in the ultraviolet and/or visible and/or infrared region of the electromagnetic spectrum; and a fluorophore. The present invention includes an amino acid polymer labeled with such a detectable label. The present invention also includes reporter genes encoding proteins that contain detectable labels, such as green fluorescent protein, or an $^{35}$S-labeled protein, can interact with a label such as a labeled antibody or can catalyze a reaction that gives rise to a detectable signal, such as the bioluminescence catalyzed by firefly luciferase. The present invention also includes antibodies to all of the amino acid polymers of the instant invention. The antibodies of the present invention may be either polyclonal or monoclonal. Either type of antibody can further comprise a detectable label described above. In one such embodiment, the antibody is raised against the amino acid polymer of SEQ ID NO:29, or antigenic fragment thereof.

Naturally, in addition to the transcription factor, the present invention provides nucleic acids that contain nucleotide sequences or degenerate variants thereof, which encode the amino acid polymers of the present invention. In this aspect of the invention the nucleotide sequence can contain the coding region of the DNA sequence of SEQ ID NO:2 or an RNA sequence corresponding to SEQ ID NO:3; or a DNA sequence encoding a full length human DMP1 containing the nucleic acid sequence SEQ ID NO:25 or an RNA sequence encoding a full length human DMP1 containing the nucleic acid sequence SEQ ID NO:26. In one embodiment, the nucleic acid encodes a full length human DMP1 having the amino acid sequence of SEQ ID NO:29. In a preferred embodiment, the nucleic acid has a DNA sequence containing the coding region of SEQ ID NO:28, or the RNA sequence containing the coding region of SEQ ID NO:30. In a related embodiment the nucleic acid encodes an isolated amino acid polymer which is encoded on human chromosome 7 at a position which corresponds to $7_q21$, and contains about 760 amino acids, including the 262 amino acids of SEQ ID NO:24.

In addition, the present invention also includes a nucleic acid encoding a peptide that corresponds to the DNA-binding domain of the amino acid polymer of the present invention. In one such embodiment the nucleic acid encodes a peptide having an amino acid sequence of SEQ ID NO:16, or SEQ ID NO:16 having one or more conservative amino acid substitutions. In one specific embodiment of this type, the nucleic acid sequence is SEQ ID NO:17. The present invention also includes a nucleic acid encoding a peptide that corresponds to the transactivation domain of the amino acid polymer of the present invention. In one such embodiment the nucleic acid encodes a peptide having an amino acid sequence of SEQ ID NO:18, or SEQ ID NO:18 having one or more conservative amino acid substitutions. In one specific embodiment of this type, the nucleic acid sequence is SEQ ID NO:19. In yet another specific embodiment of this type, the nucleic acid encodes a peptide having an amino acid sequence of SEQ ID NO:20, or SEQ ID NO:20 having one or more conservative amino acid substitutions. In one specific embodiment of this type, the nucleic acid sequence is SEQ ID NO:21. In yet another specific embodiment of this type, the nucleic acid encodes a peptide having an amino acid sequence consisting of SEQ ID NO: 18 and SEQ ID NO:20 or consisting of an amino acid sequence of SEQ ID NO: 18 and SEQ ID NO:20 having one or more conservative amino acid substitutions. In one specific embodiment of this type, the nucleic acid sequence consists of SEQ ID NO:19 and SEQ ID NO:21. The present invention further includes a nucleic acid encoding a peptide that corresponds to the D-type cyclin binding domain of the amino acid polymer of the present invention. In one specific embodiment of this type, the nucleic acid encodes a peptide having an amino acid sequence of SEQ ID NO:22, or SEQ ID NO:22 having one or more conservative amino acid substitutions. In one specific embodiment of this type, the nucleic acid sequence is SEQ ID NO:23.

Nucleic acids containing sequences complementary to these sequences, or nucleic acids that hybridize to any of the foregoing nucleotide sequences under standard hybridization conditions are also part of the present invention. In a preferred embodiment, the nucleic acids hybridize to the foregoing nucleotide sequences under stringent conditions.

In preferred embodiments the nucleic acid is a recombinant DNA sequence that is operatively linked to an expression control sequence.

Another aspect of the invention includes methods for detecting the presence or activity of the amino acid polymer of the invention in a biological sample that is suspected to contain the amino acid polymer. These methods include steps of contacting a biological sample with a nucleotide probe under conditions that allow binding of the nucleotide probe to the amino acid polymer to occur, and then detecting whether that binding has occurred. In a specific embodiment, the nucleotide probe contains the sequence CCCGTATGT. The detection of the binding indicates the presence or activity of the amino acid polymer in the biological sample. The nucleotide probe may be labeled with a detectable label as described above. In a preferred embodiment of this aspect of the invention the nucleotide probe has a detectable label containing the radioactive element, $^{32}P$, and the detecting step includes performance of an electrophoretic mobility shift assay. In another specific embodiment, the DMP1 binding site may be used to isolate a DMP1 amino acid polymer by specific affinity binding. More particularly, the CCCGTATGT nonanucleotide may be used to isolate a mammalian DMP1 polypeptide.

Another aspect of the present invention includes methods of activating selective transcription of a heterologous gene operably associated with a DNA sequence to which the present transcription factor binds in mammalian cells. These methods include the step of recombinantly fusing a control unit comprising the nucleotide sequence, e.g., CCCGTATGT, to a selected gene forming a controllable transcript, and transfecting a mammalian cell with the recombinant gene. In some embodiments of the invention, the endogenous transcription factor of the invention in the mammalian cell will be sufficient to activate selective transcription of the heterologous gene. In other embodiments the basal level of the amino acid polymer in the mammalian cells used will be insufficient to activate detectable transcription of the recombinant heterologous gene. In these other embodiments, the amino acid polymer of the present invention may be added to the mammalian cell, e.g., by microinjection or transfection, with an expression vector comprising the transcription factor gene into the cells, thereby activating transcription of the selected gene.

The present invention also includes the use of an oligonucleotide comprising the DMP1 binding site, e.g., the nonamer sequence CCCGTATGT, as a competitive inhibiter for blocking the activation of selective transcription by the amino acid polymer.

The present invention also includes an antisense nucleic acid against an mRNA coding for the amino acid polymer of the present invention and is therefore capable of hybridizing to the mRNA. The antisense nucleic acid may be either an RNA or a DNA, preferably containing a phosphodiester analog.

In a further aspect, the present invention provides a transgenic animal comprising the expression vector which provides for increased or "super-" expression of the cyclin D-associated transcription factor homologously recombined in a chromosome or a cyclin D-associated transcription factor that no longer binds a cyclin D, such as cyclin D1. In a related embodiment, the present invention provides a transgenic animal in which the gene encoding an amino acid polymer of the present invention, such as murine DMP1, has been disrupted so as to be unable to express a functional transcription factor. Disruption of expression can be achieved by (i) knocking out the gene; (ii) introducing a null or non-sense mutation in the gene; (iii) deleting the regulatory sequences necessary for effective transcription of the gene; and (iv) introducing a mutation into the gene that results in expression of an inactive protein, e.g., a protein which fails to bind to DNA, to the DMP1 binding site on DNA, to transactivate genes under the control of a DMP1-responsive promoter, or any combination of the foregoing.

The present invention also includes methods of identifying genes that are under the control of DMP1-responsive promoters. Such genes play an important role in cell regulation, and more particularly in hindering the proliferation of the cell.

The present invention also includes drug assays for identifying drugs that antagonize or agonize the effect of DMP1 on genes under the control of a DMP1-responsive promoter. One such method is for identifying a drug that inhibits the transactivation of a gene by DMP1 in situ, comprising cotransfecting a cell with a first expression vector containing a reporter gene under the control of a promoter responsive to DMP1, and a second expression vector encoding DMP1, or a fragment thereof capable of transactivating the promoter. A potential drug is then contacted with the cell, and the expression of the reporter gene is detected. A drug is identified when the expression of the reporter gene is decreased. In preferred embodiments of this type, the identified drug prevents the detectable expression of the reporter gene.

In one particular embodiment of this type, the second expression vector encodes an amino acid polymer having the amino acid sequence of SEQ ID NO:1, or SEQ ID NO:1 having one or more conservative amino acid substitutions. In another embodiment, the second expression vector encodes an amino acid polymer having the amino acid sequence of SEQ ID NO:29, or SEQ ID NO:29 having one or more conservative amino acid substitutions. In yet another embodiment of this type the second expression vector encodes a fragment of DMP1 having an amino acid sequence of SEQ ID NO:18, or SEQ ID NO:18 having one or more conservative amino acid substitutions. In still another embodiment, the promoter is an artificial DMP1-responsive promoter. In a preferred embodiment of this type, the artificial promoter consists of 8×BS2 (CCCGTATGT) inserted into the XhoI-SmaI sites of pGL2 (Promega) 5' to a minimal simian virus 40 (SV40) early promoter driving the reporter gene. In another preferred embodiment, the reporter gene is firefly luciferase. In one embodiment, the cell is a mammalian cell, such as a mouse NIH-3T3 fibroblast. In preferred embodiments, the mammalian cell is a human cell. The potential drug may be selected by rational design, such as an analog of a cyclin, or an analog to the DNA-binding domain of DMP1, as described herein. Alternatively, the potential drug can be randomly obtained from a drug library, including from one described herein.

The present invention also includes in vitro assays to identify drugs that will bind to the cyclin binding domain of DMP1. In a preferred embodiment the cyclin binding domain has an amino acid sequence of SEQ ID NO:22, or SEQ ID NO:22 having one or more conservative amino acid substitutions. Such drugs can either inhibit DMP1 by acting as an analog of the cyclins; or alternatively, the drug can prevent the inhibition of the cyclin-dependent inhibition of DMP1 by preventing a cyclin from binding to DMP1 while not interfering with the transactivation properties of DMP1.

In one such embodiment, the method comprises placing the cyclin binding domain of DMP1 on a solid support, contacting the cyclin binding domain of DMP1 with a potential drug that is labeled, washing the solid support, and detecting the potential drug associated with the cyclin binding domain of DMP1. A potential drug is identified as a drug if it is detected with the cyclin binding domain of DMP1. The method can further comprise a step of washing the solid support with an excess of a cyclin, such as cyclin D2, prior to the detection step. In this case a potential drug is identified as a drug, if washing with cyclin hinders or prevents the detection of the labeled drug with cyclin binding domain of DMP1. Again the potential drug may be selected by rational design, such as an analog of a cyclin, or alternatively the potential drug can be randomly obtained from a drug library, including from one described herein.

An identified drug can then be assayed in situ, as described above to determine whether it enhances or diminishes the transactivation of a reporter gene under the control of a DMP1-responsive promoter. A drug is selected as an antagonist of DMP1 when the expression of the reporter gene is decreased. A drug is selected as an agonist of DMP1 when the expression of the reporter gene is increased. The method can further comprise coexpressing a cyclin, such as cyclin D2, and DMP1 in a cell and determining whether the drug prevents the inhibitory effect of the cyclin. Such a drug is selected as an agonist of DMP1, if it can hinder and/or prevent the inhibitory effect of the cyclin.

An additional embodiment includes a method of determining the effect of the drug on a CDK comprising contacting the identified drug with a CDK and performing a cyclin-CDK kinase assay on an appropriate substrate, such as retinoblastoma protein (as described herein) in the absence of a cyclin, wherein a drug is selected if the kinase assay is negative. The cyclin-CDK kinase assay is next performed with cyclin, the CDK, appropriate substrate and an excess of the drug. A drug is selected which does not interfere with the phosphorylation of the appropriate substrate by the cyclin-CDK.

Another aspect of the present invention includes a method of inducing cell cycle arrest in a eukaryotic cell without provoking cell death comprised of introducing DMP1 or an active DMP1 fragment into the cell. In this case an active DMP1 fragment acts by inducing the transcription of ARF-p19. In a particular embodiment of this type, introducing DMP1 or an active DMP1 fragment into the cell is performed by placing the DMP1 polypeptide or an active DMP1 fragment into the cell. In another embodiment, introducing DMP1 or an active DMP1 fragment into the cell is performed by placing an expression vector comprising a nucleic acid encoding the DMP1 polypeptide or an active DMP1 fragment into the cell.

The present invention further provides isolated nucleic acids comprising ARF-p19 promoters and fragments thereof. In one particular embodiment, the fragment comprises the nonamer sequence CCCGGATGC(SEQ ID NO:33). In another embodiment the ARF-p19 promoter comprises SEQ ID NO:34. In a related embodiment the ARF-p19 promoter comprises nucleotides −225 to +56 of SEQ ID NO:34. In still another embodiment the fragment comprises the nonamer sequence GACGGATGT (SEQ ID NO:35). The present invention also provides expression vectors having a transcription control sequence comprising the ARF-p19 promoters and fragments thereof operably associated with a recombinant gene or a cassette insertion site for a recombinant gene.

Yet another aspect the present invention provides methods of preventing abnormal cell growth in a eukaryotic cell. In a particular embodiment of this type, the method comprises administering an effective amount of DMP1 or an active DMP1 fragment to the cell. In this case an active DMP1 fragment acts by inducing the transcription of ARF-p19. In another embodiment, the administration of an effective amount of DMP1 or the active DMP1 fragment comprises administering a pharmaceutical composition comprising a pharmaceutically acceptable carrier, and DMP1 or the active DMP1 fragment. In still another embodiment, the method of administering an effective amount of DMP1 or the active DMP1 fragment comprises administering an expression vector comprising a nucleic acid encoding DMP1 or the active DMP1 fragment.

The present invention also provides pharmaceutical compositions comprising a pharmaceutically acceptable carrier and DMP1 or an active DMP1 fragment. As described above, the active DMP1 fragment can act by inducing the transcription of ARF-p19.

The present invention further provides methods for diagnosing a biological sample. In one such embodiment, the biological sample comprises a eukaryotic cell suspected of being cancerous due to a mutation, deletion, or insertion in an endogenous nucleic acid encoding DMP1. A particular embodiment of this type comprises preparing a DNA or RNA sample from the cell and detecting the mutation, the deletion, or the insertion with the nucleotide sequence of SEQ ID NO:28: or a portion thereof. When the mutation, the deletion, or the insertion is detected, the presence of the mutation, the deletion, or the insertion of the endogenous nucleic acid encoding DMP1 is diagnosed. In one such embodiment of this type, the portion of SEQ ID NO:28 is a nucleotide probe. In another embodiment, the portion of SEQ ID NO:28 is a primer.

In a related embodiment, the biological sample being diagnosed comprises a eukaryotic cell suspected of being cancerous due to a significant decrease in its ability to express wild type DMP1. A particular embodiment of this type comprises preparing a sample from the cell and detecting wild type DMP1 by cross reacting the sample with an antibody for wild type DMP1. When the amount of cross-reaction with the antibody for wild type DMP1 is significantly lower than that found for a corresponding wild type cell, the cell is diagnosed as having a significant decrease in its ability to express wild type DMP1.

The present invent further provides methods for identifying an agent that modulates the ability of DMP1 to transactivate an ARF-p19 promoter. One such method comprises contacting an agent with a cell which contains DMP1 and a marker gene under the transcriptional control of an ARF-promoter that can bind DMP1. The amount of expression of the marker gene is determined. The agent is then contacted with a cell in the absence of DMP1 and the amount of expression of the marker gene is again determined. An agent is identified as modulating the ability of DMP1 to transactivate the ARF-p19 promoter when the amount of marker gene expressed is different in the presence of the agent than in its absence, and wherein in the absence of DMP1 the marker gene is not expressed or is expressed at a basal level. In a particular embodiment, the agent has a molecular weight of less than 3 kilodaltons. In another embodiment, the agent is not a naturally occurring compound.

In one embodiment the ARF-p19 promoter that binds DMP1 comprises the nucleotide sequence of SEQ ID NO:33. In another embodiment the ARF-p19 promoter that binds DMP1 comprises the nucleotide sequence of nucleotides −225 to +56 of SEQ ID NO:34. In yet another embodiment the ARF-p19 promoter that binds DMP1 comprises the nucleotide sequence of SEQ ID NO:34. In still another embodiment the ARF-p19 promoter that binds DMP1 comprises the nucleotide sequence of SEQ ID NO:35. In yet another embodiment the ARF-p19 promoter that binds DMP1 comprises the nucleotide sequence of SEQ ID NO:36 or a fragment thereof that binds DMP1.

The present invention also provides a method for identifying an agent that can mimic the ability of DMP1 to transactivate an ARF-p19 promoter. One such embodiment comprises contacting an agent with a cell that does not contain active DMP1 (i. e., active DMP1 is a form of DMP1 that binds the ARF-p19 promoter) but does contain a marker gene under the transcriptional control of an ARF-p19 promoter that binds DMP1. The amount of marker gene expressed is determined and an agent is selected when the amount of marker gene expressed is increased in the presence of the agent. The selected agent is then contacted with a cell containing an ARF-p19 promoter that does not bind DMP1 and the amount of marker gene expressed is determined. An agent is selected when the amount of marker gene expressed in the cell containing a marker gene under the transcriptional control of an ARF-p19 promoter that binds DMP1 is greater than the amount of marker gene expressed in the cell containing a marker gene under the transcriptional control of an ARF-p19 promoter that does not bind DMP1. In a particular embodiment, the increase in expression of the marker gene in the presence of the agent is at least 10% of that observed in the presence of DMP1. In a preferred embodiment, the increase in expression of the marker gene in the presence of the agent is at least 50% of that observed in the presence of DMP1. In a particular embodiment, the percent activity of the agent relative to DMP1 is based on gram to gram molecular weight basis. In an alternative embodiment, the percent activity of the agent relative to DMP1 is based on mole to mole basis. In a particular embodiment, the agent has a molecular weight of less than 3 kilodaltons. In another embodiment the agent is not a naturally occurring compound.

In one embodiment the ARF-p19 promoter that binds DMP1 comprises the nucleotide sequence of SEQ ID NO:33. In another embodiment the ARF-p19 promoter that binds DMP1 comprises the nucleotide sequence of nucleotides −225 to +56 of SEQ ID NO:34. In yet another embodiment the ARF-p19 promoter that binds DMP1 comprises the nucleotide sequence of SEQ ID NO:34. In still another embodiment the ARF-p19 promoter that binds DMP1 comprises the nucleotide sequence of SEQ ID NO:35. In yet another embodiment the ARF-p19 promoter that binds DMP1 comprises the nucleotide sequence of SEQ ID NO:36 or a fragment thereof that binds DMP1.

These and other aspects of the present invention will be better appreciated by reference to the following drawings and Detailed Description.

BRIEF DESCRIPTION OF THE DRAWINGS

FIGS. 1A–1B show the Amino Acid Sequence of murine DMP1. FIG. 1A shows the DMP1 protein sequence (SEQ ID NO:1). The three myb repeats are underlined with the first (residues 224–273) and third (residues 334–392) repeats demarcated by italics. Ser-Pro and Thr-Pro doublets are in bold face type, and acidic residues clustered at the amino- and carboxyterminal ends of the protein are indicated by double underlining. FIG. 1B shows the three myb repeats within mouse DMP1, SEQ ID NO:45 (top) and c-myb, SEQ ID NO:46 (bottom) are aligned with identical positions indicated by vertical bars. Three canonically spaced tryptophan residues (W) within each c-myb repeat are double underlined, and sites corresponding to DNA contacts in repeat-2 are indicated by asterisks. Eleven and six residue "inserts" required for maximal alignment of the two sequences are indicted above repeat-2 and repeat-3. The nucleotide sequence will be deposited in GenBank.

FIG. 4A. Lysates from Sf9 cells coinfected with wild-type baculovirus (lanes 1 and 5) or with vectors encoding the indicated D-type cyclin and CDK4 (other lanes) are used as sources of kinases to phosphorylate the GST fusion proteins indicated at the bottom of the panel. FIG. 4B. SF9 cells are coinfected with recombinant baculoviruses encoding DMP1, cyclin D2, and CDK4 (4) or CDK6 (6) as indicated at the top of the panel of the figure. Cells are metabolically labeled with either [$^{35}$S]methionine (lanes 1–8) or $^{32}$P-orthophosphate (lanes 9–12) and half of the [$^{35}$S]methionine-labeled lysates are treated with calf intestinal phosphates (lanes 5–9). All lysates are then precipitated with an antiserum to the DMP1 C-terminus, and DMP1 is resolved on denaturing gels. FIG. 4C. Sf9 cells are coinfected with the indicated baculovirus vectors encoding DMP1, D-type cyclins (D1, D2, D3), cyclin E, CDK2 (2), CDK4 (4), or a catalytically inactive CDK4 mutant (M), and cells labeled with [$^{35}$S]methionine are lysed, precipitated with antiserum to DMP1, and the protein resolved on denaturing gels. FIG. 4D. Lysates used for the experiment shown in FIG. 4C are assayed for protein kinase activity, using either a GST-RB fusion protein (lanes 1–10) or histone H 1 (lanes 11–13) as the substrate. Autoradiographic exposure times are 8 hours for FIG. 4A and 18 hours for FIGS. 4B–4D.

FIGS. 5A–5B show DMP1 oligonucleotide binding sequences. FIG. 5A. The sequences of 27 oligonucleotides selected via repeated rounds of DMP1 binding and PCR amplification are determined. The frequency of bases at 13 positions are shown at the top with a 9 base consensus defined below. FIG. 5B shows six oligonucleotides, SEQ ID NOs:10–15 respectively, all containing identical flanking sequences as indicated, are synthesized and used either as probes or competitors in the electrophoretic mobility shift assays shown in FIGS. 6–8.

FIG. 6A. Sf9 cell lysates containing approximately 4 ng recombinant DMP1 are incubated with 3 ng $^{32}$P-BS1 in the absence (lane 2) or presence (other lanes) of the indicated, unlabeled oligonucleotide competitors. The only complex detected on native gels is indicated. FIG. 6B. Parallel EMSAs are performed as in FIG. 6A. using radiolabeled BS1 or BS2 probes and 600 ng per lane of the indicated competing oligonucleotides. FIG. 6C. Assays are performed as in FIG. 6A. using a bacterial GST-ETS2 fusion protein in place of Sf9 lysates containing DMP1. Autoradiographic exposure times are 6 hours.

FIG. 8A: Lysates of NIH-3T3 cells prepared in RIPA buffer are precipitated with antiserum to DMP1 (serum AJ, lane 3) or with nonimmune serum (lane 2), and denatured immunoprecipitates are electrophoretically separated on gels. Lane 1 (taken from the same gel) is loaded with Sf9 lysate containing recombinant DMP1. Proteins transferred to nitrocellulose are detected using a 1:1 mixture of antisera AJ and AF at 1/100 dilution. Lane 1 was exposed for various times (18 hours shown) to position the hypo- and hyper phosphorylated forms of recombinant DMP1 relative to the protein detected in NIH-3T3 cells. Lanes 2 and 3 exposed for 9 days are cropped from the same film. FIG. 8B. Lysates from Sf9 cells containing DMP1 (lane 1) or from NIH-3T3 cells (lanes 2–7) are incubated with a 32P-labeled BS2 probe plus antiserum AF (lanes 3–7), together with a cognate (lane 4) or irrelevant (lane 5) peptide, or with 600 ng of competing BS2 (lane 6) or M3 (lane 7) oligonucleotide. Complexes resolved on nondenaturing gels include those previously designated A and B (FIG. 7A.) and a supershifted complex designated S in the left margin. Exposure time is 18 hours. FIG. 8C. EMSA performed with a radiolabeled BS2 probe and extracts from NIH-3T3 (lanes 2–6) or CTLL (lanes 7–12) cells. The extracts are either left untreated (none), pre-cleared with nonimmune serum (NI), or immuno-depleted with the indicated antisera to DMP1 (AF, AJ, or AH) prior to incubation with the probe. Exposure time is 18 hours.

FIG. 9A. Increasing concentrations of reporter plasmids containing a luciferase gene driven by a minimal SV40 promoter with 5' concatamerized BS1 (open circles), BS2 (closed circles), or M3 (closed squares) sequences, or no additions (open triangles) are transfected into 293T cells, and luciferase activity is determined 48 hours later. FIG. 9B. Reporter plasmids (same as FIG. 9A, 1 μg each) are cotransfected with increasing quantities of DMP1 expression plasmid, and luciferase activity is measured 48 hours later. FIG. 9C. The BS2-containing reporter plasmid was cotransfected with the DMP1 expression vector (1 μg) together with the indicated quantities of pRc/RSV expression plasmids containing cyclin D2 and/or CDK4. Background luciferase activity for the BS2 reporter plasmid in the absence of DMP1 (see 9B, 0 input) was set to 1.0 arbitrary activation units. The activation relative to this value (i.e., the activation index normalized to 0 input) is plotted on the Y-axis. For each set of experiments, the total input DNA concentrations were adjusted where necessary by addition of parental pRc/RSV plasmid DNA lacking inserts to yield 4 μg (9A), 3 μg (9B), and 2 μg (9C) of each transfection. The error bars indicate standard deviations from the mean.

FIG. 11 depicts an amino acid sequence comparison of murine DMP1(SEQ ID NO:1) and human DMP1 (SEQ ID NO:25).

FIG. 13 shows the mouse ARF promoter (SEQ ID NO:34). The nucleotide sequence of 300 base pairs 5' to the transcriptional start site (+1) is shown (GenBank AF120108). Putative binding sites for DMP1/ETS (bold type), Sp1 and E2F-1 (both underlined) are indicated. (+) indicates sense and (–) the anti-sense strand. The translational initiation codon (ATG, bold type) is at +59. The BamHI site (italics) at –225 used to construct a promoter-reporter expression plasmid is indicated by the right arrow.

FIG. 14A depicts an EMSA performed with a radiolabeled 281 base-pair ARF promoter fragment (bracketed by arrows in FIG. 13) using recombinant DMP1 made in insect Sf9 cells. Lane 1 shows results with uninfected Sf9 lysates and lane 2 with extracts of cells expressing DMP1. Competition was performed with an Ets-specific (M3, lane 3), DMP1-specific (BS2, lane 4) or a cognate ARF promoter consensus oligonucleotide (lane 5). Nonimmune serum (NRS, lane 6) or different antibodies to DMP1 (lanes 7–9) were added before probe. FIG. 14B shows an EMSA performed with a recombinant Ets1 protein (lanes 2–6) or its DNA binding domain (DBD, lane 1).

Competition was performed using the ARF promoter DMP1 consensus site (lane 3). Antibodies to Ets1 (lane 5) or DMP1 (lane 6) were added before probe. FIG. 14C shows the transactivation of the ARF promoter-reporter in NIH-3T3 cells performed by co-transfection with vectors encoding DMP1, a DMP1 mutant (M11) that cannot bind to DNA, or the indicated Ets family members (abscissa). Plasmid inputs ((g DNA) are indicated at the left. Activation (ordinate) is normalized to SEAP expression.

FIG. 15A shows that the infection of wild type MEF strains with a DMP1 virus (lanes 2 and 3) or a Myc virus (lanes 4 and 5) induces $p19^{ARF}$ protein. Amounts of protein loaded in lanes 3 and 5 were 40% of those in lanes 2 and 4. All viruses expressed the T cell co-receptor CD8; whereas 95% of Myc infected cells were CD8 positive (lane 4), only 35% of cells infected with DMP1 virus expressed the CD8 marker (lane 2). NIH-3T3 cells (lane 6) have sustained ARF-deletions, whereas 10-1 cells (lane 7) lack p53 and overexpress $p19^{ARF}$ through loss of feedback control. FIG. 15B shows the results of Wild-type (filled bars) or ARF-null (gray bars) MEFs infected for 36 hours with the indicated viruses (abscissa) that were labeled for 14 hours with BrdU and scored for protein expression and BrdU incorporation as in FIG. 16. FIG. 15C shows the results of NIH-3T3 cells that were co-transfected with the ARF promoter-reporter plasmid together with vectors encoding E2F-1 or both E2F-1 and DMP1. Input plasmid DNAs are noted on the abscissa and activation was normalized to coexpressed SEAP (ordinate). FIG. 15D shows the results of cells infected as in panel FIG. 15B that were deprived of serum for 24 hours and then scored for viability by trypan blue exclusion. Viability was confirmed using FACS-TUNEL assay and by scoring representative aliquots for subdiploid DNA content.

FIG. 17A shows the results of NIH-3T3 cells treated with 4-HT for the indicated times (hours, abscissa), were scored for activation (normalized to SEAP) of a co-transfected ARF promoter-reporter plasmid. FIG. 17B shows the results of Wild-type (closed symbols) or ARF-null (open symbols) MEFs expressing DMP1-ER™ that were left untreated (circles) or that were treated with 4-HT (squares) for the indicated times (abscissa). Cells were pulsed with BrdU for 3 hours prior to analysis. FIG. 17C shows ARF and actin mRNA that were quantitated by RT-PCR in lysates of wild type cells treated with 4-HT as in FIG. 17B or with 4-HT plus the protein synthesis inhibitor cycloheximide (CHX). FIG. 17D–17E shows ARF, p53, $p21^{Cip1}$, and actin protein levels that were determined by immunoblotting in lysates of wild type (FIG. 17D) and ARF-null (FIG. 17E) MEFs treated with 4-HT as in FIG. 17B.

DETAILED DESCRIPTION OF THE INVENTION

Figure 2:
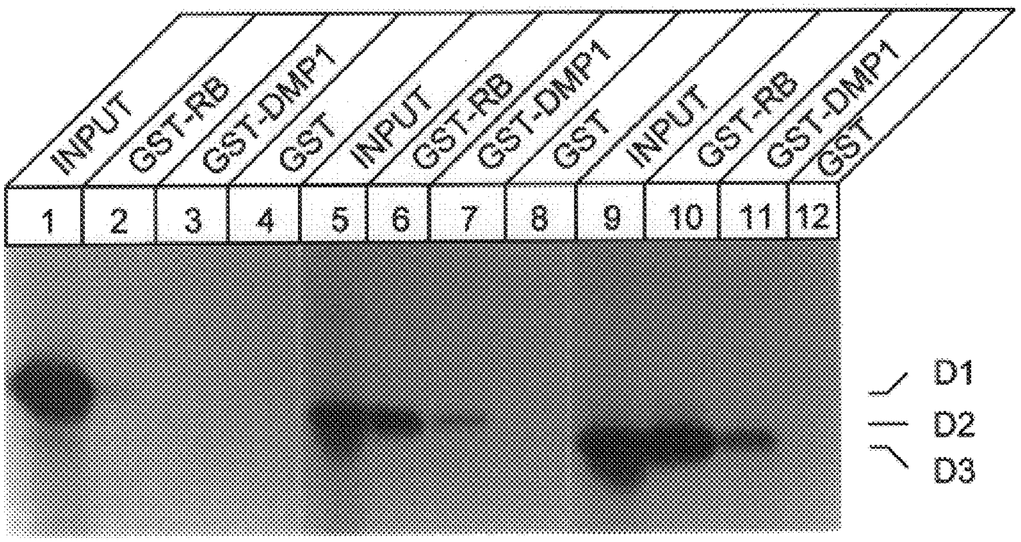
FIG. 2 shows a gel showing the binding in vitro of D-type cyclins to RB and DMP1 fusion proteins. [$^{35}$S]methionine-labeled D-type cyclins prepared by in vitro transcription and translation are mixed with the bacterially produced GST fusion proteins or GST controls as indicated above the figure. Proteins bound to glutathione-Sepharose beads are washed, denatured, and separated on gels. Lanes 1, 5, and 9 show aliquots of input radioactive proteins corresponding to 25% of that actually used in each of the subsequent binding reactions. The mobilities of the three different D-type cyclins are denoted at the right. All protein inputs and exposure times are matched.

The present invention describes a novel amino acid polymer that binds cyclin D2 and can function as a transcription factor by binding specifically to a unique nonamer consensus sequence in DNA thereby activating the transcription of genes which are regulated by the consensus sequence. One particular gene that it activates is the gene encoding ARF-p 19. The present invention includes the amino acid polymer and the corresponding nucleic acids that encode its amino acid sequence. The present invention also includes methods of making, detecting, isolating, and using the amino acid polymer as a transcription factor. Antibodies raised against the amino acid polymer, their use for detection of the amino acid polymer, corresponding antisense nucleic acids and ribozymes are also disclosed. The invention further relates to identification of a DNA-binding site for the cyclin D-associated transcription factor, and to controlling expression of a heterologous gene under control of this binding site and the transcription factor.

The present invention is based, in part, on identification of a murine transcription factor termed DMP1, isolated in a yeast two-hybrid screen using cyclin D2 as bait. This novel transcription factor is composed of a central DNA-binding domain containing three atypical myb repeats flanked by highly acidic segments located at its amino- and carboxy-terminal ends. Recombinant DMP1 specifically binds to oligonucleotides containing the nonamer consensus sequence CCCG(G/T)ATGT and, when transfected into mammalian cells, activates transcription of a reporter gene driven by a minimal promoter containing concatamerized DMP1 binding sites. Low levels of DMP1 mRNA are normally expressed, albeit ubiquitously, in mouse tissues and cell lines, and are detected in both quiescent and proliferating macrophages and fibroblasts without significant oscillation throughout the cell cycle. Correspondingly low levels of DMP1 protein are detected in cell lysates by sequential immuno precipitation and immunoblotting, and using GTA core-containing consensus oligonucleotides as probes. These extracts contained electrophoretic mobility shift assay (EMSA) activity with antigenic and oligonucleotide binding specificities indistinguishable from those of the recombinant DMP1 protein.

Expression of the DMP1 transcription factor, induces growth arrest in mouse embryo fibroblast strains but is devoid of anti-proliferative activity in primary diploid fibroblasts that lack the ARF tumor suppressor gene, ARF-p19 [Quelle, et al., *Cell* 83:993–1000 (1995); U.S. Pat. No. : 5,723,313, Issued Mar. 3, 1998; and U.S. patent application Ser. No.: 09/129,855, Filed Aug. 6, 1998, the contents of which are hereby incorporated by reference in their entireties]. DMP1 binds to a single canonical recognition site in the ARF promoter to activate gene expression, and in turn, $p19^{ARF}$ synthesis causes p53-dependent cell cycle arrest. Unlike genes such as Myc, adenovirus E1A, and E2F-1 which, when overexpressed, activate the ARF-p53 pathway and trigger apoptosis, DMP1 like ARF itself does not induce programmed cell death. Therefore, apart from its recently recognized role in protecting cells from potentially oncogenic signals, ARF can be induced in response to anti-proliferative stimuli that do not obligatorily lead to apoptosis.

Cyclin D-associated Transcription Factor

As noted above, the present invention provides an amino acid polymer that binds to cyclin D and to a specific DNA sequence. In a specific embodiment, the amino acid polymer has the sequence set forth in SEQ ID NO:1. In a preferred embodiment, the amino acid polymer has the amino acid sequence of SEQ ID NO:29. The invention further provides an antigenic fragment of the amino acid polymer, which can be used, e.g., after conjugation with a carrier protein, to generate antibodies to the amino acid polymer. Furthermore, as set forth below, the present invention contemplates the amino acid polymer containing synthetic amino acids, derivitized by acetylation or phosphorylation, or substituted with conservative amino acids that provide the same biochemical properties.

The term "amino acid polymer" as used herein, is used interchangeably with the term "polypeptide" and denotes a polymer comprising amino acids connected by peptide bonds. The amino acid polymer of this invention is a "cyclin D2 associated transcription factor", or "transcription factor" which is alternatively termed herein DMP1. The monomeric form of DMP1 contains about 760 amino acids. As used herein "about 760 amino acids" means between 685 to 835 amino acids, i.e., roughly plus or minus 10%. Human DMP1 has the amino acid sequence set forth in SEQ ID NO:29, as used herein, is a specific form of the amino acid polymer of the present invention. Murine DMP1 has an amino acid sequence set forth in SEQ ID NO:1 and is used herein as the exemplary DMP1 unless otherwise noted.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

Proteins having a slightly altered amino acid sequence from that described herein and presented in FIG. 11 (SEQ ID NOs:1 and 29), displaying substantially equivalent or altered activity are contemplated by the present invention. These modifications may be deliberate, for example, such as modifications obtained through site-directed mutagenesis, or may be accidental, such as those obtained through mutations in hosts that are producers of the complex or its named subunits.

The amino acid residues described herein are preferred to be in the "L" isomeric form and include both naturally occurring amino acids as well as amino acid analogs such as norleucine. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxyl group present at the carboxyl terminus of a polypeptide.

It should be noted that all amino acid residue sequences are represented herein by formulae whose left and right orientation is in the conventional direction of amino-terminus to carboxyl-terminus. Furthermore, it should be noted that a dash at the beginning or end of an amino acid residue sequence indicates a peptide bond to a further sequence of one or more amino-acid residues.

The amino acid polymer of the present invention may be obtained in several ways including by isolation from animal cells, by synthetic means such as solid-phase peptide synthesis or by isolation from recombinant cells that contain one or more copies of a DNA transcript encoding the amino acid polymers.

In a specific embodiment, the cyclin D associate transcription factor may be isolated by affinity binding to an oligonucleotide that comprises the DMP1 binding site, e.g., the nonanucleotide CCCGTATGT. This oligonucleotide may be conjugated (covalently associated) to a solid phase support, allowed to bind with DMP1 present, e.g, in a biological sample or in a culture after fermentation of recombinant cells, and then treated to "eluted" the protein from the oligonucleotide conjugated to the solid phase support. As one of ordinary skill in the art can readily appreciate, other affinity binding partners can be used in addition to an oligonucleotide comprising the DMP1 binding site, including anti-DMP1 antibodies and cyclin D, particularly cyclin D2.

A solid phase support for use in the present invention will be inert to the reaction conditions for binding. A solid phase support for use in the present invention must have reactive groups in order to attach a binding partner, such as an oligonucleotide containing the DMP1 binding site, cyclin D, or an antibody to the cyclin D-associated transcription factor, or for attaching a linker or handle which can serve as the initial binding point for any of the foregoing. In another embodiment, the solid phase support may be a useful chromatographic support, such as the carbohydrate polymers SEPHAROSE, SEPHADEX, and agarose. As used herein, a solid phase support is not limited to a specific type of support. Rather, a large number of supports are available and are known to one of ordinary skill in the art. Solid phase supports include silica gels, resins, derivatized plastic films, glass beads, cotton, plastic beads, alumina gels, magnetic beads, membranes (including but not limited to nitrocellulose, cellulose, nylon, and glass wool filters), plastic and glass dishes or wells, etc. For example, solid phase supports used for peptide or oligonucleotide synthesis can be used, such as polystyrene resin (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, California). In synthesis of oligonucleotides, a silica based solid phase support may be preferred. Silica based solid phase supports are commercially available (e.g., from Peninsula Laboratories, Inc.; and Applied Biosystems, Inc.). The solid phase support can be formulated as a chromatography support, e.g., in a column; it can be used in suspension followed by filtration, sedimentation, magnetic association, or centrifugation; by automated sorting (analogous to flow cytometry); or by washing, as in a membrane, well, plastic film, etc. The term "polypeptide" is used in its broadest sense to refer to a compound of two or more subunit amino acids, amino acid analogs, or peptidomimetics. The subunits may be linked by peptide bonds. In another embodiment, the subunit may be linked by other the bonds, e.g., ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^{\alpha}$-amino protected $N^{\alpha}$-t-butyloxycarbonyl) amino acid resin with the standard deprotecting, neutralization, coupling and wash protocols of the original solid phase procedure of Merrifield (1963, J. Am. Chem. Soc. 85:2149–2154), or the base-labile $N^{\alpha}$-amino protected 9-fluorenylmethoxycarbonyl (Fmoc) amino acids first described by Carpino and Han (1972, J. Org. Chem. 37:3403–3409). Both Fmoc and Boc $N^{\alpha}$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^{\alpha}$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In one aspect of the invention, the peptides may comprise a special amino acid at the C-terminus which incorporates either a $CO_2H$ or $CONH_2$ side chain to simulate a free glycine or a glycine-amide group. Another way to consider this special residue would be as a D or L amino acid analog with a side chain consisting of the linker or bond to the bead. In one embodiment, the pseudo-free C-terminal residue may be of the D or the L optical configuration; in another embodiment, a racemic mixture of D and L-isomers may be used.

The present invention further advantageously provides for determination of the structure of the transcription factor, which can be provided in sufficient quantities by recombinant expression (infra) or by synthesis. This is achieved by assays based on the physical or functional properties of the product, including radioactive labelling of the product followed by analysis by gel electrophoresis, immunoassay, etc.

The structure of transcription factor of the invention can be analyzed by various methods known in the art. Structural analysis can be performed by identifying sequence similarity with other known proteins. The degree of similarity (or homology) can provide a basis for predicting structure and function of transcription factor, or a domain thereof. In a specific embodiment, sequence comparisons can be performed with sequences found in GenBank, using, for example, the FASTA and FASTP programs (Pearson and Lipman, 1988, Proc. Natl. Acad. Sci. USA 85:2444–48).

The protein sequence can be further characterized by a hydrophilicity analysis (e.g., Hopp and Woods, 1981, Proc. Natl. Acad. Sci. U.S.A. 78:3824). A hydrophilicity profile can be used to identify the hydrophobic and hydrophilic regions of the transcription factor protein.

Secondary structural analysis (e.g., Chou and Fasman, 1974, Biochemistry 13:222) can also be done, to identify regions of transcription factor that assume specific secondary structures.

Manipulation, translation, and secondary structure prediction, as well as open reading frame prediction and plotting, can also be accomplished using computer software programs available in the art.

By providing an abundant source of recombinant transcription factor, the present invention enables quantitative structural determination of transcription factor, or domains thereof. In particular, enough material is provided for nuclear magnetic resonance (NMR), infrared (IR), Raman, and ultraviolet (UV), especially circular dichroism (CD), spectroscopic analysis. In particular NMR provides very powerful structural analysis of molecules in solution, which more closely approximates their native environment (Marion et al., 1983, Biochem. Biophys. Res. Comm. 113:967–974; Bar et al., 1985, J. Magn. Reson. 65:355–360; Kimura et al., 1980, Proc. Natl. Acad. Sci. U.S.A. 77:1681–1685). Other methods of structural analysis can also be employed. These include but are not limited to X-ray crystallography (Engstom, A., 1974, Biochem. Exp. Biol. 11:7–13).

More preferably, co-crystals of transcription factor and a transcription factor-specific ligand, preferably DNA, can be studied. Analysis of co-crystals provides detailed information about binding, which in turn allows for rational design of ligand agonists and antagonists. Computer modeling can also be used, especially in connection with NMR or X-ray methods (Fletterick, R. and Zoller, M. (eds.), 1986, Computer Graphics and Molecular Modeling, in *Current Communications in Molecular Biology,* Cold Spring Harbor Laboratory, Cold Spring Harbor, N.Y.).

Genes Encoding the Transcription Factor

The present invention contemplates isolation of a gene encoding a transcription factor of the invention, including a full length, or naturally occurring form of transcription factor, and any antigenic fragments thereof from any animal, particularly mammalian or avian, and more particularly human, source. As used herein, the term "gene" refers to an assembly of nucleotides that encode a polypeptide, and includes cDNA and genomic DNA nucleic acids.

The invention further relates, as set forth below, to preparation of recombinant expression vectors under control of DNA sequences recognized by the transcription factor of the invention.

Accordingly, in the practice of the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i. e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "heterologous nucleotide sequence" is a nucleotide sequence that is not part of the coding sequence of a nucleic acid in the nucleic acid's natural (viral or cellular) environment, but has been combined with the nucleic acid by recombinant methods. For example, a nucleic acid consisting of a nucleotide sequence encoding the amino acid polymer of the present invention (or fragment thereof) and a heterologous nucleotide sequence can encode a chimeric protein such as a fusion protein (e.g green fluorescent protein—DMP1, FLAG-DMP1, etc.).

Additionally or alternatively the heterologous nucleotide sequence can include non-coding sequences (such as regulatory or structural nucleotide sequences).

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i. e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–10.51). For hybridization with shorter nucleic acids, i.e., oligonucleotides, the position of mismatches becomes more important, and the length of the oligonucleotide determines its specificity (see Sambrook et al., supra, 11.7–11.8).

Preferably a minimum length for a hybridizable nucleic acid (such as a nucleotide probe or a primer) is at least about 12 nucleotides, preferably 24 nucleotides; more preferably at least about 36 nucleotides; and more preferably the length is at least about 48 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical (preferably greater than 50%, more preferably greater than 75%, and most preferably greater than 90 or 95%), or greater than about 60% (preferably greater than 75%, more preferably greater than 95%) are similar (functionally identical). Preferably, the similar or homologous sequences are identified by alignment using, for example, the GCG (Genetics Computer Group, Program Manual for the GCG Package, Version 7, Madison, Wis.) pileup program using the default parameters.

The term "corresponding to" is used herein to refer similar or homologous sequences, whether the exact position is identical or different from the molecule to which the similarity or homology is measured. The term "corresponding to" refers to the sequence similarity, and not the numbering of the amino acid residues or nucleotide bases.

A gene encoding transcription factor, whether genomic DNA or cDNA, can be isolated from any source, particularly from a human cDNA or genomic library. Methods for obtaining transcription factor gene are well known in the art, as described above (see, e.g., Sambrook et al., 1989, supra). Accordingly, any animal cell potentially can serve as the nucleic acid source for the molecular cloning of a transcription factor gene. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

Identification of the specific DNA fragment containing the desired transcription factor gene may be accomplished in a number of ways. For example, if an amount of a portion of a transcription factor gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). For example, a set of oligonucleotides corresponding to the partial amino acid sequence information obtained for the transcription factor protein can be prepared and used as probes for DNA encoding transcription factor, as was done in a specific example, infra, or as primers for cDNA or mRNA (e.g., in combination with a poly-T primer for RT-PCR). Preferably, a fragment is selected that is highly unique to transcription factor of the invention. Those DNA fragments with substantial homology to the probe will hybridize. As noted above, the greater the degree of homology, the more stringent hybridization conditions can be used. In a specific embodiment, stringency hybridization conditions are used to identify a homologous transcription factor gene.

Further selection can be carried out on the basis of the properties of the gene, e.g., if the gene encodes a protein product having the isoelectric, electrophoretic, amino acid composition, or partial amino acid sequence of the transcription factor protein as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for transcription factor. For example, the ability of the transcription factor to bind to a specific DNA sequence, e.g., the sequence CCCG(G/T)ATGT is indicative of its identity as a transcription factor of the invention.

The present invention also relates to cloning vectors containing genes encoding analogs and derivatives of transcription factor of the invention, that have the same or homologous functional activity as transcription factor, and homologs thereof from other species. The production and use of derivatives and analogs related to transcription factor are within the scope of the present invention. In a specific embodiment, the derivative or analog is functionally active, i.e., capable of exhibiting one or more functional activities associated with a full-length, wild-type transcription factor of the invention. Transcription factor derivatives can be made by altering encoding nucleic acid sequences by substitutions, additions or deletions that provide for functionally equivalent molecules. Preferably, derivatives are made that have enhanced or increased functional activity relative to native transcription factor.

Due to the degeneracy of nucleotide coding sequences, other DNA sequences which encode substantially the same amino acid sequence as a transcription factor gene may be used in the practice of the present invention. These include but are not limited to allelic genes, homologous genes from other species, and nucleotide sequences comprising all or portions of transcription factor genes which are altered by the substitution of different codons that encode the same amino acid residue within the sequence, thus producing a silent change. Likewise, the transcription factor derivatives of the invention include, but are not limited to, those containing, as a primary amino acid sequence, all or part of the amino acid sequence of a transcription factor protein, e.g., as set forth in SEQ ID NO:1 or SEQ ID NO:29, including altered sequences in which functionally equivalent amino acid residues are substituted for residues within the sequence resulting in a conservative amino acid substitution. These entail "conservative substitutions" as defined herein. These conservative substitutions include substitutions of one or more amino acid residues within the sequence by an amino acid of a similar polarity, which acts as a functional equivalent, and may result in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding transcription factor derivatives and analogs of the invention can be produced by various methods known in the art. The manipulations which result in their production can occur at the gene or protein level. For example, the cloned transcription factor gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of transcription factor, care should be taken to ensure that the modified gene remains within the same translational reading frame as the transcription factor gene, uninterrupted by translational stop signals, in the gene region where the desired activity is encoded.

Additionally, the transcription factor-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated transcription factor gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification,* H. Erlich, ed., Stockton Press, Chapter 6, pp. 61–70).

In a specific embodiment, a DMP1 fusion protein can be expressed. A DMP1 fusion protein comprises at least a functionally active portion of a non-DMP1 protein joined via a peptide bond to at least a functionally active portion of a DMP1 polypeptide. The non-DMP1 sequences can be amino- or carboxy-terminal to the DMP1 sequences. A recombinant DNA molecule encoding such a fusion protein comprises a sequence encoding at least a functionally active portion of a non-DMP1 protein joined in-frame to the DMP1 coding sequence, and preferably encodes a cleavage site for a specific protease, e.g., thrombin or Factor Xa, preferably at the DMP1-non-DMP1 juncture. In a specific embodiment, the fusion protein is a GST-DMP1 fusion proteins that bind directly to D-type cyclins in vitro, including radiolabeled D-type cyclins.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified.

Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli,* and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast $2\mu$ plasmid.

Expression of Transcription Factor Polypeptides

The nucleotide sequence coding for transcription factor, or antigenic fragment, derivative or analog thereof, or a functionally active derivative, including a chimeric protein, thereof, can be inserted into an appropriate expression vector, i. e., a vector which contains the necessary elements for the transcription and translation of the inserted protein-coding sequence. Such elements are termed herein a "promoter." Thus, the nucleic acid encoding the transcription factor of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding transcription factor and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant transcription factor protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding transcription factor is cultured in an appropriate cell culture medium under conditions that provide for expression of transcription factor by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of transcription factor protein may be controlled by any promoter/enhancer element known in the art, but these regulatory elements must be functional in the host selected for expression. Promoters which may be used to control transcription factor gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Transgenic Animal Models of DMP1 Activity

As noted above, the functional activity of DMP1 can be evaluated transgenically. In this respect, a transgenic mouse (or other animal) model can be used. The dmp1 gene can be introduced transgenically using standard techniques, either to provide for over expression of the gene, or to complement animals defective in the gene. Transgenic vectors, including viral vectors, or cosmid clones (or phage clones) corresponding to the wild type locus of candidate gene, can be constructed using the isolated dmp1 gene, as described below. Cosmids may be introduced into transgenic mice using published procedures [Jaenisch, *Science,* 240:1468–1474 (1988)].

Alternatively, a transgenic animal model can be prepared in which expression of the dmp1 gene is disrupted. Gene expression is disrupted, according to the invention, when no functional protein is expressed. One standard method to evaluate the phenotypic effect of a gene product is to employ knock-out technology to delete the gene. Alternatively, recombinant techniques can be used to introduce mutations, such as nonsense and amber mutations, or mutations that lead to expression of an inactive protein. In another embodiment, dmp1 genes can be tested by examining their phenotypic effects when expressed in antisense orientation in wild-type animals. In this approach, expression of the wild-type allele is suppressed, which leads to a mutant phenotype. RNA.RNA duplex formation (antisense-sense) prevents normal handling of mRNA, resulting in partial or complete elimination of wild-type gene effect. This technique has been used to inhibit TK synthesis in tissue culture and to produce phenotypes of the Kruppel mutation in Drosophila, and the Shiverer mutation in mice Izant et al., *Cell,* 36:1007–1015 (1984); Green et al., *Annu. Rev. Biochem.,* 55:569–597 (1986); Katsuki et al., *Science,* 241:593–595 (1988). An important advantage of this approach is that only a small portion of the gene need be expressed for effective inhibition of expression of the entire cognate mRNA. The antisense transgene will be placed under control of its own promoter or another promoter expressed in the correct cell type, and placed upstream of the SV40 polyA site. This transgene will be used to make transgenic mice, or by using gene knockout technology.

Expression Vectors Regulated by the Transcription Factor

In addition to expression vectors that provide for expression of the transcription factor of the invention, the present invention provides expression vectors for expression of heterologous proteins under control of the transcription factor of the invention. Such vectors include the nonanucleotide consensus sequence recognized by the cyclin D-associated transcription factor operably associated with a heterologous gene or a cassette insertion site for a heterologous gene. Preferably, such a vector is a plasmid. More preferably, the cyclin D transcription factor recognition sequence is genetically engineered into the promoter in the expression vector.

In a specific embodiment, infra, introduction of the DNA recognition sequence for the murine cyclin D transcription factor termed DMP1 was inserted in the SV40 minimal promoter and fused to a luciferase reporter gene. These plasmids express less background activity than the SV40 promoter alone.

Accordingly, the present invention provides any of the foregoing expression systems described above in connection with expression of the DMP1 transcription activator comprising the specific DNA sequence bound by DMP1 operably associated with the gene or cassette insertion site for a gene.

In a further embodiment, the present invention provides for co-expression of the transcription factor (DMP1) and a gene under control of the specific DNA recognition sequence by providing expression vectors comprising both a DMP1 coding gene and a gene under control of, inter alia, the DMP1 DNA recognition sequence. In one embodiment, these elements are provided on separate vectors, e.g., as exemplified infra. In another embodiment, these elements are provided in a single expression vector.

Antibodies to the Transcription Factor

According to the invention, transcription factor polypeptide produced recombinantly or by chemical synthesis, and fragments or other derivatives or analogs thereof, including fusion proteins, may be used as an immunogen to generate antibodies that recognize the transcription factor polypeptide. Such antibodies include but are not limited to polyclonal, monoclonal (Kohler and Milstein, 1975, Nature 256:495–497; Kozbor et al., 1983, Immunology Today 4:72; Cole et al., 1985, in *Monoclonal Antibodies and Cancer Therapy,* Alan R. Liss, Inc., pp. 77–96; PCT/US90/02545; Cote et al., 1983, Proc. Natl. Acad. Sci. U.S.A. 80:2026–2030), chimeric (Morrison et al., 1984, J. Bacteriol. 159–870; Neuberger et al., 1984, Nature 312:604–608; Takeda et al., 1985, Nature 314:452–454), single chain (U.S. Pat. No. 4,946,778), Fab fragments, and an Fab expression library. The anti-transcription factor antibodies of the invention may be cross reactive, e.g., they may recognize transcription factor from different species. Polyclonal antibodies have greater likelihood of cross reactivity. Alternatively, an antibody of the invention may be specific for a single form of transcription factor, such as murine transcription factor. Preferably, such an antibody is specific for human transcription factor.

For the production of polyclonal antibody, various host animals can be immunized by injection, including but not limited to rabbits, mice, rats, sheep, goats, etc. In one embodiment, the transcription factor polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an transcription factor polypeptide, one may assay generated hybridomas for a product which binds to an transcription factor polypeptide fragment containing such epitope. For selection of an antibody specific to an transcription factor polypeptide from a particular species of animal, one can select on the basis of positive binding with transcription factor polypeptide expressed by or isolated from cells of that species of animal.

The foregoing antibodies can be used in methods known in the art relating to the localization and activity of the transcription factor polypeptide, e.g., for Western blotting, imaging transcription factor polypeptide in situ, measuring levels thereof in appropriate physiological samples, etc.

Inhibition of Transcription Factor Expression

The present invention extends to the preparation of antisense nucleotides and ribozymes that may be used to interfere with the expression of the transcription factor at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule [See Weintraub, *Sci. Amer.* 262:40–46 (1990); Marcus-Sekura, *Nucl. Acid Res,* 15: 5749–5763 (1987); Marcus-Sekura *Anal. Biochem.,* 172:289–295 (1988); Brysch et al., *Cell Mol. Neurobiol.,* 14:557–568 (1994)]. In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro (Marcus-Sekura, 1988, supra; Hambor et al., 1988, J. Exp. Med. 168:1237). Preferably synthetic antisense nucleotides contain phosphoester analogs, such as phosphorothiolates, or thioesters, rather than natural phophoester bonds. Such phosphoester bond analogs are more resistant to degradation, increasing the stability, and therefore the efficacy, of the antisense nucleic acids.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988, J. Am. Med. Assoc. 260:3030). Because they are sequence-specific, only mRNAs with particular sequences are inactivated.

Investigators have identified two types of ribozymes, Tetrahymena-type and "hammerhead"-type [Haselhoff and Gerlach, *Nature* 334:585–591 (1988)]. Tetrahymena-type ribozymes recognize four-base sequences, while "hammerhead"-type recognize eleven- to eighteen-base sequences. The longer the recognition sequence, the more likely it is to occur exclusively in the target MRNA species. Therefore, hammerhead-type ribozymes are preferable to Tetrahymena-type ribozymes for inactivating a specific mRNA species, and eighteen base recognition sequences are preferable to shorter recognition sequences.

Therapeutic Methods and Gene Therapy

Various diseases or disorders mediated by inappropriate cell cycle activity due to increased or decreased activity of the cyclin D-associated transcription factor of the invention may be addressed by introducing genes that encode either antisense or ribozyme molecules that inhibit expression of the transcription factor (where the disease or disorder is associated with excessive transcription factor activity), or a gene that encodes an agent, such as a cyclin D, that inhibits the transcription factor (where the disease or disorder is associated with decreased transcription factor activity). In addition, in vitro or in vivo transfection with one of the foregoing genes may be useful for evaluation of cell cycle activity in an animal model, which in turn may serve for drug discovery and evaluation. In addition to treating diseases or disorders by administration of the cyclin D-associated transcription factor of the invention (DMP1), the invention contemplates using the DMP1 DNA-binding site for regulation of heterologous gene expression under control of DMP1 for gene therapy, as set forth below.

DMP1 can act as a cell cycle inhibitor when expressed in a tumor cell. In a specific embodiment, the present invention is directed to the treatment of tumors and other cancers by modulating the activity of DMP1, e.g., by enhancing expression of the transcription factor to increase its activity. In a related embodiment, the cyclin D domain of DMP1 can be modified so that the cyclins no longer can act as negative effectors of DMP1. In this case a transgene vector for expression of such a modified DMP1 of the present invention can be used. In still another embodiment, an inhibitor of the cyclins could be administered to prevent cyclin-DMP1 binding.

In the above instances, control of proliferation of a cancer cell is accomplished by blocking cell proliferation with DMP1, or an active fragment thereof thus, regulating uncontrolled cell proliferation characteristic of cancer cells. In yet another embodiment, an analogue of DMP1 can be used. Under all of the above circumstances, increased expression of genes under control of DMP1 may be necessary to restore appropriate cell cycle and growth characteristics to a transformed cell.

Examples of tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

On the other hand, agents such as drugs that inhibit the ability of DMP1 to bind DNA and/or transactivate its target genes could be administered to stimulate quiescent cells to grow. Alternatively, the invention provides for introducing an antisense nucleotide or a ribozyme specific for dmp1 mRNA; providing excess oligonucleotide containing the GTA trinucleotide sequence, and more preferably the CCCGTATGT nonanucleotide sequence to compete for binding of the transcription factor to its corresponding binding sites on gene promoters; or by increasing the level of regulatory activity effected by cyclin D to inhibit DMP1 activity.

In such cases dysproliferative changes (such as metaplasias and dysplasias) are treated or prevented in epithelial tissues such as those in the cervix, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology,* 2d Ed., W. B. Saunders Co., Philadelphia, pp. 68–79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, *Medicine,* 2d Ed., J. B. Lippincott Co., Philadelphia.

As the present invention provides for detecting the level and activity of DMP1 in cells, such as cancer cells or dysproliferative cells, the need to increase or decrease the activity of DMP1 in a given cell can be readily determined. In one embodiment, a gene for regulation of DMP1 (e.g., a dmp1 gene or an antisense gene) is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, in a specific embodiment, tumors can be specifically targeted. Examples of particular vectors include, but are not limited to, a defective herpes virus 1 (HSV1) vector (Kaplitt et al., 1991, Molec. Cell. Neurosci. 2:320–330), an attenuated adenovirus vector, such as the vector described by Stratford-Perricaudet et al. (1992, J. Clin. Invest. 90:626–630), and a defective adeno-associated virus vector (Samulski et al., 1987, J. Virol. 61:3096–3101; Samulski et al., 1989, J. Virol. 63:3822–3828). Preferably, for in vitro administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-y (IFN-γ), or anti-CD4 antibody, can be administered to block humoral or cellular immune responses to the viral vectors (see, e.g., Wilson, 1995, Nature Medicine). In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5.124,263; International Patent Publication No. WO 95/07358, published Mar. 16, 1995, by Dougherty et al.; and Kuo et al., 1993, Blood 82:845.

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner, et. al., 1987, Proc. Natl. Acad. Sci. U.S.A. 84:7413–7417; see Mackey, et al., 1988, Proc. Natl. Acad. Sci. U.S.A. 85:8027–8031)). The use of cationic lipids may promote encapsulation of negatively charged nucleic acids, and also promote fusion with negatively charged cell membranes (Felgner and Ringold, 1989, Science 337:387–388). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting (see Mackey, et. al., 1988, supra). Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

In a preferred embodiment of the present invention, a gene therapy vector as described above employs a transcription control sequence that comprises the DNA consensus sequence recognized by the transcription factor of the invention, i. e., a DMP1 binding site, operably associated with a therapeutic heterologous gene inserted in the vector. That is, a specific expression vector of the invention can be used in gene therapy. In a specific embodiment, a gene therapy vector of the invention comprises the trinucleotide sequence GTA; preferably a vector of the invention comprises the nonanucleotide sequence CCCGTATGT. Thus, the present invention specifically provides for expression of a heterologous gene under control of the cyclin D-associated transcription factor of the invention.

Such an expression vector is particularly useful to regulate expression of a therapeutic heterologous gene in conjunction with stages of the cell cycle regulated by the cyclin D-associated transcription factor of the invention. In one embodiment, the present invention contemplates constitutive expression of the heterologous gene, even if at low levels, in cells that ubiquitously express the cyclin D-associated transcription factor of the invention. Various therapeutic heterologous genes can be inserted in a gene therapy vector of the invention under the control of, inter alia, the DMP1 binding site, such as but not limited to adenosine deaminase (ADA) to treat severe combined immunodeficiency (SCID); marker genes or lymphokine genes into tumor infiltrating (TIL) T cells (Kasis et al., 1990, Proc. Natl. Acad. Sci. U.S.A. 87:473; Culver et al., 1991, ibid. 88:3155); genes for clotting factors such as Factor VIII and Factor IX for treating hemophilia [Dwarki et al. *Proc. Natl. Acad. Sci. USA,* 92:1023–1027 (19950); Thompson, *Thromb. and Haemostatis,* 66:119–122 (1991)]; and various other well known therapeutic genes such as, but not limited to, β-globin, dystrophin, insulin, erythropoietin, growth hormone, glucocerebrosidase, β-glucuronidase, α-antitrypsin, phenylalanine hydroxylase, tyrosine hydroxylase, ornithine transcarbamylase, apolipoproteins, and the like. In general, see U.S. Pat. No. 5,399,346 to Anderson et al.

In another aspect, the present invention provides for regulated expression of the heterologous gene in concert with expression of proteins under control of the cyclin D-associated transcription factor upon commitment to DNA synthesis. Concerted control of such heterologous genes may be particularly useful in the context of treatment for proliferative disorders, such as tumors and cancers, when the heterologous gene encodes a targeting marker or immunomodulatory cytokine that enhances targeting of the tumor cell by host immune system mechanisms. Examples of such heterologous genes for immunomodulatory (or immuno-effector) molecules include, but are not limited to, interferon-α, interferon-γ, interferon-β, interferon-ω, interferon-τ, tumor necrosis factor-α, tumor necrosis factor-β, interleukin-2, interleukin-7, interleukin-12, interleukin-15, B7-1 T cell costimulatory molecule, B7-2 T cell costimulatory molecule, immune cell adhesion molecule (ICAM)-1 T cell costimulatory molecule, granulocyte colony stimulatory factor, granulocyte-macrophage colony stimulatory factor, and combinations thereof.

In a further embodiment, the present invention provides for coexpression of the transcription factor (DMP1) and a therapeutic heterologous gene under control of the specific DNA recognition sequence by providing a gene therapy expression vector comprising both a DMP1 coding gene and a gene under control of, inter alia, the DMP1 DNA recognition sequence. In one embodiment, these elements are provided on separate vectors, e.g., as exemplified infra. These elements may be provided in a single expression vector.

Detection of Transcription Factor

As suggested earlier, the diagnostic method of the present invention comprises examining a cellular sample or medium by means of an assay including an effective amount of a binding partner of the transcription factor, such as an anti-amino acid polymer antibody, preferably an affinity-purified polyclonal antibody, and more preferably a mAb, or oligonucleotide containing the specific sequence.

The present invention also relates to a variety of diagnostic applications, including methods for detecting the presence of stimuli such as the earlier referenced polypeptide ligands, by reference to their ability to elicit the activities which are mediated by the present amino acid polymer. As mentioned earlier, the amino acid polymer can be used to produce antibodies to itself by a variety of known techniques, and such antibodies could then be isolated and utilized as in tests for the presence of particular transcription activation activity in suspect target cells.

The procedures and their application are all familiar to those skilled in the art and accordingly may be utilized within the scope of the present invention. For example, a "competitive" procedure is described in U.S. Pat. Nos. 3,654,090 and 3,850,752. A "sandwich" procedure is described in U.S. Pat. Nos. RE 31,006 and 4,016,043. Still other procedures are known such as the "double antibody," or "DASP" procedure.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The amino acid polymer or its binding partner(s) can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

Other means for detecting specific binding are well known in the art, including biosensors such as the BIAcore™ system (Pharmacia Biosensor AB, Uppsala, Sweden), or optical immunosensor systems. These systems can be grouped into four major categories: reflection techniques; surface plasmon resonance; fiber optic techniques, and integrated optic devices. Reflection techniques include ellipsometry, multiple integral reflection spectroscopy, and fluorescent capillary fill devices. Fiber-optic techniques include evanescent field fluorescence, optical fiber capillary tube, and fiber optic fluorescence sensors. Integrated optic devices include planer evanescent field fluorescence, input grading coupler immunosensor, Mach-Zehnder interferometer, Hartman interferometer and difference interferometer sensors. Holographic detection of binding reactions is accomplished detecting the presence of a holographic image that is generated at a predetermined image location when one reactant of a binding pair binds to an immobilized second reactant of the binding pair (see U.S. Pat. No. 5,352,582, issued Oct. 4, 1994 to Lichtenwalter et al.). Examples of optical immunosensors are described in general in a review article by G. A. Robins (Advances in Biosensors), Vol. 1, pp. 229–256, 1991. More specific description of these devices are found for example in U.S. Pat. Nos. 4,810,658; 4,978,503; 5,186,897; R. A. Brady et al. (Phil. Trans. R. Soc. Land. B 316, 143–160, 1987) and G. A. Robinson et al. (in Sensors and Actuators, Elsevier, 1992).

Since DMP1 can act as a cell cycle inhibitor when expressed in a tumor cell, a specific peptide domain of DMP1 is likely to be responsible for this property. In particular, the transactivation domain of a DMP1 (or an expression vector containing a nucleic acid encoding the same) can be administered to stimulate the expression of the genes under control of DMP1-responsive promoters that aid in the prevention of cell proliferation. In a particular embodiment the transactivation domain comprises amino acids 459 to 761 of SEQ ID NO:1 or SEQ ID NO:18. In a related embodiment the transactivation domain comprises amino acids 1–86 (SEQ ID NO:20) and 459 to 761 (SEQ ID NO:18) of SEQ ID NO:1.

DMP1 also contains a specific DNA-binding domain that by itself is incapable of transactivating genes controlled by DMP1-responsive promoters. In a specific embodiment this DNA-binding domain consists of amino acids 87–458 (SEQ ID NO:16) of SEQ ID NO:1. In particular, the DNA-binding domain of a DMP1 (or an expression vector containing a nucleic acid encoding the same) can be administered to inhibit the expression of the genes under control of DMP1-responsive promoters by competing with endogenous DMP1 and thereby aid in cell proliferation. In a particular embodiment of the present invention, the gene that is effected is the ARF-p19 gene. DMP1, the DMP1-binding domain, and/or the transactivation domain of DMP1 also can be used to identify alternative DMP1 target genes that are responsible for the regulation of cell growth.

Drug Assays

Identification and isolation of a gene encoding an DMP1 of the present invention provides for expression of DMP1 in quantities greater than can be isolated from natural sources, or in indicator cells that are specially engineered to indicate the activity of DMP1 expressed after transfection or transformation of the cells. Accordingly, in addition to rational design of agonists and antagonists, including drugs, based on the structure of DMP1 polypeptide, the present invention contemplates an alternative method for identifying specific ligands and/or effectors of DMP1 using various screening assays known in the art. Such effectors could be used to manipulate the timing of the cell division cycle, since DMP1 is a transcription factor which is involved in the regulation of genes that prevent cell proliferation.

Any screening technique known in the art can be used to screen for DMP1 agonists or antagonists. The present invention contemplates screens for small molecule effectors, ligands or ligand analogs and mimics, as well as screens for natural ligands that bind to and agonize or antagonize activates DMP1 in vivo. For example, natural products libraries can be screened using assays of the invention for molecules that agonize or antagonize DMP1 activity.

Knowledge of the primary sequence of DMP1, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249:386–390 (1990); Cwirla, et al., *Proc. Natl. Acad. Sci.,* 87:6378–6382 (1990); Devlin et al., *Science,* 249:404–406 (1990)], very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [*14th International Congress of Biochemistry, Volume* 5, Abstract FR:013 (1988); Furka, *Int. J. Peptide Protein Res.* 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for DMP1 ligands, e.g., agonists or antagonists, according to the present invention.

The screening can be performed with recombinant cells that express DMP1, or alternatively, using purified protein, e.g., produced recombinantly, as described above. For example, the ability of labelled or unlabelled DMP1, the DNA-binding domain of DMP1, the cyclin D binding domain of DMP1, and/or the transactivation domain of DMP1, all of which have been defined herein, can be used to screen libraries, as described in the foregoing references.

The present invention provides novel assays to identify agents that modulate the ability of DMP1 to transactivate an ARF-p19 promoter. Other assays are provided for identifying agents that mimic DMP1 as an activator of ARF-p19 activity. Such agents are particulary desirable since the other factors that activate $p19^{ARF}$ synthesis, e.g., Myc and E2F, are normally countered by ARF-dependent signals when overexpressed. These ARF-dependent signals antagonize rapid cell proliferation and help to promote apoptosis in a p53-dependent manner. Because the ARF and DNA damage pathways that impinge on p53 are distinct, activation of ARF by low levels of Myc or E1A can sensitize cells to the p53-dependent effects of genotoxic drugs or irradiation. However, the growth promoting properties of Myc and E1A also contribute to rapid selection of drug-resistant variants that lose ARF-p53 checkpoint control. Because DMP1 and mimicks thereof, exhibit no overt growth promoting functions and do not create the risk of selection for p53-negative variants, they are useful as specific sensitizers of p53-dependent killing in response to common chemotherapeutic regimens.

Therefore, the present invention provides assays for identifying agents that modulate or mimic the activity of DMP1 to induce cell cycle arrest without provoking cell death. Such assays can employ the nonamer binding sequence for DMP1 of the murine ARF-p19 promoter (SEQ ID NO:33), the nonamer binding sequence for DMP1 of the human ARF-p19 promoter (SEQ ID NO:35), the murine ARF-p19 promoter (SEQ ID NO:34) and fragments thereof, as well as the human ARF-p19 promoter (SEQ ID NO:36) and fragments thereof. In addition such assays can employ genetic variants of these ARF-p19 promoters that do not bind DMP1.

In one particular embodiment, the ARF-p19 promoter (or fragment thereof) is placed into a reporter plasmid with a marker gene (such as one encoding SEAP, luciferase, or the green fluorescent protein) under its transcriptional control. The reporter plasmid is then placed into a cell (e.g., a NIH-3T3 fibroblast cell) that does not contain DMP1. The cell is then contacted with an agent. An agent that mimicks DMP1 can be identified by an increase in the expression of the marker gene. The cell can be co-transfected with a DMP1 expression plasmid in the absence of the agent as a control (the DMP1 expression plasmid should also cause an increase in the expression of the marker gene). In a particular embodiment, the agent is contacted with a cell that contains a reporter plasmid having a marker gene under the transcriptional control of an ARF-p19 promoter that has been modified so as not to bind DMP1. An agent that mimicks DMP1 can be identified when there isn't a corresponding increase in the expression of the marker gene under the control of the ARF-p 19 promoter that does not bind DMP1.

In a particular embodiment, electrophoretic mobility shift assays (EMSA) assays are also performed using labeled (e.g., $^{32}P$) synthetic oligonucleotides or PCR-amplified fragments of the promoter with DMP1. An agent is identified if it interferes/competes with the binding of the promoter with DMP1, i. e., inhibits or prevents the electrophoretic mobility shift in the EMSA assay in the presence of DMP1. In a preferred embodiment, an agent that is identified can be further tested in a cell that naturally contains ARF-p19, and its effect on ARF-p19 expression is determined (see Example 10). As a control, a cell with a non-functional ARF-p19 can be used to demonstrate that the effect of the agent is ARF-p19-dependent.

In a related embodiment an agent can be identified that modulates the ability of DMP1 to transactivate an ARF-p19 promoter. Agents can be either agonists or antagonists. In a particular assay, the promoter (or fragment thereof) is placed into a reporter plasmid with a marker gene (such as one encoding SEAP, luciferase, or the green fluorescent protein) under its transcriptional control. The reporter plasmid is then placed into a cell (e.g., a NIH-3T3 fibroblast cell) that contain DMP1s. The cell is then contacted with an agent. An agent that modulates DMP1 can be identified by a change in the expression of the marker gene. In a particular embodiment the DMP1 is supplied by an expression vector. In this case an agent that is selected can be further tested in the absence of DMP1. An agent that modulates DMP1 can be identified by the lack of a change in the expression of the marker gene in the absence of DMP1. An agonist is identified when the effect of DMP1 is increased, whereas an antagonist is identified when the effect of DMP1 is decreased.

In a particular embodiment, electrophoretic mobility shift assays (EMSA) are also performed using labeled (e.g., $^{32}P$) synthetic oligonucleotides or PCR-amplified fragments of the promoter with DMP1. An agent that is a modulator is further identified if it enhances or diminishes the binding of the promoter with DMP1, i.e., inhibits or enhances the amount of electrophoretic mobility shift in the EMSA assay. In a preferred embodiment, an agent that is identified can be further tested in a cell that naturally contains ARF-p19, and its effect on ARF-p19 expression is determined (see Example 10). As a control, a cell with a non-functional ARF-p19 can be used to demonstrate that the effect of the agent is indeed ARF-p19-dependent.

Genes that are under the control of a DMP1-responsive promoter can be identified through the use of the subtractive library method enhanced by the polymerase chain reaction (PCR), which allows performance of multiple cycles of hybridization using small amounts of starting material [Wieland et al., *Proc. Natl, Acad. Sci. USA,* 87:2720–2724 (1990)]; [Wang et al., *Proc. Natl. Acad. Sci. USA,* 88:11505–11509 (1991)]; [Cecchini et al, *Nucleic Acids Res.,* 21:5742–5747 (1993)]. Two cDNA libraries can be prepared from NIH-3T3 fibroblast cells, for example. One cDNA library is obtained from cells transfected with an expression vector encoding DMP1, whereas the control cDNA library is obtained from proliferating NIH-3T3 cells that have not been so transfected.

The present invention also provides alternative assays for identifying genes that are transactivated by DMP1. In one such embodiment, naturally occurring promoters are examined to determine if they contain a putative DMP1 consensus binding site. Promoters that contain a putative DMP1 consensus binding site are selected to be placed into a reporter plasmid with a marker gene (such as one encoding SEAP, luciferase, or the green fluorescent protein) under the transcriptional control of the promoter. The reporter plasmid is then placed into a cell (e.g., a NIH-3T3 fibroblast cell) which can be co-transfected with a DMP1 expression plasmid. A promoter that is transactivated by DMP1 can be identified by the expression of the marker gene that it controls. One such promoter that was identified by this procedure is the promoter for the CD13/Aminopeptidase N gene [See, Inoue, et al, *J Biol. Chem.* 273:29188–29194 (1998), hereby incorporated by reference in its entirety]. Other genes that may contain promoters with a putative DMP1 consensus binding site include the human interleukin-2 receptor alpha chain, human interleukin 9 receptor, human prostacyclin receptor, human MDR3, human rat nerve growth receptor, mouse c-rel, mouse ornithine aminotransferase, and rat p53.

A related method for identifying candidate genes that are transactivated by DMP1 is exemplified as follows: A plasmid that contains promoter regions of a candidate gene is constructed or otherwise obtained. The promoter fragments can then be subcloned into a pGL2-basic vector (or comparable vector). The vector is placed into a cell (e.g., a NIH-3T3 fibroblast cell). The promoter is constructed to have a marker gene (such as one encoding SEAP, luciferase, or the green fluorescent protein) under the transcriptional control of the promoter. The vector containing the promoter/marker gene construct is then placed into a cell (e.g., a NIH-3T3 fibroblast cell) which can be co-transfected with a DMP1 expression plasmid. The expression of the marker gene is determined (e.g., luciferase assays) in the presence and absence of DMP1 (e.g., the presence or absence of the DMP1 expression vector). A promoter that is transactivated by DMP1 can be identified by the increased expression of the marker gene in the presence of DMP1 relative to in the absence DMP1. In a preferred embodiment, a DMP1 variant/mutant (as exemplified in Example 10) that does not bind DNA and/or is missing the transactivation domains is introduced into the cell as a control. A promoter that is transactivated by DMP1 can be identified by the increased expression of the marker gene in the presence of wild type DMP1 relative the DMP1 variant/mutant. In another preferred embodiment, electrophoretic mobility shift assays (EMSA) assays are also performed using labeled (e.g., $^{32}P$) synthetic oligonucleotides or PCR-amplified fragments of the promoter with DMP1. A promoter that is binds DMP1 can be identified by an electrophoretic mobility shift in the EMSA assay in the presence of DMP1. In a preferred embodiment, biological experiments as those exemplified below are performed. For example, vectors encoding DMP1 and/or a DMP1 variant/mutant that does not bind DNA and/or is missing the transactivation domains can be introduced into cells that contain the promoter in its natural setting. The expression of the protein under the transcriptional control of the promoter can then be determined in the presence of the DMP1 and the mutant/variant. A promoter that is transactivated by DMP1 can be identified by the increased expression of the protein in the presence of wild type DMP1 relative the DMP1 variant/mutant. If a particular biological effect can be correlated with the expression of the protein under the transcriptional control of the promoter, the experiment can be repeated in a cell in which the protein under the transcriptional control of the promoter has been made non-functional as a control (see Example 10, below).

The following examples are presented in order to more fully illustrate the preferred embodiments of the invention. They should in no way be construed, however, as limiting the broad scope of the invention.

EXAMPLES

Various references cited herein by number are listed after the Examples, infra.

Materials and Methods

Cells and Culture Conditions

Mouse NIH-3T3 fibroblasts and 293T human embryonic kidney cells (18) are maintained in a 10% $CO_2$ sterile incubator at 37° C. in Dulbecco's modified Eagle's medium (DMEM) supplemented with 10% fetal bovine serum (FBS), 2 mM glutamine, and 100 units/ml penicillin and streptomycin (GIBCO/BRL Gaithersburg Md.). Mouse CTLL T lymphocytes are grown in RPMI 1640 medium using the same supplements plus 100 units/ml recombinant mouse interleukin-2 (a generous gift of Dr. Peter Ralph, formerly of Cetus Corp, now Chiron). Spodoptera frugiperda Sf9 cells are maintained at 27° C. in Grace's medium containing 10% FBS, yeastolate, lactalbumin hydrolysate, and gentimycin (all from GIBCO/BRL) in 100 ml spinner bottles.

Isolation of DMP1

A yeast two hybrid system (5,14) as employed previously (20) was used to isolate cDNAs encoding cyclin D2 binding proteins. A BamHI-HindIII cDNA fragment encoding mouse cyclin D2 (35,36) is subcloned into plasmid pAS2 in frame with the yeast GAL4 DNA-binding domain to generate the pAS2cycD2 bait plasmid. Yeast strain Y190, whose HIS3 and LacZ genes are induced by GAL4, is transformed with pAScycD2 and then with a pACT library (Clonetech, Palo Alto Calif.) containing cDNAs prepared from mouse T-lymphoma cells fused 3' to the GAL4 transcription activation domain. Of $6\times10^5$ colonies screened, 107 grew on SD synthetic medium lacking histidine and express β-galactosidase. Colonies that had been induced to segregate the bait plasmid were mated with yeast strain Y187 containing either pAS2cycD2 or unrelated control plasmids expressing yeast SNF1 or human lamin fused to the GAL4 DNA-binding domain. cDNAs from 36 library-derived plasmids presumed to encode cyclin D2-interacting proteins are sequenced, one of which encodes a cyclin D-binding myb-like protein, here designated DMP1. The nucleotide sequence for the mouse DMP1 will be submitted to GenBank.

Because the recovered DMP1 cDNA (2.6 kb 3' of GAL4) is shorter than the single mRNA species detected in mouse tissues by Northern blotting analysis, plaque lifts representing $4\times10^6$ phages from a mouse C19 erythroleukemia cell cDNA library (5' stretch gt10, Clonetech) are screened with a radiolabeled DMP1 probe, and two cDNAs containing additional 5' sequences are isolated. These contain 200 and 373 bp segments overlapping those at the 5' end of the probe plus ~800 bp of novel 5' sequences. The latter sequences are fused within the region of overlap to those in the 2.6 kb DMP1 cDNA to generate a putative full-length cDNA of 3.4 kb.

In vitro Binding and Protein Kinase Assays

A BglII fragment encoding amino acids 176–761 of DMP1 (FIG. 1) is subcloned into the BamHI site of the pGEX-3X plasmid (Pharmacia, Uppsala Sweden), and overnight cultures of transformed bacteria are diluted 10-fold with fresh medium, cultured for 2–4 more hours at 37° C., and induced with 1 mM isopropyl-β-D-thiogalactopyranoside (IPTG) for 1 hour. Induced bacteria are lysed by sonication in phosphate-buffered saline (PBS) containing 1% Triton X-100, and recombinant glutathione-S-transferase (GST)-DMP1 protein is purified by absorption and elution from glutathione-Sepharose beads as described (35). For in vitro binding, 1.5 μg of GST-DMP1 or GST-RB (15) immobilized on glutathione-Sepharose beads are mixed with [$^{35}$S]methionine-labeled mouse D-type cyclins, prepared by transcription (Stratagene Transcription System, La Jolla Calif.) and translation (rabbit reticulocyte system from Promega, Madison Wis.) in vitro, as per the manufacturer's instructions, hereby incorporated by reference. Proteins are mixed in 0.5 ml of IP Kinase buffer (50 mM HEPES, pH 7.5, 150 mM NaCl, 1 mM EDTA, 1 mM dithiothreitol (DTT), 0.1% Tween-20) containing 10 mg/ml bovine serum albumin (BSA, Cohn Fraction V, Sigma Chemicals, St. Louis Mo.). After 2 hours at 4° C., the beads are collected by centrifugation, washed 4 times with IP Kinase buffer, and the bound proteins are denatured and analyzed by electrophoresis on 11% polyacrylamide gels containing sodium dodecyl sulfate (SDS) (1).

Protein kinase assays are performed using 1.5 μg GST-DMP1 or GST-RB adsorbed to glutathione-Sepharose as substrates. The beads are suspended in a total volume of 25 μl Kinase buffer (50 mM HEPES, pH 7.5, 10 mM $Mg_2Cl$, 1 mM DTT) containing 1 mM EGTA, 10 mM β-glycerophosphate, 0.1 mM sodium orthovanadate, 1 mM NaF, 20 uM ATP, 1 uCi [-$^{32}$P]ATP (6000 Ci/mmol; Amersham), and 2.5–5.0 μl lysate (corresponding to $5\times10^4$ cell equivalents) from Sf9 cells coinfected with the indicated cyclins and CDKs. After incubation for 20 minutes at 30° C. (with linear incorporation kinetics), the total proteins in the reaction are denatured and, following centrifugation of the beads, separated on denaturing polyacrylamide gels.

Antisera and Immunoblotting

Rabbit antisera to recombinant DMP1 are commercially prepared (Rockland, Gilbertsville Pa.) using hexahistidine (His)-tagged fusion proteins produced in bacteria (32) and containing fused DMP1 residues 221–439 (serum AJ to myb-repeat domain) or residues 176–761 (serum AH). Antiserum AF is raised against a synthetic peptide representing the nine C-terminal DMP1 residues conjugated to keyhole limpet hemocyanin as described (13). All antisera specifically precipitate multiple phosphorylated forms of the full-length DMP1 protein from Sf9 lysates infected with a DMP1-producing baculovirus vector and do not crossreact with mammalian cyclins (D-types, E, A, or B) or CDKs (2, 4, and 6). To detect DMP1 in cultured mammalian cells, untreated CTLL cells ($4\times10^7$) or transfected 293T cells ($1.5\times10^6$) are suspended and sonicated in 1 ml of RIPA buffer [50 mM Tris HCl, pH 7.5, containing 150 mM NaCl, 1% Nonidet P40, 0.5% sodium deoxycholate, and 0.1% SDS] and clarified by centrifugation. DMP1 was precipitated with 10 ul of antiserum AJ, denatured and electrophoretically separated on 9% polyacrylamide gels containing SDS, and transferred to nitrocellulose. The filter is incubated with a 1/100 dilution of AJ and AF antisera, and sites of antibody binding were detected using $^{125}$I-protein A (Amersham) as described (12).

Expression of Recombinant DMP1 in Insect Cells

BamHI linkers are added to an XbaI-EcoRV cDNA fragment containing the entire DMP1 coding sequence, and the fragment is inserted into the BamHI site of the pAcYM1 baculovirus vector (37). Production of virus and infection of *Spodoptera frugiperda* (Sf9) cells are performed as previously described (23). For preparation of radiolabeled cell lysates, cells infected with the indicated recombinant viruses encoding DMP1, CDKs, and/or cyclins are metabolically labeled 40 hours post-infection for 8 additional hours with 50 uCi/ml of [$^{35}$S]methionine (1000 Ci/mmol; ICN, Irvine Calif.) in methionine-free medium or for 4 additional hours with 250 uCi/ml of carrier-free $^{32}$P-orthophosphate (9000 Ci/mmol, Amersham) in phosphate-free medium. Cells suspended in 0.25 ml Kinase buffer containing protease and phosphatase inhibitors [2.5 mM EGTA, 0.1 mM phenylmethyl sulfonylfluoride (PMSF), 2% aprotinin, 1 mM β-glycerophosphate, 0.1 mM $Na_3VO_4$, and 0.1 mM NaF] are lysed by repeated freezing and thawing and clarified by centrifugation. For detection of DMP1 or its complexes with D-type cyclins, 10–20 μl lysate is diluted to 0.5 ml in EBC buffer (50 mM Tris Hcl, pH 8.0, 120 mM NaCl, 0.5% Nonidet P-40, 1 mM EDTA, and 1 mM DTT) containing 2% aprotinin, 1 mM β-glycerophosphate, 0.1 mM $Na_3VO_4$, and 0.1 mM NaF. Antiserum AF (10 μl adsorbed to protein A-Sepharose beads) directed to the DMP1 C-terminus was added, beads are recovered after incubation for 4 hours at 4° C., and absorbed proteins are denatured and resolved on denaturing gels. Where indicated, metabolically labeled Sf9 lysates are treated with calf intestinal phosphatase after immune precipitation (23). Determination of cyclin dependent kinase activities in the cell extracts is performed using soluble GST-RB or histone H1 (Boehringer Mannheim, Indianapolis Ind.) as substrates.

Selection of DMP1 Binding Consensus Oligonucleotides

Binding site selection and amplification by polymerase chain reaction (PCR) is performed as described (21). Single-stranded oligonucleotides containing 30 random bases interposed between fixed forward (5'-CGCGGATCCTGCAGCTCGAG-3' SEQ ID NO:5) and reverse (5'-TGCTCTAGAAGCTTGTCGAC-3' SEQ ID NO:6) primers are prepared, and then double-stranded oligonucleotides are generated using them as templates with the forward and reverse primers. The double-stranded oligonucleotides are mixed with recombinant DMP1 protein immunoprecipitated from Sf9 cells and immobilized to protein A beads. Mixing is performed in 125 μl of Binding buffer (25 mM HEPES, pH 7.5, 100 mM KCl, 1 mM EDTA, 1.5 mM $MgCl_2$, 0.1% Nonidet P40, 1 mM DTT, 5% glycerol) containing 25 μg poly (dI-dC) (Boehringer Mannheim) and 25 μg BSA, followed by incubation with gentle rotation for 30 minutes at 4° C. Beads are collected by centrifugation, washed 3 times with Binding buffer, and suspended in 50 μl distilled water. Bound oligomers eluted into the supernatant by boiling are reamplified by PCR using the same primers. After 6 rounds of binding and amplification, recovered oligonucleotides are subcloned into the BamHI to HindIII sites of pSK bluescript plasmids (Stratagene, La Jolla Calif.) and their sequences are determined using a Sequenase version 2.0 kit (U.S. Biochemicals, Cleveland Ohio).

Electrophoretic Mobility Shift Assay (EMSA)

Double-stranded oligonucleotides containing potential DMP1 binding sites (BS1 and BS2) and mutated versions (M1–M4) (FIG. 5B) are end-labeled with $^{32}P$ using the Klenow fragment of DNA polymerase and α-$^{32}$P-dATP (6000 Ci/mmol; Dupont NEN) (8). Nuclear extracts from mouse NIH-3T3 or CTLL cells are prepared with buffer containing 0.4 M NaCl (2). Mammalian cell extracts (15 μg protein) or Sf9 lysates (corresponding to $5\times10^2$ infected cells) containing ~4 ng recombinant DMP1 are mixed with 3 ng of $^{32}$P-labeled probe ($1\times10^5$ cpm) in 15 ul Binding buffer containing 2.5 μg of poly(dI-dC) and 2.5 μg BSA and incubated at 4° C. for 30 minutes. For competition experiments, the indicated amounts of unlabeled oligonucleotides are added to the reactions before addition of the labeled probe. In some experiments, a bacterially produced GST-Ets2 fusion protein containing the complete Ets2 DNA-binding domain (10) is used in place of Sf9 extracts containing recombinant DMP1. Protein-DNA complexes are separated on nondenaturing 4% polyacrylamide gels as described (8). Where indicated, antiserum to DMP1 together with 2.5 μg salmon testis DNA (Sigma; used to reduce nonspecific DNA binding activity, caused by serum addition) is preincubated with extracts for 30 minutes at 4° C. prior to initiation of binding reactions. Immune complexes are either removed by adsorption to protein A-Sepharose beads (immunodepletion experiments) or are allowed to remain ("supershift" experiments).

Transactivation Assay

An XbaI-EcoRV fragment containing the entire DMP1 coding sequence is subcloned by blunt end ligation into a SpeI-XbaI fragment of the Rc/RSV vector (Invitrogen, La Jolla Calif.) to enable DMP1 expression in mammalian cells. 6× concatamerized BS1, 8× concatamerized, BS2, or 7× concatamerized M3 oligonucleotides (FIG. 5B) are inserted into the XhoI-SmaI sites of pGL2 (Promega) 5' to a minimal simian virus 40 (SV40) early promoter driving firefly luciferase gene expression. The latter "reporter" plasmid (1 μg) together with increasing amounts of pRc/RSV-DMP1 expression plasmid compensated by decreasing quantities of control pRc/RSV DNA (total of both=2.5 μg) were transfected into 293T cells ($1.5\times10^6$ cells per 60 mm diameter culture dish) by calcium phosphate precipitation (7). Two days later, cells were harvested, washed three times with PBS, and lysed in 1 ml of 25 mM glycylglycine (Sigma), pH 7.8, 15 mM $MgSO_4$, 4 mM EDTA, 1 mM DTT, and 1% Triton X-100. After clearing by centrifugation, 50 μl aliquots were assayed diluted to 350 μl using 15 mM potassium phosphate buffer, pH 7.8, containing 15 mM $MgSO_4$, 4 mM EGTA, 2 mM ATP, 1 mM DTT, and 67 uM luciferin (Sigma). Total light emission was measured for duplicate samples during the initial 20 seconds after luciferin injection with an Optocomp I luminometer (MGM Instruments, Hamden Conn.).

Fluorescence in situ Hybridization for Chromosome Determination

Phytohemagglutinin-stimulated human peripheral blood lymphocytes from a normal donor were used as the source of metaphase chromosomes. Purified DNA from P1 clone 11098 was labeled with digoxigenin-11-dUTP (Boehringer Mannheim, Indianapolis, Ind.) by nick translation and hybridized overnight at 37° C. to fixed metaphase chromosomes in a solution containing sheared human DNA, 50% formamide, 10% dextran sulfate, and 2×SSC. Specific hybridization signals were detected by incubating the hybridized slides in fluorescein-conjugated sheep antibodies to digoxigenin (Boehringer Mannheim, Indianapolis, Ind.). The chromosomes were then counterstained with 4,6-diamidino-2-phenylindole (DAPI) and analyzed. Definitive chromosomal assignment was confirmed by cohybridization of clone 11098 with a biotinalyted chromosome 7 centromere-specific probe (D7Z1)(Oncor Inc., Gaitherburg, Md.). Specific probe signals were detected by incubating the hybridized slides in fluorescein-conjugated sheep antibodies to digoxigenin and Texas red avidin (Vector Laboratories, Burlington Calif.). Chromosome band assignment was made based on the relative position of the fluorescence signal relative to landmarks on the chromosome such as centromere, telomeres, and heterochromatic euchromatic boundaries [Franke, *Cytogenet Cell Genet* 65:206–219 (1994)].

Human C-Terminal Fragment

EST T90434 was purchased from Genome Systems Inc., St Louis, Mo. The EST was selected on the basis of the homology of 289 nucleotides sequenced with that of SEQ ID NO:2; 78.4% identity was reported. Upon resequencing the EST, it was found that some of the 289 base pairs had been incorrectly assigned.

Staining for the Expression of DMP1 and Incorporation of BrdU in Transfected Cells BrdU is added to NIH-3T3 cells after the experimental treatment and the cells were incubated for twenty-two hours in DMEM plus 10% fetal calf serum (FCS). The cells were then stained for DMP1 expression and/or BrdU incorporation. The nucleic acids encoding the wildtype DMP1 and the deletion and point mutants had been constructed so as to express the corresponding proteins with Flag-tags. To stain for DMP1 expression, mouse monoclonal anti-Flag antibodies (12 μg/ml) [Kodak] were incubated with the cells in TBS-$Ca^+$ without FCS for one hour at room temperature. After washing the cells, horse anti-mouse biotinylated antibodies at a 1:500 dilution were added to the cells in TBS plus 5% FCS and incubated for 30 minutes at room temperature. After washing the cells, streptavidin linked to Texas red [Amersham] was then added at a 1:500 dilution for 30 minutes at room temperature. To stain for BrdU incorporation, 1.5N HCl was added to the cells for ten minutes at room temperature to denature the DNA. After washing the cells, sheep anti-BrdU antibodies [Fitzgerald] at a 1:12 dilution were then added for one hour at room temperature. After washing the cells, rabbit FITC-conjugated anti-sheep antibodies [Vector] at 1:100 dilution was then incubated for 30 minutes at room temperature.

Isolation of Clone 11098

A genomic probe for DMP1 was prepared by PCR with a primer having a nucleotide sequence of a portion of the C-terminal fragment of human DMP1 (obtained by sequencing EST T90434) and human genomic DNA. The probe was then used to obtain Clone 11098 from a P1 human genomic DNA library.

Example 1

Isolation and Molecular Features of DMP1

A yeast two-hybrid screen is used to isolate cDNAs encoding proteins able to interact with cyclin D2. Plasmids containing cDNAs prepared from the RNA of mouse T lymphoma cells and fused 3' to the GAL4 activation domain are transfected into yeast cells containing a "bait plasmid" encoding the GAL4 DNA-binding domain fused in frame with full length mouse cyclin D2 coding sequences. From $6\times10^5$ transformants, 36 plasmids are isolated which, when segregated and mated with yeast containing the cyclin D2 bait plasmid or with control strains expressing unrelated GAL4 fusion proteins, coded for proteins that interacted specifically with D-type cyclins. These cDNAs specify several previously identified cyclin D-interacting proteins (i.e. known CDKs and CDK inhibitors) as well as novel polypeptides unrelated to those in searchable data bases. Among the latter group is a single clone encoding a protein containing three tandem "myb repeats" characteristic of the myb family of transcription factors (17,24,45). Northern blot analysis reveals that a single ~3.8 kb mRNA related to the cloned sequences is present ubiquitously in adult mouse tissues (i.e. heart, brain, spleen, lung, liver, kidney, testis) and mouse cell lines (NIH-3T3 fibroblasts, BAC1.2F5 macrophages, CTLL T cells, and MEL erythroleukemia cells), and it is nonperiodically expressed throughout the cell cycle in synchronized macrophages and fibroblasts (data not shown). Overlapping cDNAs containing 0.8 kb of additional 5' sequences are isolated from a mouse erythroleukemia (MEL) cell library, enabling the reconstruction of a 3.4 kb cDNA which approximates the length of the mRNA detected by Northern blotting. The cyclin D-binding myb-like protein encoded by this clone is designated DMP1.

The DMP1 cDNA contains a long open reading frame that encodes a protein of 761 amino acids with a mass of 84,589 daltons (FIG. 1A), but its apparent molecular weight, based on its electrophoretic mobility on denaturing polyacrylamide gels, is significantly larger (see below). The initiation codon is the most 5' AUG in the nucleotide sequence and is preceded by 247 nucleotides that contain termination codons in all three reading frames. DMP1 contains three myb repeats (residues 224–392, underlined in FIG. 1A), connoting its role as a transcription factor (6,25,52). The clone recovered in the two-hybrid screen lacked the 5' untranslated region together with sequences encoding amino acids 1–175, which are replaced by the GAL4 activation domain. Both the amino terminal (residues 4–169) and carboxylterminal (residues 579–756) ends of the full length DMP1 protein are highly acidic. Fourteen SP and TP doublets are distributed throughout the protein, but none represent canonical proline-directed phosphorylation sites for cyclin-dependent kinases (SPXK/R). A typical nuclear localization signal is not identified.

Imperfect tandem myb repeats were first identified in the v-myb gene product of avian myeloblastosis virus and in its cellular proto-oncogene coded c-myb homologs (FIG. 1B). The prototypic repeat sequence contains three regularly spaced tryptophan residues separated by 18–19 amino acids, with the third tryptophan of a repeat separated by 12 amino acids from the first tryptophan of the next (3,17,25,45,49). Degenerate repeats that contain tyrosine in place of the third tryptophan or isoleucine in place of the first have been identified in other "myb-like" proteins (49). Authentic myb proteins bind to YAACNG (Y=pyrimidine) consensus sequences in DNA, with usually two or, rarely, only one of the myb repeats being sufficient to confer binding (6,16,40,41,52). Scattered amino acid identities enabled us to align the repeat sequences within mouse c-myb with those of DMP1 (FIG. 1B). In particular, there is an exact conservation of KQCR-W-N (SEQ ID NO:8) in repeat-2 (denoted by asterisks), which in c-myb contacts the DNA-binding site (42). However, the first repeat of DMP1 contains a tyrosine substituted for the first tryptophan and leucine for the third. Moreover, the second and third repeats, which in myb are each required for DNA binding, contain 11 and 6 residue insertions between the first and second tryptophans. These features distinguish the repeats of DMP1 from myb proteins and predicted that, if DMP1 binds DNA, its consensus binding site would likely differ from the myb recognition sequence.

Example 2

Interaction of DMP1 with D-type Cyclins

Because DMP1 interacted with cyclin D2 in yeast, the ability of a glutathione S-transferase (GST)-DMP1 fusion protein to bind D-type cyclins in vitro is examined. GST is fused to residues 176–761 of DMP1 (in lieu of GAL4 in the original cDNA clone), and the bacterially synthesized recombinant protein is incubated with [$^{35}$S]methionine-labeled D-type cyclins prepared by transcription and translation in vitro. As a positive control, GST-RB which can specifically bind D-type cyclins in this assay is used (15). Bound cyclins recovered on washed glutathione-Sepharose beads are analyzed by electrophoresis on denaturing gels. FIG. 2 (lanes 6 and 10) shows that cyclins D2 and D3 interact strongly with GST-RB in vitro (~20% of the total input protein is bound; see legend), whereas, as seen previously (15), cyclin D1 binds much less avidly (lane 2). GST-DMP1 is less efficient than GST-RB in binding cyclins D2 and D3 (~4-fold less binding), and under these conditions, an interaction with D1 is not detected (lanes 3, 7, 11). No labeled proteins bind to GST alone (lanes 4, 8, 12), and neither cyclin A nor cyclin E bind to GST-RB or to GST-DMP1. A cyclin D2 mutant disrupted in an amino-terminal Leu-X-Cys-X-Glu pentapeptide (SEQ ID NO:9) that is required for high efficiency GST-RB binding is not detectably compromised in its interaction with GST-DMP1 (negative data not shown); in agreement, DMP1 bears no homology to RB or to RB-related family members (p107 and p130).

Figure 3A:
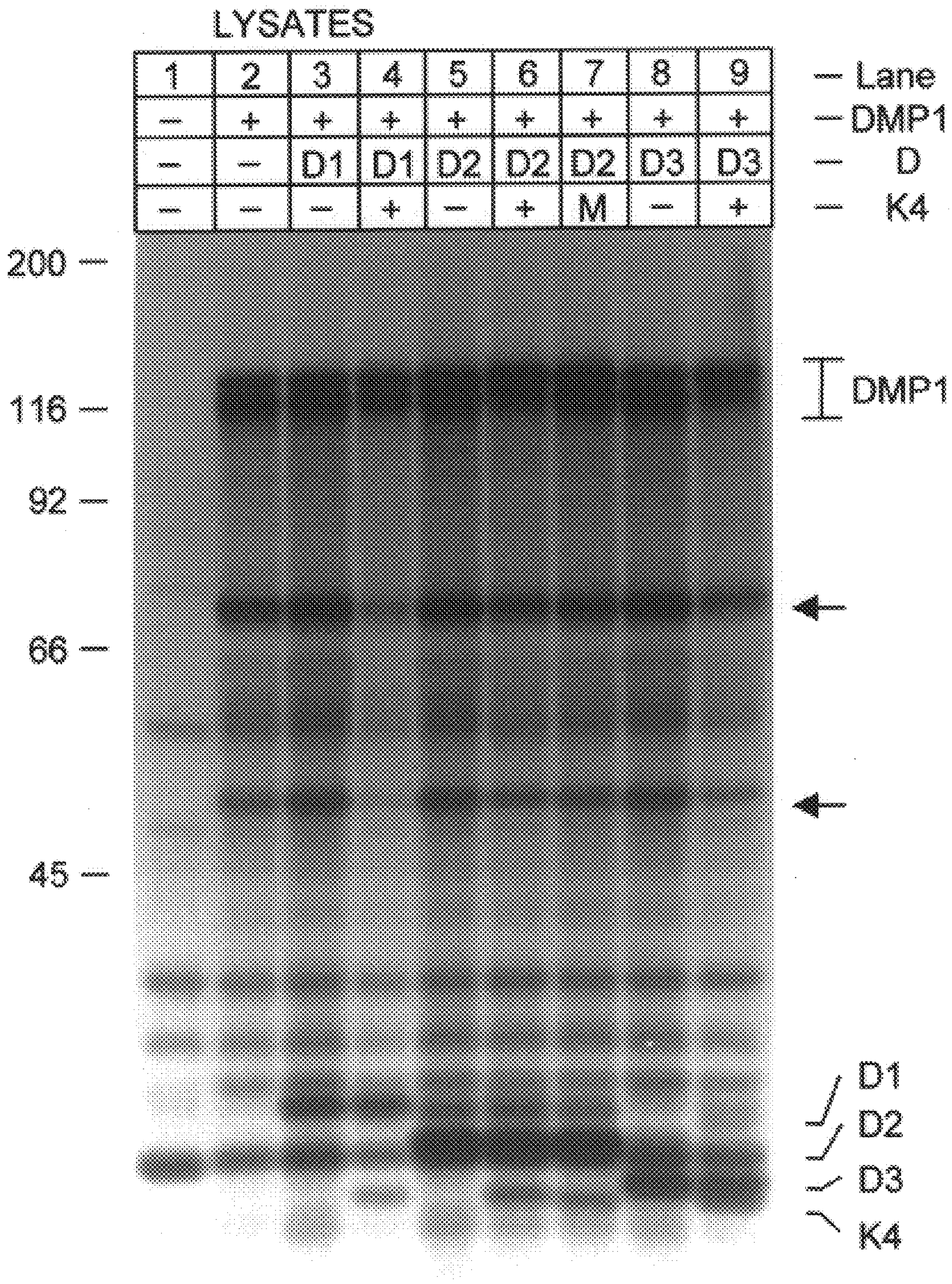
FIG. 3A displays a gel showing the binding of D-type cyclins to DMP1 in insect Sf9 cells. Insect cells coinfected with baculovirus vectors encoding DMP1, D-type cyclins (D1, D2, D3), wild-type CDK4 (K4), or a catalytically inactive CDK4 mutant (M) as indicated at the top of each panel of the figure are metabolically labeled with [$^{35}$S] methionine. Lysates are divided in half, and proteins in one aliquot are separated directly on denaturing gels.
Figure 3B:
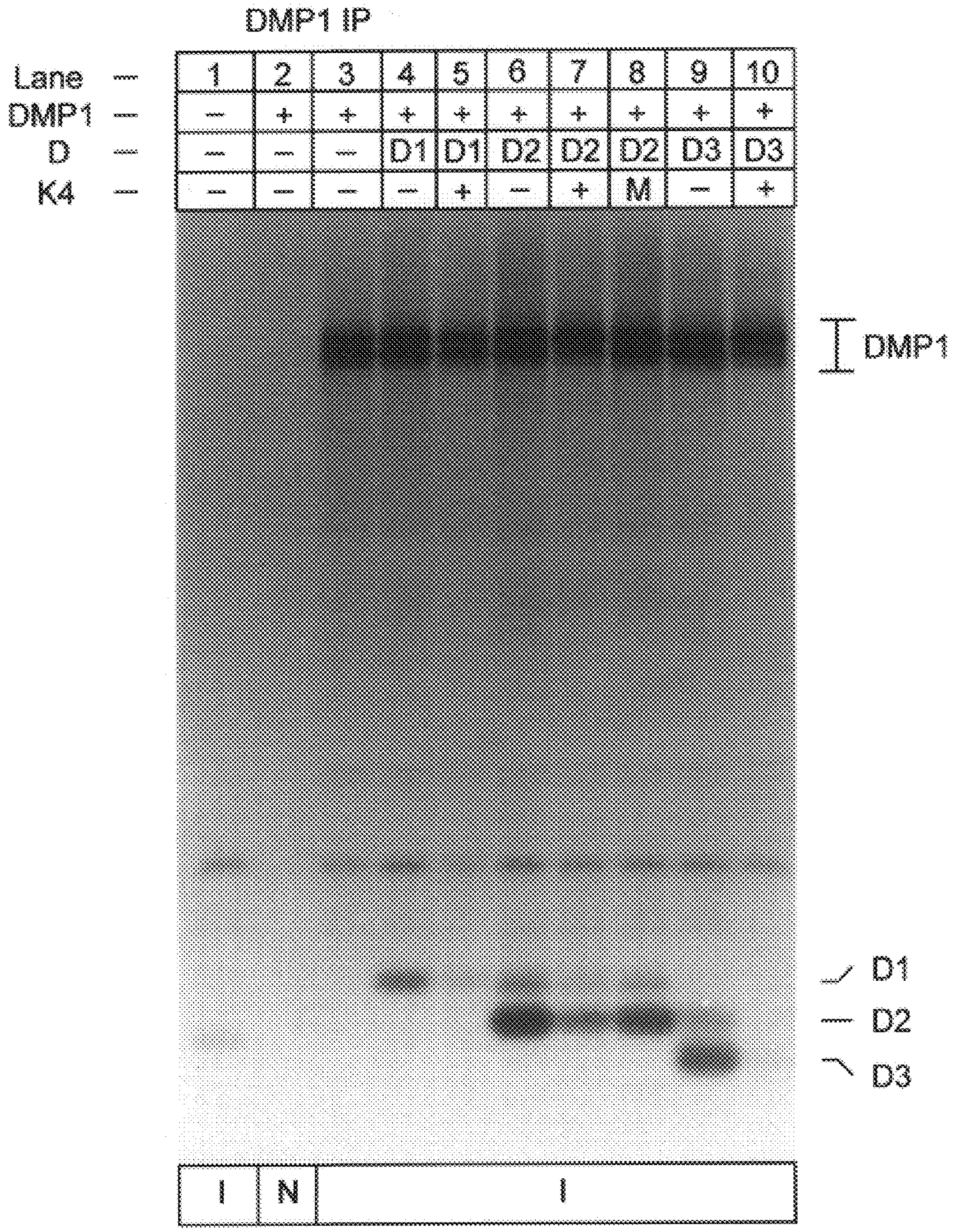
FIG. 3B shows the remaining proteins are precipitated with immune serum to the DMP1 C-terminus (denoted by I at the bottom of FIG. 3B) or with nonimmune serum (N), and the washed precipitates are electrophoretically separated in parallel. Positions of DMP1 isoforms, 78 and 54 kDa products (arrows, see text), D-type cyclins, and CDK4 are indicated at the right of each panel of the figure and those of molecular weight markers are shown at the left of FIG. 3A. Exposure times are 18 hours.

We next co-expressed full length DMP1 together with D-type cyclins under baculovirus vector control in insect Sf9 cells. After metabolically labeling infected cells with [$^{35}$S] methionine, we precipitated DMP1 with an antiserum directed to a peptide representing its nine C-terminal residues. Electrophoretic separation of unfractionated metabolically labeled lysates from infected cells enabled direct autoradiographic visualization and relative quantitation of the recombinant mouse proteins (FIG. 3A). Cells infected with a vector containing DMP1 cDNA (lane 2) produce a family of ~125 kDa proteins (brackets, right margin), as well as smaller species of ~78 and ~54 kDa (arrows, right margin), which are not synthesized in cells infected with a wild-type baculovirus (lane 1). The proteins in the 125 kDa range represented phosphorylated forms of DMP1 (see below) which are specifically precipitated with three different DMP1 antisera (FIG. 3B, lane 3, and see below) but not with nonimmune serum (lane 2). The 78 and 54 kDa species may represent C-terminally truncated DMP1 products arising from premature termination or proteolysis, because they were not precipitated with the antiserum to the DMP1 C-terminus (FIG. 3B). Apart from their phosphorylation, the full-length DMP1 proteins had apparent molecular masses significantly larger than that predicted from the cDNA sequence.

When DMP1 and different D-type cyclins are coexpressed in Sf9 cells (FIG. 3A, lanes 3, 5, and 8), anti-DMP1 coprecipitate cyclin D2 and D3 (FIG. 3B, lanes 6 and 9) and bring down cyclin D1 less efficiently (FIG. 3B, lane 4). Antisera to D-type cyclins reciprocally precipitate DMP1 (not shown). In analogous experiments using RB in place of DMP1, stronger binding is also observed using cyclin D2 or cyclin D3 versus cyclin D1 suggesting that differences in their binding efficiency may not be physiologic. Using coinfected cells containing approximately equivalent levels of DMP1 and cyclin D2 or cyclin D3, only 5–15% of the cyclin is stably bound to DMP1, whereas binding to RB in such experiments is ~1:1. Overall these results are completely consistent with the in vitro binding data obtained with DMP1 and RB (FIG. 2).

When Sf9 cells producing DMP1 are coinfected with baculoviruses encoding both a D-type cyclin and CDK4 (FIG. 3A, lanes 4, 6, and 9), complex formation between the cyclins and DMP1 is significantly diminished (FIG. 3B, lanes 5, 7, and 10). The latter effect could be due at least in part to competition between CDK4 and DMP1 for binding to cyclin. However, coproduction of a cyclin D-binding but catalytically inactive CDK4 mutant (FIG. 3A, lane 7) at levels equivalent to those of wild-type CDK4 (FIG. 3A, lane 6) is much less effective in preventing an interaction of DMP1 with cyclin D2 (FIG. 3B, lane 8 versus 7). Therefore, phosphorylation of DMP1 by cyclin D-CDK4 complexes (see below) might also inhibit DMP1 from binding to D-type cyclins. The fact that catalytically inactive CDK4 subunits do not enter into stable ternary complexes with cyclin D2-DMP1 (FIG. 3B, lane 8) also indicates that DMP1-bound cyclin D2 molecules are prevented from interacting as efficiently as unbound cyclin D2 with its catalytic partners.

Example 3

DMP1 is a Substrate for Cyclin D Dependent Kinases

Figure 4A:
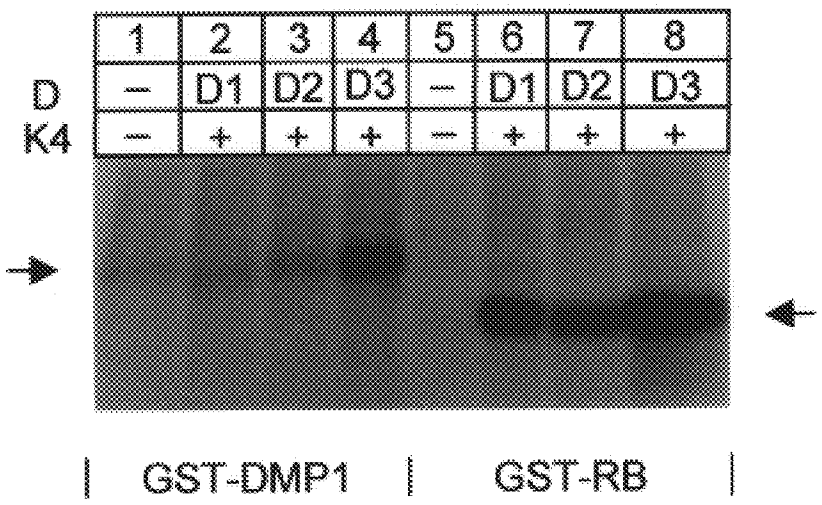
FIGS. 4A–4D are gels showing the phosphorylation of DMP1.

In comparison to many known CDKs, the cyclin D-dependent kinases exhibit an unusual preference for RB over histone H1 as an in vitro substrate (33,34,39). To test whether cyclin D-dependent kinases could phosphorylate DMP1, equivalent quantities of GST-DMP1 and GST-RB fusion proteins are compared for their ability to be phosphorylated in vitro by Sf9 lysates containing cyclin D-CDK4. Whereas lysates of Sf9 cells infected with control baculoviruses do not efficiently phosphorylate either fusion protein (FIG. 4A, lanes 1 and 5), lysates containing active cyclin D-CDK4 complexes phosphorylate both (FIG. 4A, lanes 2–4 and 6–8). Under equivalent conditions, GST-RB is always a preferred substrate (lanes 6–8), and different preparations of cyclin D3-CDK4 are routinely more active than D2- or D1-containing holoenzymes in phosphorylating DMP1 (lanes 2–4). Similar results are obtained when immunoprecipitated cyclin D-CDK4 or D-CDK6 complexes are used in lieu of Sf9 extracts as sources of enzyme.

Figure 4B:
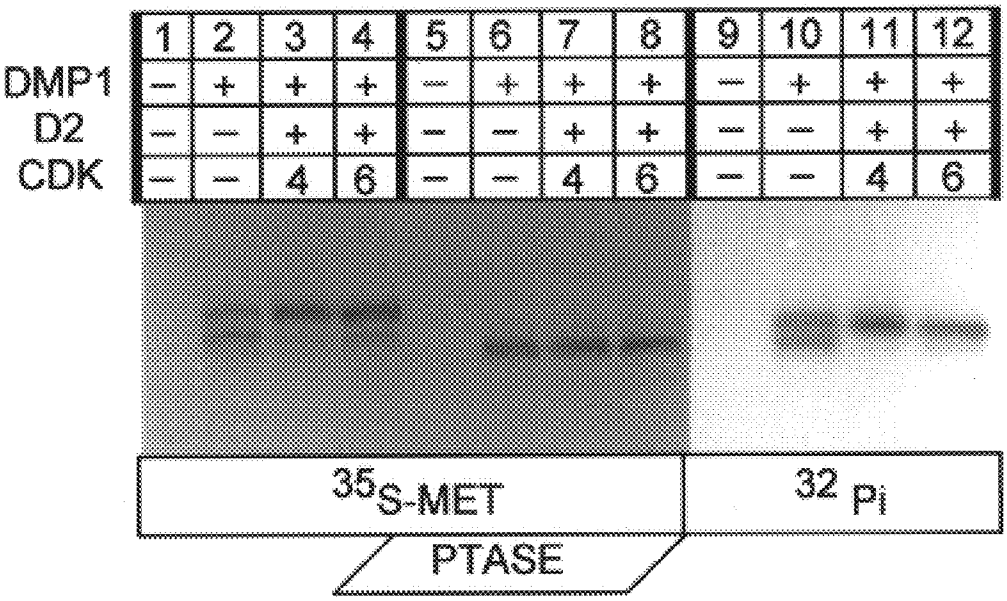

Based on data suggesting that DMP1 is post-translationally modified when expressed in Sf9 cells and that coexpression of cyclin D-dependent kinases could reduce its binding to D cyclins (FIG. 3), we expressed DMP1 in Sf9 cells alone or together with cyclin D2-CDK4 or cyclin D2-CDK6. Infected cells are metabolically labeled with [$^{35}$S]methionine, and DMP1 is immunoprecipitated from cell lysates and resolved on denaturing gels. Using less radioactive precursor than for the experiments shown in FIG. 3, DMP1 is more easily resolved into two major species (FIG. 4B, lane 2). No protein is precipitated from cells infected with a control baculovirus (lane 1). Coinfection of cells producing DMP1 with cyclin D2-CDK4 or cyclin D2-CDK6 results in conversion of the faster migrating DMP1 species to the slower mobility form (lanes 3, 4), whereas treatment of DMP1 immunoprecipitates with alkaline phosphatase converts both species to a single, more rapidly migrating band (lanes 7, 8). Similar data are obtained when infected cells are labeled with [$^{32}$P]orthophosphate instead of [$^{35}$S]methionine (FIG. 4B, lanes 9–12). Additional control experiments performed with the [$^{32}$P] phosphate-labeled proteins confirm that the observed effects of alkaline phosphatase on DMP1 mobility are due to removal of phosphate groups and are blocked by 1 mM sodium orthovanadate. Moreover, two dimensional separation of radiolabeled DMP1 tryptic phosphopeptides reveal complex fingerprint patterns, consistent with multiple phosphorylation sites (data not shown). Therefore, both components of the DMP1 doublet are phosphoproteins. Its basal phosphorylation can be mediated by endogenous kinases present in insect cells, but co-expression of cyclin D-dependent kinases augments accumulation of the hyperphosphorylated, more slowly migrating species.

Figure 4C:
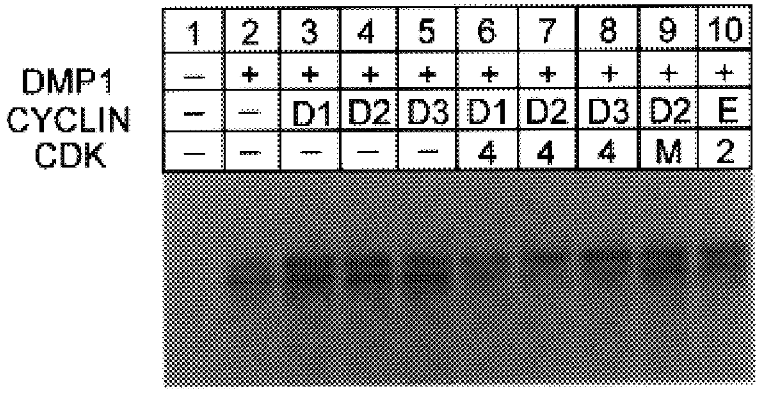
Figure 4D:
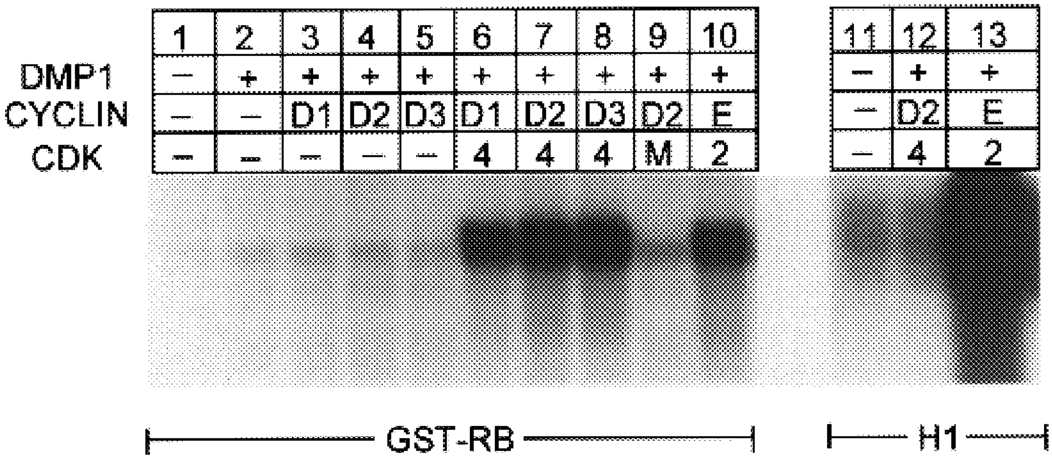

Hyperphosphorylation of DMP1 is not observed following infection of the cells with vectors producing D-type cyclin regulatory subunits alone (FIG. 4C, lanes 3–5). The process depends on a functional catalytic subunit (lanes 6–8 versus 3–5), and it is unaffected by a catalytically inactive CDK4 mutant (lane 9). Perhaps surprisingly, DMP1 hyperphosphorylation is not as readily induced by cyclin E-CDK2 (FIG. 4C, lane 10). Kinase assays performed with the same lysates (FIG. 4D) confirm that the cyclin D-CDK4 complexes are highly active as RB kinases (FIG. 4D, lanes 6–8), whereas mutant CDK4 is defective (lane 9). Despite its relative inactivity on DMP1 (FIG. 4C, lane 10), cyclin E-CDK2 readily phosphorylates both RB (FIG. 4D, lane 10) and histone H1 (lane 13), but cyclin D2-CDK4 fails to phosphorylate the latter (lane 12). Thus, cyclin D-CDK4 and cyclin E-CDK2 differ in their relative substrate specificities for both histone H1 and DMP1.

Example 4

Recombinant DMP1 Binds to Specific DNA Sequences

To determine whether DMP1 would bind specifically to DNA, 30 base-pair random oligonucleotides flanked by PCR primers are prepared and then incubated with Sf9 cell lysates containing the full length DMP1 protein. Oligonucleotides bound to washed DMP1 immunoprecipitates are amplified by PCR, and after six rounds of reprecipitation and reamplification, the final products are recloned and their sequences determined. From 27 sets of sequences, the consensus CCCG(G/T)ATGT is derived (FIG. 5A). Repeating the experiment with a histidine-tagged DMP1 polypeptide produced in bacteria in place of the baculovirus-coded protein, oligonucleotides containing GGATG are again isolated, but the preference for the 5' CCC triplet is less pronounced. Computer searches indicate that the DMP1 oligonucleotide consensus also represents a binding site for the Ets1 and Ets2 transcription factors [namely, (G/C)(A/C) GGA(A/T)G(T/C)]. All Ets family proteins bind to sequences with a GGA core, with their individual binding specificities determined by adjacent flanking sequences (31, 50). Because the selected DMP1 binding site included either GGA or, less frequently, GTA in the corresponding position (FIG. 5A), two oligonucleotides are synthesized (designated BS1 and BS2 in FIG. 5B) that differ only in this manner. Four mutant oligonucleotides are prepared (M1–M4 in FIG. 5B), at least one of which (M1) is predicted to bind neither DMP1 nor Ets proteins, and another (M3) that, in contradistinction to BS2, should interact with Ets1 or Ets2 but not DMP1.

Figure 6A:
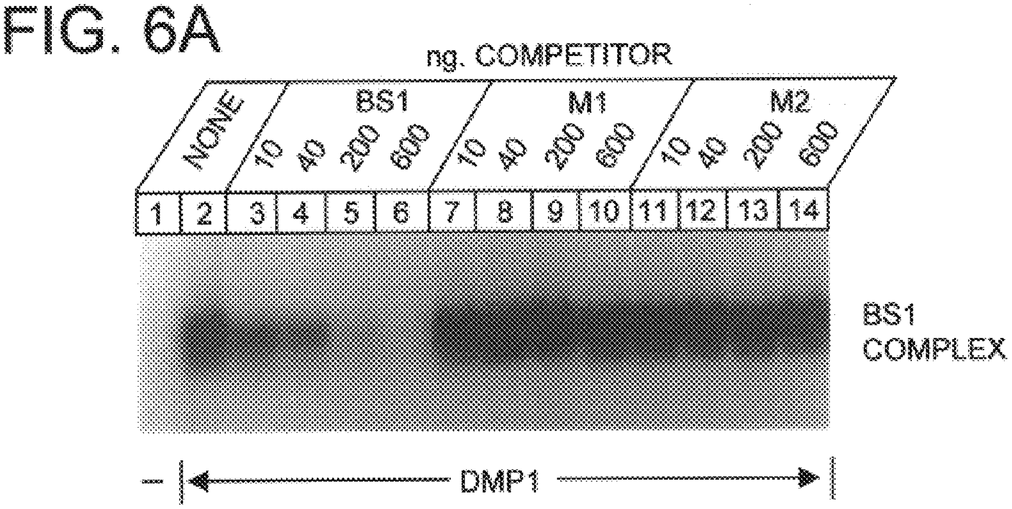
FIGS. 6A–6C show the oligonucleotide binding specificity of recombinant DMP1 and ETS2 proteins.
Figure 6B:
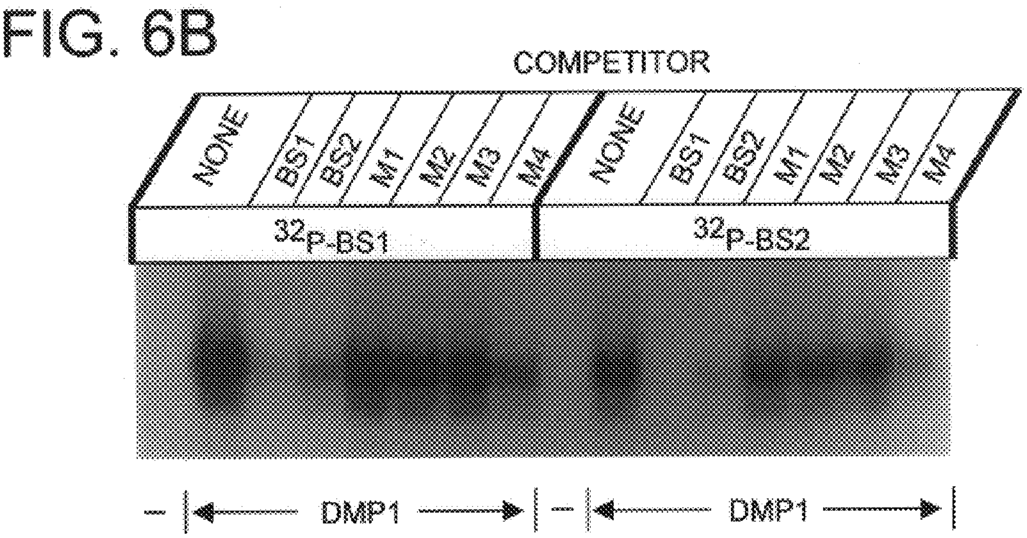
Figure 6C:
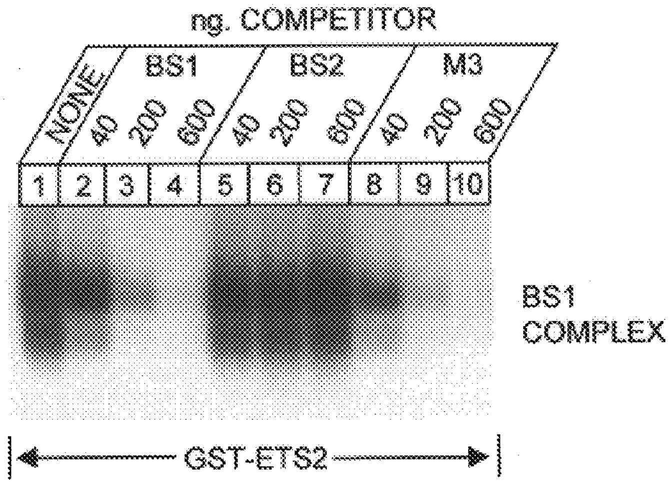

Using electrophoretic mobility shift assays (EMSA) performed after mixing a titrated excess (3 ng) of $^{32}P$-end labeled BS1 probe with Sf9 lysates producing DMP1 (~4 ng recombinant protein per reaction), a BS1-containing protein complex is detected that was competed with an excess of unlabeled BS1 oligonucleotide but not with mutant oligonucleotides M1 and M2 (FIG. 6A). Because M1 is disrupted in three of three completely conserved residues (FIG. 5B), its failure to compete is not surprising, but the inability of M2 to compete indicates that CCC sequences 5' of the G(G/T)A core are also important for DMP1 binding. More subtle mutations within this region may be tolerated, because high concentrations of M4 competed for BS1 binding to both Ets2 and DMPl in subsequent studies (FIG. 5B and see below). DMP1 also binds a BS2 probe, and the binding is competed by excess BS2 or BS1 (FIG. 6B). In agreement with the site selection frequencies (FIG. 5A), binding of $^{32}P$-BS1 under equivalent conditions was competed more efficiently by excess unlabeled BS1 than by BS2 (FIG. 6B). M3, which is predicted to interact only with Ets proteins, does not compete with BS1 or BS2 probes for binding to DMP1 (FIG. 6B). In contrast, a bacterially produced GST-Ets2 fusion protein does not bind detectably to a labeled BS2 oligonucleotide (not shown) under conditions where BS1 binding was readily detected (FIG. 6C). In agreement, Ets2 binding to BS1 could be competed with excess unlabeled BS1 and M3, but not by BS2 (FIG. 6C). Therefore, although both DMP1 and Ets2 can each bind to BS1 sequences, their exclusive interactions with BS2 and M3, respectively, help to distinguish DMP1 and Ets binding activities (summarized in FIG. 5B).

Under identical EMSA conditions, use of extracts from Sf9 cells coexpressing cyclin D-CDK4 complexes (and containing predominantly hyperphosphorylated forms of DMP1) do not affect the efficiencies or patterns of DMP1 binding to radiolabeled BS1 or BS2 probes. Nor are there apparent differences in the recovery of DMP1-probe complexes between lysates lacking or containing cyclin D. Although as much as 15% of DMP1 molecules form stable complexes with D-type cyclins when the two are coexpressed (FIG. 3), both polyvalent and monoclonal antibodies to cyclin D are unable to supershift any of the DMP1-oligonucleotide complexes formed with the same Sf9 extracts, indicating that the interaction of DMP1 with cyclin D might inhibit DNA binding.

Example 5

DMP1 Expression and DNA Binding Activity in Mammalian Cells

Figure 8A:
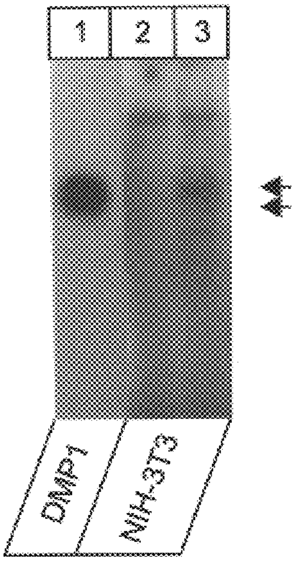
FIGS. 8A–8C are gels showing the expression of DMP1 in mammalian cells.

Using antisera directed either against a DMP1 C-terminal peptide (serum AF, FIGS. 3 and 4), the GST-DMP1 fusion protein (serum AH, residues 176–761), or its putative DNA-binding domain (serum AJ, residues 221–439), DMP1 is not detected in mammalian cells by immnunoprecipitation of the protein from metabolically labeled cell lysates. However, sequential immunoprecipitation (with serum AJ) and immunoblotting (with sera AJ plus AH) reveals low levels of DMP1 in lysates of proliferating NIH-3T3 fibroblasts (FIG. 8A, lane 3). Most of the protein has a mobility corresponding to that of the hyperphosphorylated form synthesized in Sf9 cells (lane 1). [The baculovirus-coded protein was separated on the same gel as the immunoprecipitates from NIH-3T3 cells, and their positions were aligned after multiple autoradiographic exposures].

Figure 7A:
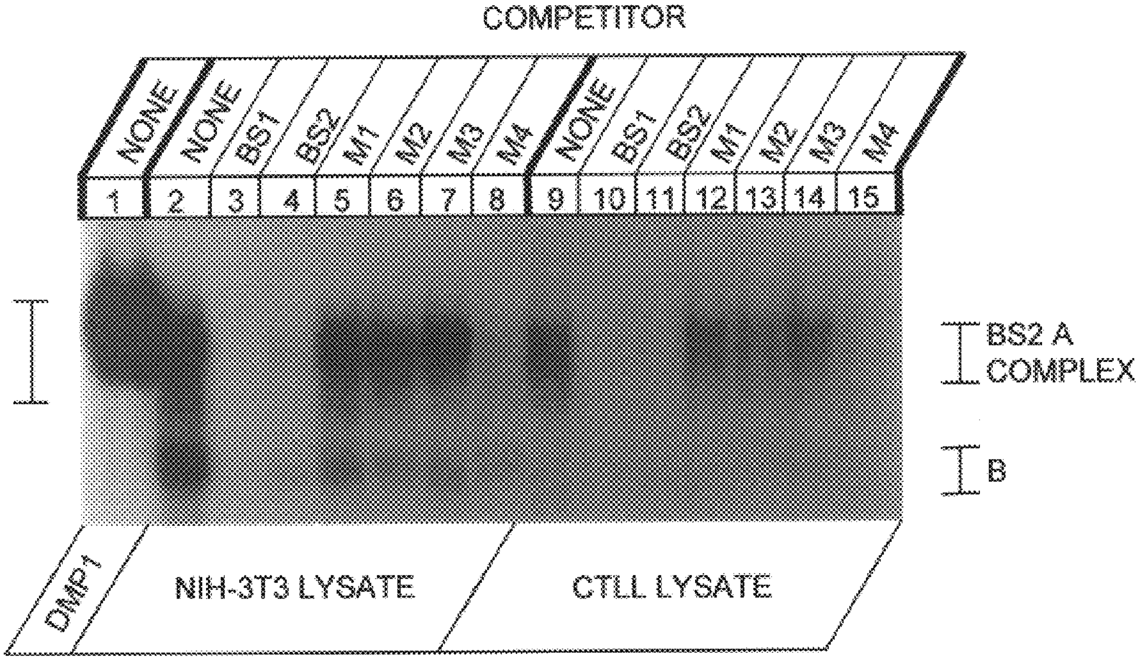
FIGS. 7A–7B are gels showing the binding of radiolabeled BS2 and BS1 oligonucleotides to proteins in mammalian cells. Lysates of Sf9 cells containing recombinant DMP1 (lanes 1), mouse NIH-3T3 fibroblasts (lanes 2–8), or mouse CTLL lymphocytes (lanes 9–15) are incubated with radiolabeled BS2 (FIG. 7A.) or BS1 (FIG. 7B) probes, either in the absence (lanes 2 and 9) or presence (other lanes) of the indicated competing oligonucleotides (600 ng). Two distinct BS2-containing complexes (labeled A-complex and B-complex at the right of FIG. 7A.) are detected, only the first of which corresponds in mobility to that formed with recombinant DMP1 (lane 1). Autoradiographic exposure times are 18 hours for FIG. 7A and 6 hours for FIG. 7B.
Figure 7B:
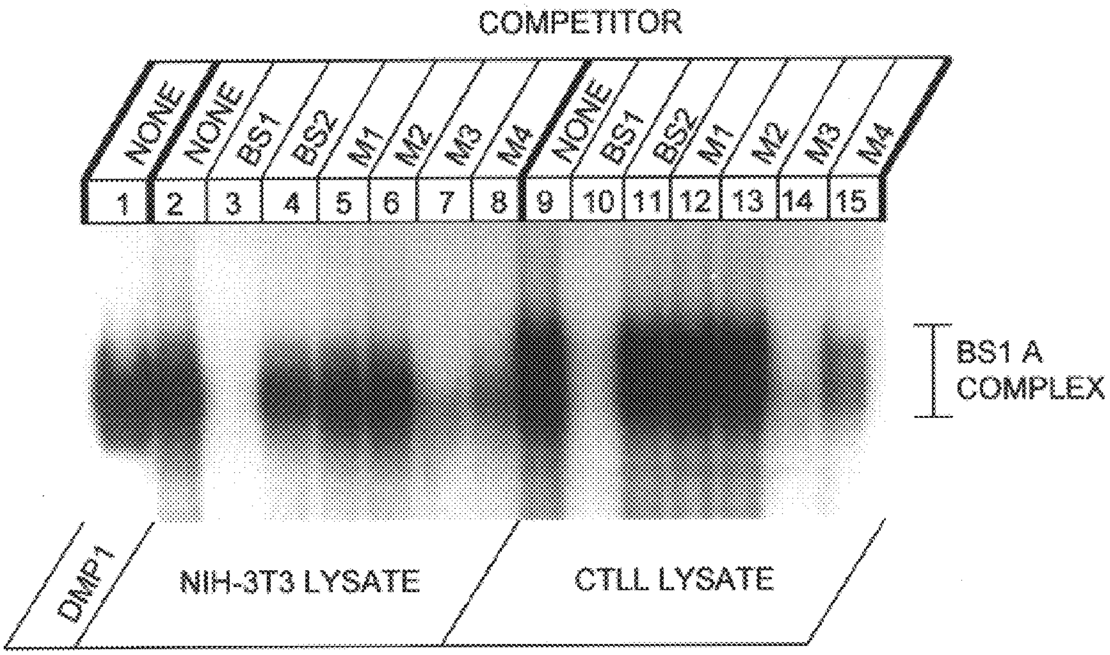

Using the non-Ets-interacting $^{32}P$-labeled BS2 probe to screen for DNA binding activity in mammalian cells by EMSA, complexes with mobility indistinguishable from that generated with the recombinant protein in Sf9 lysates (FIG. 7A, lane 1, complex A) are detected with lysates from NIH-3T3 fibroblasts (lanes 2–8) and CTLL T cells (lanes 9–15). A faster migrating complex which lacks DMP1 is also seen (complex B, see below). As predicted, A-complexes containing bound 32P-BS2 are competed by both unlabeled BS1 (lanes 3, 10) and BS2 (lanes 4, 11), but not by the M3 Ets-specific recognition sequence (lanes 7, 14). Using the same lysates, more total binding activity is detected with a BS1 probe (FIG. 7B; compare autoradiographic exposure times for panels A and B), the vast majority of which is competed by M3 (lanes 7, 14) but not by BS2 (lanes 4, 11). Therefore, the EMSAs performed with $^{32}P$-BS1 primarily detect Ets-type DNA binding activity, whereas that performed with $^{32}P$-BS2 scores an activity indistinguishable from that of bona fide DMP1.

Figure 8B:
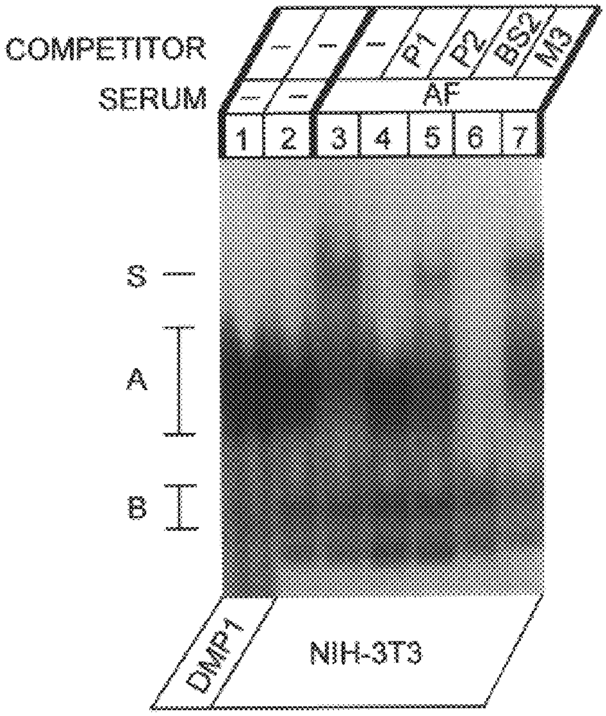
Figure 8C:
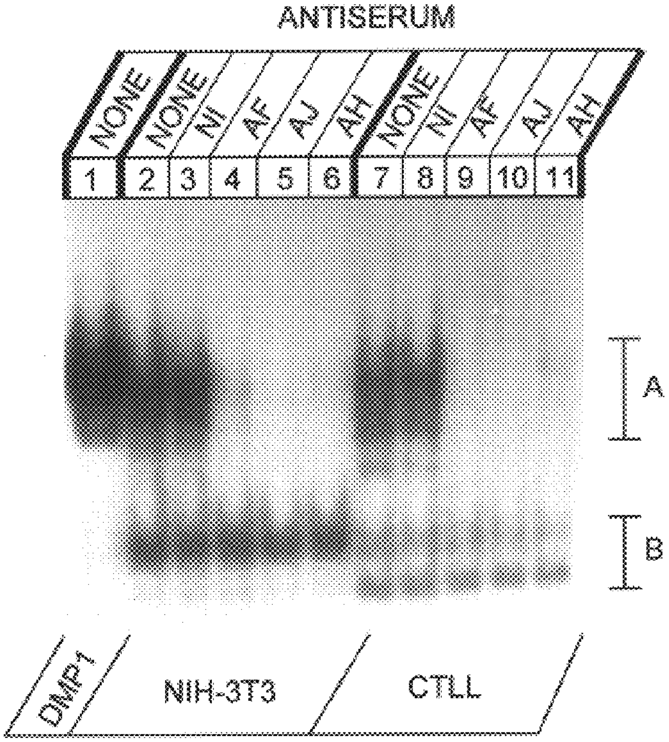

To confirm that DMP1 activity is responsible for the A-complexes observed in EMSAs done with the BS2 probe, antiserum to the DMP1 C-terminus (AF) is added to the binding reactions (FIG. 8B). This generates a “supershifted” complex of slower mobility (labeled S, lane 3) which is eliminated by competition with the cognate DMP1 peptide (P1, lane 4) but not with an unrelated control peptide (P2, lane 5). Formation of the A and S complexes is blocked by competition with the unlabeled BS2 oligonucleotide but not with M3, whereas B complexes remain and must therefore contain a protein(s) other than DMP1 or Ets1/Ets2. Consistent with these findings, preincubation of NIH-3T3 or CTLL extracts with any of three different antisera to DMP1 (AF, AJ, or AH) but not with nonimmune serum (NI) eliminates the formation of A, but not B, complexes in EMSAs (FIG. 8C). Therefore, the BS2-containing A-complex formed with extracts of mammalian cells contained authentic DMP1.

Example 6

DMP1 Can Activate Transcription

Figure 9A:
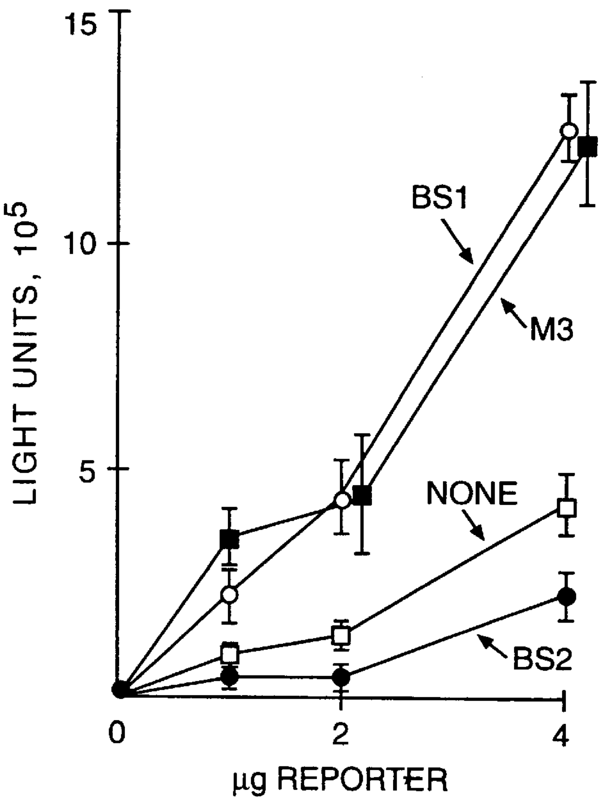
FIGS. 9A–9C are graphs showing the transactivation of reporter plasmids in 293T cells transfected with recombinant DMP1.
Figure 9B:
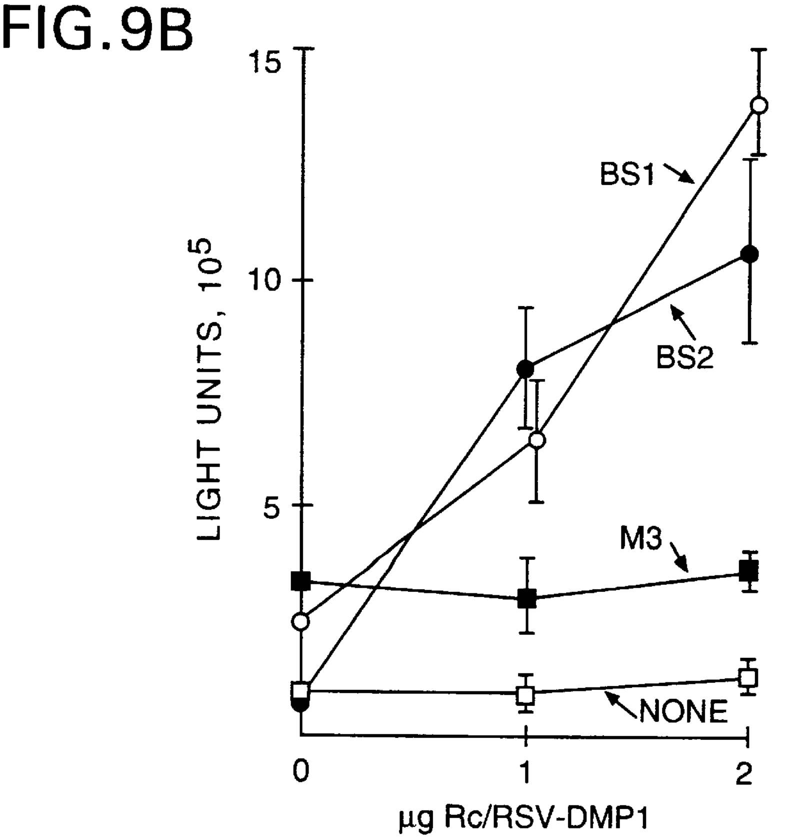
Figure 9C:
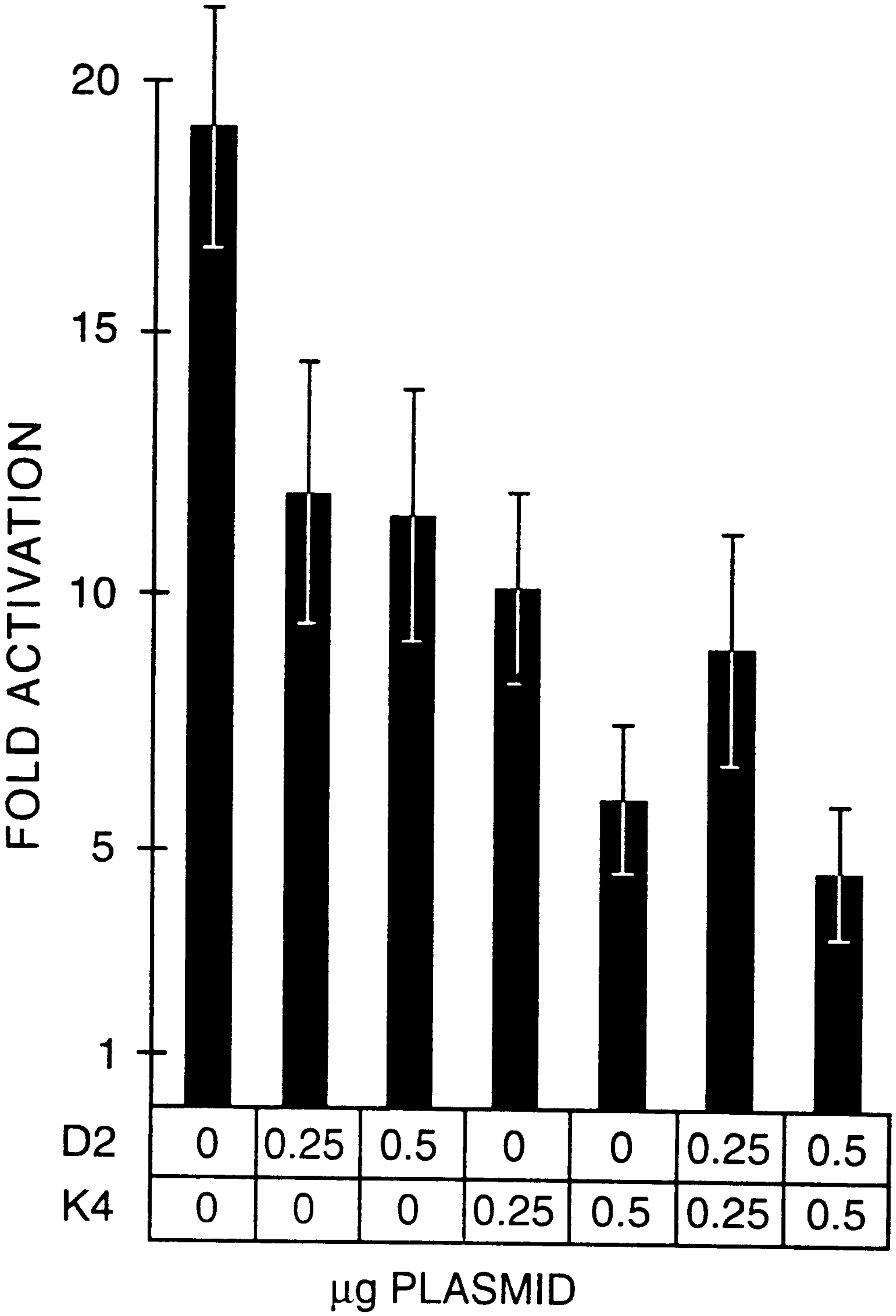

To determine if DMP1 has the capacity to activate transcription, tandem BS1, BS2, or M3 consensus sites are inserted 5' to an SV40 minimal promoter and these control elements are fused to a luciferase reporter gene. Reporter plasmids containing either BS1 or M3 binding sites are themselves highly active in a dose-dependent fashion when transfected into 293T kidney cells, likely due to expression of endogenous Ets factors, but the reporter plasmid containing BS2 sites generates even less “background” activity than one containing only a minimal SV40 promoter (FIG. 9A). When the cDNA encoding DMP1 is cloned into a pRc/RSV mammalian expression plasmid and cotransfected with limiting amounts (1 $\mu$g) of the BS2-driven reporter plasmid into 293T cells, significant transactivation of luciferase activity at levels ~20-fold that seen with the BS2 reporter plasmid alone are observed (FIG. 9B). A 7-fold activation of the BS1-driven reporter in response to DMP1 (FIG. 9B) is of even greater absolute magnitude but is initiated from a 4–5 fold higher basal level (FIGS. 9A and 9B). In contrast, using promoters lacking BS2 sites or containing Ets-specific M3 sites, transactivation by DMP1 is not observed. Gross overexpression of DMP1 in these experiments is documented by immunoprecipitation and immunoblotting, and the majority of the ectopically produced protein is localized to the cell nucleus (data not shown).

Ets family transcription factors including Ets1 and Ets2 can also bind to and activate transcription from those DMP1 consensus recognition sites that contain a GGA core. Promoter-reporter plasmids containing consensus binding sites with either a central GGA or GTA trinucleotide could each respond to overexpressed, recombinant DMP1 in transactivation assays. However, in the absence of ectopically expressed DMP1, "background" levels of reporter gene activity are significantly higher using the Ets-responsive promoters implying that endogenous Ets activity greatly exceeds that of endogenous DMP1 in the cells tested. Similarly, when the GGA-containing consensus oligonucleotide probe is used for EMSA, competition studies indicate that Ets family members predominate in complexes resolved from lysates of NIH-3T3 and CTLL cells.

Complexes formed with the GTA-containing BS2 probe could be depleted or supershifted with antisera to DMP1 and are not competed by unlabeled Ets-binding M3 oligonucleotide (FIG. 8), whereas those formed with the GGA-containing BS1 probe are resistant to these treatments (negative data not shown). Particularly in cases such as these where total Ets binding activity greatly exceeds that of DMP1, the use of oligonucleotide probes containing the GTA core is essential for unambiguously demonstrating endogenous DMP1 DNA binding activity by EMSA.

DMP1 not only specifically interacts with cyclin D2 when overexpressed in yeast cells, but translated, radiolabeled D-type cyclins bind directly to GST-DMP1 fusion proteins in vitro, and complexes between full-length DMP1 and D-type cyclins readily form in intact Sf9 insect cells engineered to co-express both proteins under baculovirus vector control. DMP1 undergoes basal phosphorylation when synthesized in Sf9 cells and is further hyperphosphorylated in cells co-expressing catalytically active, but not mutant, cyclin D-CDK4 complexes. Immune complexes containing cyclin D-CDK4 can also hyperphosphorylate DMP1 in vitro. However, other kinases also contribute to DMP1 phosphorylation in insect cells, given the accumulation of multiply phosphorylated forms of the protein even in cells not engineered to co-express recombinant cyclin-CDK complexes.

The observed interactions of DMP1 and D-type cyclins show some analogy with those previously observed with RB. However, there are many important differences. First, side by side comparisons indicate that D-type cyclins bind less avidly to DMP1 than to RB, both in vitro and in Sf9 cells. Second, the efficiency of RB binding to D-type cyclins is influenced by a Leu-X-Cys-X-Glu pentapeptide sequence (SEQ ID NO:9) that D-type cyclins share with certain RB-binding oncoproteins, whereas a cyclin D2 mutant containing substitutions in this region remained able to interact with DMP1. Third, RB is phosphorylated to a much higher stoichiometry than DMP1 by cyclin D-CDK4 complexes. CDK4-mediated phosphorylation of RB in vitro or in Sf9 cells can occur at multiple canonical CDK sites. However, even though there are fourteen Ser-Pro and Thr-Pro doublets distributed throughout the DMP1 protein, none of these represents a typical CDK consensus sequence, suggesting that cyclin D-dependent kinases phosphorylate atypical recognition sequences in this protein. Conversely, cyclin E-CDK2 complexes phosphorylated DMP1 poorly, if at all, and no physical interactions between DMP1 and cyclin E or cyclin A are detected. Finally, phosphorylation of RB by cyclin D-CDK4 complexes cancels its ability to bind D-type cyclins, so that in coinfected Sf9 cells, stable ternary complexes could only be generated between RB, D-type cyclin, and catalytically inactive CDK4 subunits. However, catalytically inactive CDK4 could not enter into stable ternary complexes with DMP1 and cyclin D. This again indicates that cyclin D contacts DMP1 and RB via different residues (see above), and raises the possibility that DMP1 and CDK4 interact with overlapping binding sites on cyclin D, being able to compete with one another for cyclin D binding. In agreement, introduction of catalytically inactive CDK4 into cells expressing both cyclin D2 and DMP1 modestly reduce the extent of D2 binding to DMP1, although to a far lesser extent than wild-type CDK4. Therefore, although hyperphosphorylation of DMP1 can decrease its ability to bind cyclin D, the role of cyclin D binding is not solely to trigger CDK4-mediated phosphorylation.

Together, these findings provide evidence that cyclin D influences gene expression via its binding and/or phosphorylation of DMP1. Enforced transient expression of cyclin D2 or D2-CDK4 in mammalian cells negatively regulates the ability of DMP1 to transactivate reporter gene expression although the mechanistic basis remains unresolved. This effect of cyclin D is observed with or without addition of exogenous catalytic subunits, but endogenous CDK4 activity can already be significantly activated via cyclin D overexpression alone, while even higher levels of CDK4 activity are likely to be toxic. Enforced expression of cyclin D-CDK4 neither influences the stability of overexpressed DMP1 nor its ability to preferentially localize to the nucleus of transfected mammalian cells. Coexpression of cyclin D or cyclin D-CDK4 together with DMP1 in Sf9 cells also had no apparent effect on the ability of DMP1 to form EMSA complexes with consensus oligonucleotide probes. However, the majority of DMP1 molecules in such extracts do not contain stably bound cyclin, and their extent and sites of phosphorylation are unknown. Oligonucleotide-bound proteins from such extracts or from mammalian cells could be supershifted in EMSAs performed with antisera to DMP1, but polyvalent antisera or monoclonal antibodies to D cyclins are without detectable effect on their electrophoretic mobility, indicating that cyclin D binding and/or cyclin D-CDK4 mediated phosphorylation interferes with the ability of DMP1 to bind to DNA. Direct effects on transactivation potential are similarly plausible. In the case where cyclin D regulates DMP1 activity in vivo, DMP1 functions better in quiescent cells lacking cyclin D expression than in proliferating cells. These observations underscore a role for D-type cyclins in the control of gene expression in an RB-independent fashion.

Example 7

Functional Analysis of DMP1 Domains

Introduction

The ability of DMP1 to act as a transcription factor correlates with its ability to regulate cell growth. Both reporter gene activity and growth arrest depend upon the ability of DMP1 to bind to specific DNA sequences and to activate transcription when so bound. Cyclin D overrides the ability of DMP1 to regulate transcription of its target genes and to induce growth arrest. This indicates that specific peptide domains of DMP1 can act as antagonists of target gene activation or cyclin D mediated regulation. A series of experiments are described which define three specific functional domains of DMP1.

Results

A series of deletion mutants and a point mutant of DMP1, K319E, (in which the lysine at position 319 of SEQ ID NO:1 is replaced by a glutamic acid) were prepared and used to determine the DNA-binding domain of DMP1 by electrophoretic mobility shift assay (EMSA) using a $^{32}P$ labeled BS2 probe. The DNA-binding domain of DMP1 was mapped to a central region containing the three MYB repeats plus adjacent flanking sequences: a BstEII to NcoI fragment encoding amino acids 87–458 of SEQ ID NO:1 (Table 1). This region alone was necessary and sufficient for DNA binding. Notably, the K319E point mutation, which converts a positive charge to a negative charge in the middle of the DNA-binding domain has a markedly diminished affinity (i.e., about 2% of the wildtype) for the DNA probe.

TABLE 1

An EMSA assay with the $^{32}P$-BS2 Probe for transfection lysates of NIH-3T3 fibroblasts having expression vectors encoding murine wild-type DMP1, corresponding deletion mutations, or a point mutation of DMP1 (K319E). The EMSA assay was performed as described above, with and without a 100-fold excess of cold BS2 probe. All $^{32}P$ labeled bands were blocked by the addition of the cold BS2 probe.

| Transfection Product | TYPE | Amino Acids of SEQ ID NO: 1 | $^{32}P$-labeled Band |
|---|---|---|---|
| None | None | None | No |
| DMP1 | wildtype | 1–761 | Yes |
| M1 | EcoNI | 1–661 | Yes |
| M2 | StuI | 1–520 | Yes |
| M3 | NcoI | 1–458 | Yes |
| M4 | BstBI | 1–380 | No |
| M5 | XbaI and BstEII | 87–761 | Yes |
| M6 | BstII and Eco47-3 | 1–86; 170–761 | No |
| M7 | Eco47-3 and SacI | 1–169; 238–761 | No |
| M8 | SacI and BstBI | 1–237; 381–761 | No |
| M9 | 5' deletion | 234–761 | No |
| M10 | BstEII and NcoI | 87–458 | Yes |
| M11 | K319E | 1–318; E; 320–761 | Yes, but a very faint band |

Figure 10:
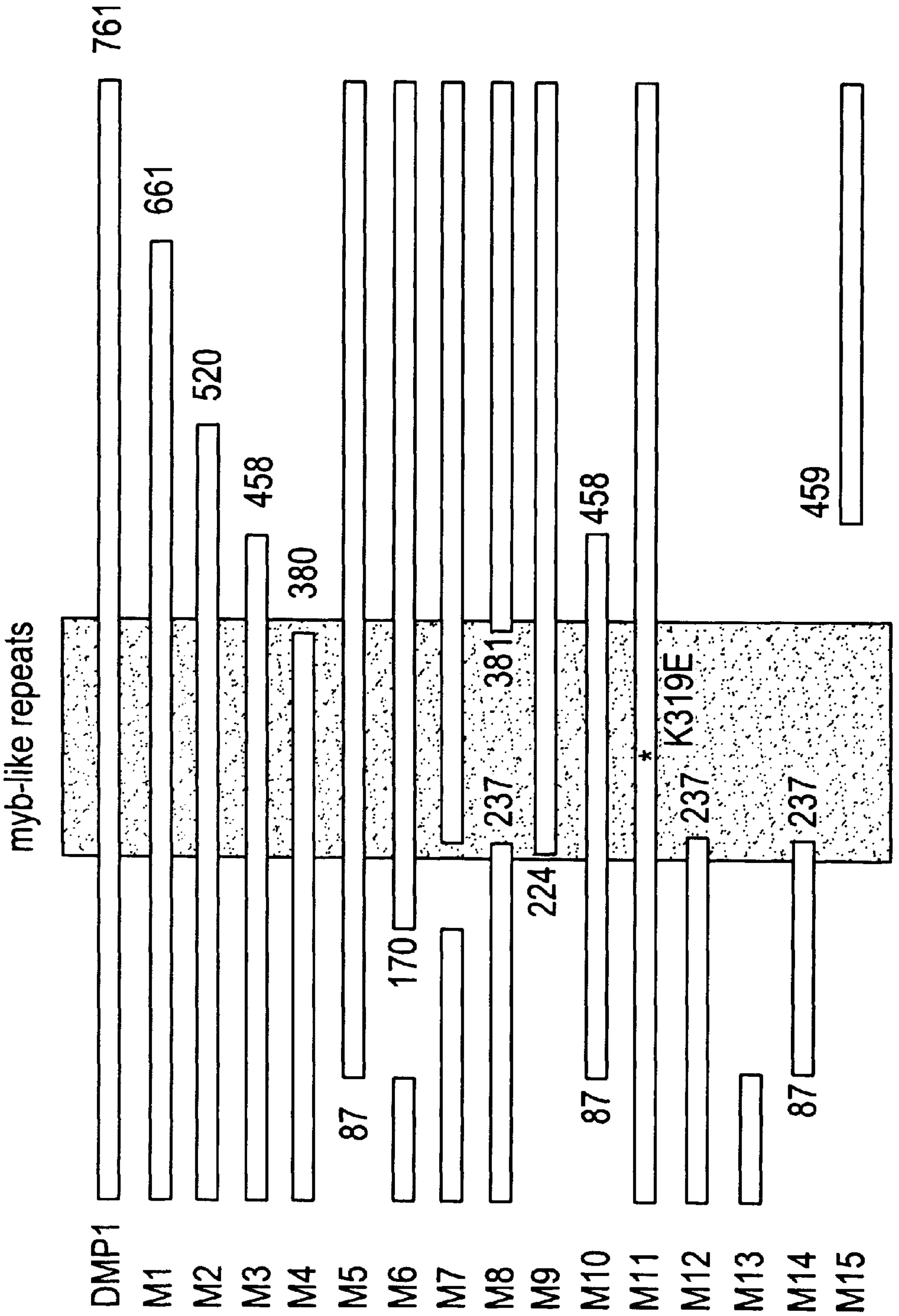
FIG. 10 shows a schematic representation of wild-type DMP1 (SEQ ID NO:1) and various mutants (M1–M15). All are deletion mutants except for M11, which contains a Glu for Lys substitution at codon 319 (K319E, asterisk) located within the second myb repeat. The numbers indicate the deletion boundaries, and the current central region containing the three tandem myb repeats is shaded.

Next, the series of DMP1 deletion mutants and the K319E point mutant were expressed in mammalian cells and in insect Sf9 cells (see FIG. 10, Table 1) to determine the DMP1 gene transactivation domain. Using a reporter gene (luciferase) programmed by an artificial DMP1-responsive promoter, sequences at the DMP1 carboxylterminus, namely amino acids 459 to 761 of SEQ ID NO:1 were shown to be necessary for gene transactivation (Table 2). Elimination of these sequences did not effect DNA binding in an EMSA assay (Table 1) but resulted in a dramatic reduction of reporter gene transcription (Table 2). The extreme N-terminal sequence of DMP1 can also contribute to transactivation (amino acids 1–86 of SEQ ID NO:1).

TABLE 2

The results of transfecting NIH-3T3 fibroblasts (10 ml cultures) with expression vectors (3 μg/10 ml) encoding murine wild-type DMP1, corresponding deletion mutations, or a point mutation of DMP1 (K319E). The effects were measured either by determining the expression of luciferase by a luciferase reporter plasmid under the control of a DMP1-responsive promoter (pGL2BS2, 8 μg/10 ml), or as the percent of cells that incorporate BrdU. Transactivation of luciferase reporter plasmids was normalized by arbitrarily setting the amount of luciferase activity determined in presence of an expression vector without an insert, to 1.0. Transfection efficiencies were normalized by the levels of secreted endocrine alkaline phosphatase assays. The cells were treated as described in Examples 7 and 8. The transfection products are as defined in FIG. 10, Table 1.

| Transfection Product | Luciferase Activity | % Cells BrdU Positive |
|---|---|---|
| None | 1.0 | 80 |
| DMP1 | 8.4 | 12 |
| M1 | 6.7 | 12 |
| M2 | 3.6 | 20 |
| M3 | 2.3 | 24 |
| M4 | 1.0 | 52 |
| M5 | 6.2 | 32 |
| M6 | 1.0 | 48 |
| M7 | 0.9 | 36 |
| M8 | 1.1 | 54 |
| M9 | 1.0 | 50 |
| M10 | 1.1 | 56 |
| M11 | 1.1 | 48 |

The series of DMP1 deletion mutants and the K319E point mutant were then used to determine the cyclin D binding domain of DMP1. Expression vectors encoding murine wild-type DMP1, the corresponding deletion mutations, or K319E (i. e., wildtype DMP1 and M1–M11, defined in FIG. 10, Table 1) were cotransfected with an expression vector encoding cyclin D1 into SF9 cells. Wild-type DMP1 and M1–M11 were expressed containing Flag-tags. SF9 lysates were immunoprecipitated with an antibody raised against the Flag-tag. The immunoprecipitates were resolved individually by gel electrophoresis, and then Western blotted with an antibody raised against cyclin D1. All of the samples, except M9, contained a band that corresponded to cyclin D1, indicating that the cyclin D1 was bound to all of the immunoprecipitated DMP1 mutants except M9. Therefore, the cyclin D1 binding domain is missing in the M9 deletion mutant. In addition, the M5 sample was particularly faint, indicating that a portion of the cyclin D1 binding domain also may be missing in this deletion mutant of DMP1. Therefore, deletion of the N-terminal domain of DMP1 (i.e., amino acids 1–223) abrogates its ability to interact with D-type cyclins, and thus, the region of DMP1 from residues 1–223 contains a specific cyclin D interaction motif required for D-type cyclin-DMP1 association.

Example 8

DMP1 Arrests Cell Cycle Progression in G1 Phase

Introduction

Expression of high concentrations of the transcription factor, DMP1, in NIH-3T3 fibroblasts is shown to arrest the cell cycle in G1 phase, and to prevent the proliferating cells from replicating their chromosomal DNA. The effect is dependent upon the ability of DMP1 to bind to cellular DNA, which indicates that genes negatively regulated by DMP1 play an important role in cell cycle progression. The coexpression of the growth promoting G1 cyclins D1, D2 or E can override the ability of DMP1 to induce G1 arrest.

Results

NIH-3T3 cells were placed on cover slides and transfected with the expression vectors (pFLEX-DMP1 or the corresponding vector containing the deletion or point mutants of mouse DMP1 plus or minus cyclin D or E) for fourteen hours. The cells were then washed twice and DMEM plus10% FCS was added and the cells incubated for eight hours. Half of the cells were starved by washing twice with 0.1% FCS, and then incubated for twenty-four hours in 0.1% FCS in DMEM. The remaining cells were not starved but were incubated for twenty-four hours in DMEM plus 10% FCS without washing. BrdU was added to both groups of cells and the cells were incubated for twenty-two hours in DMEM plus 10% FCS.

The cells were then restimulated to enter the cell cycle synchronously with DMEM plus 10% FCS. At the same time, 5'-Bromo-2' Deoxyuridine (BrdU) was added to the medium. The cells were fixed 22 hours later in methanol acetone (1:1) and stained for BrdU incorporation and DMP1 expression as described in the Materials and Methods.

Immunofluorescence showed that cells expressing DMP1 did not incorporate BrdU. Thus the nuclei of these cells were stained red, which indicates DMP1 has been expressed, or alternatively, green, which indicates BrdU incorporation has occurred (see MATERIALS and METHODS).

In contrast, cells expressing a DMP1 point mutant in place of DMP1 did not arrest cells in G1. The DMP1 point mutant, K319E, binds to DNA with a diminished affinity, if at all (Table 1). The cells expressing K319E DMP1 also incorporated BrdU thereby generating dual-labeled nuclei (red+green=yellow).

Furthermore, in nonstarved cells which were incubated in 10% FCS, 90% of the cells incorporated BrdU in the absence of DMP1 transfection, whereas only 30% of the cells incorporated BrdU when the cells were transfected with expression vectors containing DMP1. In the serum starved cells, 80% of the cells incorporated BrdU in the absence of DMP1 expression, whereas only 15% of the cells incorporated BrdU. Co-transfection of cells with expression vectors containing DMP1 and cyclins D2, or E hindered the ability of DMP1 to induce cell cycle arrest, thereby overriding the inhibition of BrdU incorporation due to DMP1 (Table 3). Thus, DMP1 blocks BrdU incorporation less efficiently in the presence of 10% FCS than in serum starved cells.

The series of DMP1 deletion mutants and the K319E point mutant were found to also effect the percentage of cells that incorporated BrdU, though generally to a lesser extent than wildtype DMP1 (Tables 2 and 3). Notably, however, M1 had an equivalent effect on BrdU incorporation as the wildtype DMP1.

TABLE 3

The results of transfecting NIH-3T3 fibroblasts with expression vectors encoding murine wild-type DMP1, DMP1 deletion mutants, or the point mutation K319E, on the percentage of cells that incorporate BrdU. Starved (0.1% FCS) or nonstarved (10% FCS) cells were labeled for 22 hours. M6, M8, and M11 are defined in FIG. 10, Table 1.

| Transfection | | % Cells BrdU Positive | |
|---|---|---|---|
| Product | Additive | in 0.1% FCS | in 10% FCS |
| None | None | 80 | 90 |
| DMP1 | None | 15 | 30 |

TABLE 3-continued

The results of transfecting NIH-3T3 fibroblasts with expression vectors encoding murine wild-type DMP1, DMP1 deletion mutants, or the point mutation K319E, on the percentage of cells that incorporate BrdU. Starved (0.1% FCS) or nonstarved (10% FCS) cells were labeled for 22 hours. M6, M8, and M11 are defined in FIG. 10, Table 1.

| Transfection | | % Cells BrdU Positive | |
|---|---|---|---|
| Product | Additive | in 0.1% FCS | in 10% FCS |
| DMP1 | cyclin D2 | 57 | 80 |
| DMP1 | cyclin E | 56 | 82 |
| M6 | None | 47 | 44 |
| M8 | None | 54 | 54 |
| M11 | None | 47 | 54 |

Coexpression of a D-type cyclin with DMP1 overrides the ability of DMP1 to transactivate a luciferase gene under the control of an artificial DMP1-responsive promoter (Table 4), as well as the ability of DMP1 to inhibit cell growth. Coexpression of CDK2, CDK4, or the specific CDK inhibitors, (i.e., INK4 proteins P16 or P19) with DMP1 had little to no effect on the stimulation of luciferase activity due to DMP1.

TABLE 4

Effect of potential antagonists and agonists on the DMP1 transactivation of the expression of luciferase by a luciferase reporter plasmid under the control of a DMP1-responsive promoter. Transactivation of luciferase reporter plasmids was normalized by arbitrarily setting the amount of luciferase activity to determined in presence of an expression vector without an insert to 1.0.

| DMP1 | Additive | Co-additive | Luciferase Activity |
|---|---|---|---|
| No | None | None | 1.0 |
| Yes | None | None | 8.4 |
| Yes | cyclin D1 | None | 1.5 |
| Yes | cyclin D2 | None | 1.6 |
| Yes | cyclin D3 | None | 1.6 |
| Yes | cyclin A | None | 5.5 |
| Yes | cyclin E | None | 1.4 |
| Yes | cyclin H | None | 5.5 |
| Yes | CDK2 | None | 7.6 |
| Yes | CDK4 | None | 6.7 |
| Yes | P16 | None | 9.2 |
| Yes | P19 | None | 8.0 |

Example 9

The Sequence and Locus of the Human Homologue of the Murine Cyclin D-binding Myb-like Protein (DMP-1)

Introduction

The identification, sequencing, isolation and chromosomal localization of the human cognate of murine cyclin D-binding Myb-like protein (DMP1) is described. The sequence of the human cognate of DMP1 (hDMP1) was obtained by identifying human Expressed Sequence Tags (ESTs) highly homologous with the known murine sequence. Overlapping human ESTs provided the sequence of the entire hDMP1 mRNA open reading frame. The chromosome locus of the hDMP1 gene was determined by fluorescence in situ hybridization (FISH) using a human genomic P1 probe. The hDMP1 gene has a 2283 base pair ORF containing 3 myb-like repeats and is found at the q21–22 locus of chromosome 7 in humans.

Materials and Methods

Identification of ESTs: The nucleotide sequence of murine DMP1 cDNA disclosed above was used to search for highly homologous human ESTs. The murine DMP1 cDNA sequence was compared with human EST sequences in GenBank using GCG software and the blast search program. Matches with three EST sequences were obtained: dbEST Id: 160555; dbEST Id: 899432; and dbEST Id: 1002550. These plasmids were purified (Quiagen Corp., Chatsworth Calif.) and sequenced yielding the entire human DMP1 coding sequence.

Sequencing: DNA sequencing reactions were assembled on a Beckman Biomek robotic system using standard dye-terminator chemistry, Taq polymerase and thermal cycling conditions described by the vendor (Perking Elmer/Applied Biosystems Division (PE/AB)). Sequencing was performed in quintuplicate to insure accuracy. Reaction products were resolved on PE/ABD model 373 and 377 automated DNA sequencers. Contig assembly was performed using the program Gap4 and the consensus sequence was further analyzed using the GCG suite of applications.

Preparation of a full length cDNA of the human DMP1 gene: Plasmids dbEST Id: 899432 and dbEST Id: 1002550 were digested in order to release the cDNA inserts corresponding to the 5' and 3' ends of hDMP1 respectively. dbEST Id: 899432 was digested with EcoR1 and Not I; while dbEST Id: 1002550 was digested with XhoI and EcoR1. The digests were run on an agarose gel and the bands corresponding to the inserts were cut from the gel and purified (Quiagen Gel Extraction kit). These purified inserts contain an overlapping region of about 300 bp and were combined as templates of a PCR reaction using primers located about 100 bp outside of the hDMP1 open reading frame. The primer sequences were determined using sequence information for hDMP1 described above.

5' primer: GGAGATAGGAACATGGGAG (SEQ ID NO:31)

3' primer: GGAGGTAAAAAGTCATAGCAG (SEQ ID NO:32)

The PCR reaction was performed using ELONGASE (and its standard amplification system) supplied by Gibco-BRL, Gaithersburg, Md., under the following conditions: 5 minutes at 94° C.; followed by 25 cycles of: 30 seconds at 94° C., 30 seconds at 50° C., and 3.5 minutes at 72° C.; followed by 10 minutes at 72° C. Amplification yielded the expected (approximately 2300–2500 bp) product which was ligated into a vector and used to transform an *E coli* derivative via TA cloning (Invitrogen).

Alternatively, plasmids EST dbs: 899432 and 1002550 can be used to transform DM1 (Gibco BRL, Gaithersburg Md.) competent bacteria. Bacteria are streaked, then grown up overnight. Plasmid preps are performed (Quiagen Corp, Santa Clarita Calif.) and the two purified plasmids are digested by simultaneous restriction digest with BspE1 and Eag1 (New England Biolabs, Beverly, Mass.) in Buffer 3 (NEBL). Products of the digest are separated by size on an agarose gel. The 986 bp band is cut from the EST db 899432 digest and purified (Quiagen). The 5640 band is cut from the gel of the EST db 1002550 digest. The two bands cut from these gels are ligated and used to transform DHFalpha competent bacteria and the plasmid is purified (Quiagen).

Identification of a human P1 probe for FISH: The nucleotide sequence of the murine DMP1 cDNA, disclosed above, was used to search for highly homologous human ESTs. One EST which was identified in this manner is dbEST Id:139573. Sequencing of the human EST probe dbEST Id: 139573 revealed homology to the murine gene DMP1 along a stretch of roughly 200 base pairs (see above). This homologous region was utilized to construct two oligomers (mybP1-5=CCTGAACAGATTATTGTTCATGCT (SEQ ID NO:43); and mybP1-3=GTGAATTTGGAT ACATGAGCA (SEQ ID NO:44)) which were then used to amplify human genomic DNA from an EBV-transformed lymphoblastoid cell line, CJTW. PCR conditions were: 25 ng template DNA; 100 ng each oligomer; Perkin-Elmer buffer and dNTPs and cycle conditions: 95° C. for 1° C., 50° C. for 2 minutes, 72° C. for 3 minutes; for 30 cycles. PCR amplification using these primers yielded a 660 base pair product representing hDMP1 genomic sequence. This PCR product was cloned (TA Cloning Kit, Invitrogen, Carlsbad Calif.) sequenced and the insert was used to screen a human P1 genomic library (Genome Systems, St. Louis Mo.). In this way a P1, clone 11098, was identified which therefore contains a fragment of human genomic DNA from the hDMP1 gene. The P1 clone 11098 was used as a probe for fluorescent in situ hybridization (see below).

Fluorescence in situ hybridization (FISH) assay: Phytohemagglutinin-stimulated human peripheral blood lymphocytes from a normal donor were used as the source of metaphase chromosomes. Purified DNA from P1 clone 11098 was labeled with digoxigenein-11-dUTP (Boehringer Mannheim, Indianapolis, Ind.) by nick translation and combined with a biotin labeled chromosome 7 centromere specific probe then hybridized overnight at 37° C. to fixed metaphase chromosomes in a solution containing sheared human DNA, 50% formamide, 10% dextan sulfate, and 2×SSC. Specific hybridization signals were detected by incubating the hybridized slides in fluorescein-conjugated sheep antibodies to digoxigenen (Boehringer Mannheim, Indianapolis, Ind.) and Texas red avidin (Vector Laboratories, Burlington, Calif.). Chromosome band assignment was made based on the relative position of the fluorescence signal relative to landmarks on the chromosome such as centromeres, telomeres, and heterochromatic euchromatic boundaries.

Results

Overlapping regions from plasmids dbEST Id: 160555 (90434) 899432 (687044), and 1002550 (70493) were found to demarcate a gene highly homologous with murine DMP1 cDNA (SEQ ID NO:2).

Plasmid dbEST Id: 160555 (94034) contains a 2013 base pair EST. The full length sequence data of dbEST ID: 160555 (90434) demonstrates that dbEST: 160555 (90434) is homologous with murine DMP1 throughout its length, beginning at nucleotide 1745 in the coding region of DMP1. The plasmid is homologous for 788 base pairs, then both constructs overlap at a TAG which is the terminal TAG of DMP1. Plasmid pT90434 continues for another 1225 base pairs before a terminal poly A tail.

Plasmid dbEST Id: 899432 (687044) contains an approximately 1130 base pair EST which is homologous to murine DMP1 beginning at the about nucleotide 30 of plasmid dbEST Id: 899432 where it's homology begins at the initiation point of DM1's 5' untranslated region and continues through the initiation AUG of hDMP1 located at nucleotide 276 of hDMP1 (corresponding to nucleotide 247 of murine DMP1). The homology continues until the termination of the plasmid approximately 850 base pairs into the hDMP1 coding region.

Plasmid dbEST Id: 1002550 (70493) contains an EST insert which is homologous with the murine DMP1 throughout it's length, beginning at about nucleotide 840 of DMP1 (i.e. about 590 bp into the DMP1 coding region), and continuing through the termination TAG at 2558 to the poly A tail extending beyond nucleotide 3750. Thus, there is extensive overlap between dbESTs 1002550, 160555 and 899432.

These three overlapping plamids describe a human gene, hDMP1 which contains a 2283 basepair open reading frame (ORF) which encodes a protein having 760 amino acids, SEQ ID NO:29. The nucleic acid determined from these clones (SEQ ID NO:28) is approximately 3760 nucleotides in length, contains an initiation ATG, a termination TAG, and a poly A tail. Immediately preceding the initiation ATG are termination codons in all three reading frames.

Gene and predicted protein sequence comparisons of hDMP1 and murine DMP1 illustrate extensive homology (FIG. 11). At the protein level hDMP1 has 94.9% identify with murine DMP1. At the nucleotide level hDMP1 has 86.9% identity with murine DMP1. A myb repeat occurs in a 292 amino acid region of identity between hDMP1 and murine DMP1 which occurs between amino acids 125 and 417 of SEQ ID NO:29. The hDMP1 gene contains a myb-like repeat between amino acids 224 and 392 of SEQ ID NO:29 which is located in a region of identity between hDMP1 and DMP1.

The hDMP1 gene lacks an alanine at amino acid 477, which is in the murine DMP1 amino acid sequence. The absence of this alanine was found in both dbESTs: 1002550 and 160555. Several acidic and basic groups in the 3' portion of the gene are also different in hDMP1 and murine DMP1.

Figure 12:
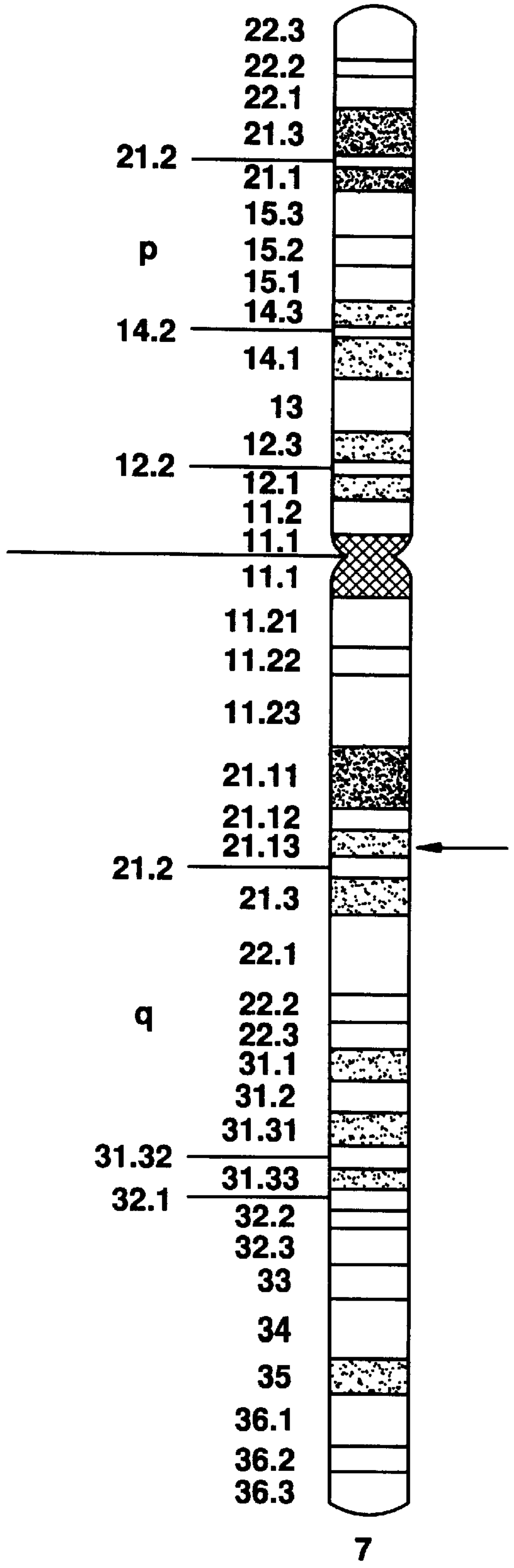
FIG. 12 shows an ideogram of chromosome 7 which shows the position of clone 11098 at $7_q21$.

Chromosomal Localization Of P1 Clone 11098 by Fluorescence in situ Hybridization Clone 11098 contains a genomic fragment of human DMP1. Chromosomal assignment of clone 11098 gene was made by fluorescence in situ hybridization. The only fluorescence signals identified were located on the long arm of a group C chromosome resembling chromosome 7 on the basis of DAPI banding. The chromosomal assignment was confirmed by cohybridizing clone 11098 with a chromosomes 7 centromere-specific probe (D7Z1). Band assignment was made by determining that clone 11098 is located 30% of the distance from the centromere to the telomere of chromosome arm $7_q$, a position which corresponds to $7_q21$. (FIG. 12).

Example 10

Induction of ARF Tumor Suppressor Gene Expression and Cell Cycle Arrest by Transcription Factor DMP1

Introduction

The singularly most frequently disrupted gene in cancer is p53 whose loss of function occurs in more than half of human tumors [Hollstein, et al., *Nucleic Acis Res.* 22:3551–3555 (1994)]. The p53 protein serves as an integrator of different cellular stress responses initiated by DNA damage, hypoxia, and hyperproliferative oncogenic signals [Levine, *Cell* 88:323–331 (1997); Prives, *Cell* 95:5–8 (1998)]. In its role as a transcription factor, it activates a series of genes that can restrict cell cycle progression and trigger apoptosis. Among p53's known transcriptional targets is Mdm2, which acts in a feedback loop to antagonize p53 function [Barak, et al., *EMBO J* 12:461–468 (1993); Wu, et al., *Genes Dev.* 7:1126–1132 (1993)]. Mdm2 binding inhibits p53 transcriptional activity, induces p53 ubiquitination [Haupt, et al., *Nature* 387:296–299 (1997); Kubbutat, et al., *Nature* 387:299–303 (1997)], and accelerates p53 nuclear export and its destruction in cytoplasmic proteasomes [Roth, et al., *EMBO J* 17:554–564 (1998)].

INK4a/ARF is perhaps the second most commonly disrupted locus in cancer cells [Ruas and Peters, *BBA Revs Cancer* (1998)]. It encodes two distinct tumor suppressor proteins: $p16^{INK4a}$, which inhibits the phosphorylation of the retinoblastoma protein (Rb) by cyclin D-dependent kinases [Serrano, et al., *Nature* 366:704–707 (1993)]; and $p19^{ARF}$ [Quelle, et al., *Cell* 83:993–1000 (1995); U.S. Pat. No. : 5,723,313, Issued Mar. 3, 1998, and U.S. Ser. No.: 09/129, 855, Filed Aug. 6, 1998, the contents of which are hereby incorporated by reference in their entireties] which stabilizes and activates p53 to promote either cell cycle arrest or apoptosis [Sherr, *Genes Dev.* 12:2984–2991 (1998)]. ARF acts to check potentially harmful growth promoting signals conveyed by overexpression of c-Myc, E2F-1, adenovirus E1A [Zindy, et al., *Genes Dev.* 12:2424–2433 (1998); De Stanchina, et al., *Genes Dev.* 12:2434–2442 (1998); Bates, et al., *Nature* 395:124–125 (1998)], or the Abelson oncogene (v-Ab1), but it is not required for p53 activation in response to DNA damage by radiation or genotoxic drugs [Kamijo, et al., *Cell* 91:649–659 (1997)]. The $p19^{ARF}$ protein binds directly to Mdm2 to neutralize its functions, thereby potentiating p53 transcriptional activity [Pomerantz, et al., *Cell* 92:713–723 (1998); Zhang and Yarbrough, *Cell* 92:725–734 (1998); Kamijo, et al., *Proc. Natl. Acad. Sci. USA* 95:8292–8297 (1998); Stott, et al., *EMBO J.* 17:5001–5014 (1998)]. Hence, loss of ARF limits cell-autonomous tumor surveillance in response to particular oncogenic signals. Animals lacking ARF function, like those lacking p53, are highly tumor prone [Kamijo, et al., *Cell* 91:649–659 (1997)]. Not surprisingly, human cancer cells that retain p53 function overexpress Mdm2 [Oliner, et al., *Nature* 358:80–83 (1992)] or sustain deletions that dismantle ARF function [Ruas and Peters, *BBA Revs Cancer* (1998)].

In attempting to determine how ARF is regulated, it was noted, disclosed below, that the mouse ARF promoter contains a potential binding site for a recently discovered transcription factor designated DMP1 [Hirai and Sherr, *Mol. Cell. Biol.* 16:6457–6467 (1996); see above]. As described above, DMP1 was isolated in a yeast two-hybrid interactive screen performed with cyclin D2 as bait, and the protein binds to any of the three D-type cyclins, but not to cyclins A, B, C, or H in vitro or when expressed with them in insect Sf9 or mammalian cells [see also, Hirai and Sherr, *Mol. Cell. Biol.* 16:6457–6467 (1996); Inoue and Sherr, *Mol. Cell. Biol.* 18:1590–1600 (1998)]. DMP1 is a novel 761-amino acid protein that contains a central DNA binding domain composed of three imperfect Myb-like repeats flanked by acidic activating domains at both its amino- and carboxyl termini. The cognate human and mouse proteins are 95% identical, and hDMP1 on human chromosome 7q21 is frequently deleted in myeloid leukemia, connoting a possible role for DMP1 as a tumor suppressor (Example 9). DMP1 binds to nonameric consensus DNA sequences containing G-G/T-A cores; those that contain GGA can also be bound by certain Ets family transcription factors [Hirai and Sherr, *Mol. Cell. Biol.* 16:6457–6467 (1996), see above]. D-type cyclins associate with a domain in DMP1 located just amino-terminal to the Myb repeats, thereby antagonizing the ability of DMP1 to bind DNA and to activate gene expression [Inoue and Sherr, *Mol. Cell Biol.* 18:1590–1600

(1998)]. Interestingly, these interactions do not depend upon the D-type cyclin-dependent kinases, CDK4 and CDK6. In fact, CDK4 and DMP1 form mutually independent complexes with D-type cyclins, and inhibitors of CDK4 do not abrogate interactions between these cyclins and DMP1. It should be noted that CDK-independent functional interactions between D-type cyclins and transcription factors are not unprecedented and have been observed with the estrogen receptor [Zwijsen, et al., *Cell* 88:405–415 (1997); Neuman, et al., *Mol. Cell. Biol.* 17:5338–5347 (1997)] and with other Myb family members [Ganter and Lipsick, *EMBO J.* 17:255–268 (1998)].

DMP1 is ubiquitously expressed at low levels in mouse cell lines and tissues, but is more prominent in non-dividing cells and may facilitate cell differentiation in certain lineages [Hirai and Sherr, *Mol. Cell. Biol.* 16:6457–6467 (1996); Inoue and Sherr, *Mol Cell. Biol.* 18:1590–1600 (1998); Inoue, et al., *J. Biol. Chem.* 273:29188–29194 (1998)]. Importantly, enforced expression of DMP1 in mouse fibroblasts can induce cell cycle arrest [Inoue and Sherr, *Mol. Cell. Biol.* 18:1590–1600 (1998)]. This suggests that genes encoding negative regulators of cell cycle progression might be direct targets of DMP1 regulation. As disclosed herein, DMP1 activates the murine ARF promoter and induces cell cycle arrest in primary diploid mouse fibroblasts in an ARF-dependent manner.

Materials and Methods

Cell culture. Primary mouse embryonic fibroblasts (MEFs) explanted at E13.5–14.5 of gestation were maintained in Dulbecco's modified Eagle's medium (DMEM) plus 10% fetal bovine serum (FBS), 2 mM glutamine, 0.1 mM nonessential amino acids, 55 μM 2-mercaptoethanol, and 10 μg/ml gentamicin [Kamijo, et al., *Cell* 91:649–659 (1997)]. NIH-3T3 and Balb-3T3 (10-1) cells were cultured in DMEM plus 10% FBS, 2 mM glutamine, with100 units/ml each of penicillin and streptomycin.

Cloning of murine ARF promoter. A 129/SvjE mouse genomic library was screened with an ARF-specific cDNA probe [Quelle, et al., *Cell* 83:993–1000 (1995)]. A 5.0 kb EcoRI fragment isolated from phage was subcloned into pBluescript, and a 990 base pair SmaI fragment hybridizing to the probe was subcloned and sequenced. A 281-base pair BamHI-BglII DNA subdomain containing a minimal promoter region was ligated to a luciferase reporter gene to yield plasmid pGL2-ARFpro BamHI. To mutate the single DMP1 consensus site in the promoter, the plasmid was digested with KpnI and ApaI and ligated with mutant oligonucleotides obtained by annealing 5'-CGGATCCGGAGCGTGCCCTGCGCGGGAGGCAG CGGGACCCCGTCGACGGCAGGGCC-3' (sense)(SEQ ID NO:37) and 5'-CTGCCG TCGACGGGGTCCCGCTGCCTCCCGCGCAGGGC ACGCTCCGGATCCGGTAC-3' (anti-sense) (SEQ ID NO:38) with mutated nucleotides in both strands underlined.

Virus production and infection. Human kidney 293T cells were transfected with a helper ecotropic retrovirus plasmid defective in psi-2 packaging sequences, together with pSRα vectors containing murine DMP1, human c-Myc, human E2F-1, or human Ets1 cDNAs [Zindy, et al., *Genes Dev.* 12:2424–2433 (1998); Inoue and Sherr, *J. Biol. Chem.* 273:29188–29194 (1998)]. Viruses were harvested every 6 hours 24–72 hours after transfection, filtered and stored at 4° C. until used for infection [Zindy, et al., *Genes Dev.* 12:2424–2433 (1998)]. In order to construct a retroviral vector containing DMP1 linked to a mutated tamoxifen-responsive element of the estrogen receptor (DMP1-ER™), a 3' 0.3 kb EcoNI DNA fragment of murine DMP1 cDNA was amplified by PCR using 5'-CACTGACCTTAAGCAGGAAG-3' (sense) (SEQ ID NO:39) and 5'-AGAAGCTT GGATCCGTGTGACAGTTTACTAAGTCCTC-3' (antisense) (SEQ ID NO: 40) primers (HindIII site italicized and Bam HI site underlined). This removed the translational stop codon and allowed insertion of DMP1 sequences 5' and in frame to those encoding the ER™ element. The product was digested with EcoNI and HindIII and used to replace the cognate 3' DMP1 cDNA segment in pBluescript. After confirmation of the nucleotide sequence, a 2.4 kb Bam HI fragment containing DMP1 coding sequences was cloned into the BamHI site of pBabe-puro retroviral vector containing the ER™ element. Pooled, filtered viruses were used to infect wild type (passage 3–5) or ARF-null MEFs ($2\times10^5$ cells seeded into 100 mm diameter culture dishes). Cells were infected with three additions of 4 ml virus-containing supernatant at 5 hour intervals in the presence of 10 μg/ml polybrene (Sigma, St. Louis, Mo.). Those infected with DMP1-ER™ virus were selected 36 hours after infection with 2 μg/ml puromycin for 48 hours prior to treatment of surviving cells with 1 μM 4-hydroxytamoxifen (4-HT) (obtained from Sigma St. Louis, Mo.).

RNA and protein expression. Quantitative RT-PCRs employed specific primers for murine ARF exon 1β (30 cycles) and for β-actin (20 cycles) used as a control [Zindy et al., *Oncogene* 15:203–211 (1997)]. Protein analyses were performed as described [Zindy, et al., *Genes Dev.* 12:2424–2433 (1998); Kamijo, et al., *Proc. Natl. Acad. Sci. USA* 95:8292–8297 (1998)]. Samples (200 μg of protein per lane) were separated by denaturing electrophoresis and transferred to nitrocellulose membranes (MSI, Westboro, Mass.) prior to immunoblotting. Anti-actin (C-11) was from Santa Cruz Biotechnology (Santa Cruz, Calif.).

Electrophoretic mobility shift assay (EMSA). Recombinant DMP1 protein was prepared in Sf9 cells [Hirai and Sherr, *Mol. Cell. Biol.* 16:6457–6467 (1996)]. Purified bacterial proteins representing the Ets1 DNA binding domain or full-length Ets1 [Inoue, et al., *J. Biol. Chem.* 273:29188–29194 (1998)] were used. EMSAs were performed [Inoue and Sherr, *Mol. Cell. Biol.* 18:1590–1600 (1998)] using either a 281-bp genomic fragment (−225 to +56) or double-stranded oligonucleotides containing the DMP1/Ets site obtained by annealing oligonucleotide 5'-AATTGGGACCCCGGATGCGGCAG-3' (sense strand SEQ ID NO:41); DMP1/Ets consensus sequence underlined) with a complementary antisense strand. For competition experiments, a 200-fold excess of unlabelled oligonucleotides was added to reaction mixtures before the probe. To verify the identity of the proteins in shifted complexes, reaction mixtures were incubated with control nonimmune rabbit serum (NRS), serum AF [Hirai and Sherr, *Mol. Cell. Biol.* 16:6457–6467 (1996)] and M-10 (both to DMP1 carboxylterminal epitopes), S-19 (DMP1 N-terminus), or C-20 (Ets1 C-terminus) before electrophoresis. M-10, S-19, and C-20 were from Santa Cruz Biotechnology.

Transactivation assays. NIH-3T3 cells were transfected with 4 μg of pGL2-ARFpro BamHI or its DMP1 binding site mutant, with or without increasing amount of pFLEX-DMP1, pEVRFO-Ets1, pCMV-Ets2, pRcRSV-Elf1, pdEB-Fli1, pdEB-EWS-Fli1 or pCMV-E2F-1 (89-437), and 4 μg β-actin SEAP control vectors [Inoue and Sherr, *Mol. Cell. Biol.* 18:1590–1600 (1998); Inoue et al., *J. Biol. Chem.* 273:29188–29194 (1998); Davis and Roussel, *Gene* 171:265–269 (1996); Baily et al., *Mol. Cell. Biol.*

14:3230–3241 (1994)]. Transfections and normalization of luciferase levels with internal control SEAP levels were performed as described [Inoue and Sherr, *Mol. Cell. Biol.* 18:1590–1600 (1998)].

BrdU incorporation and immunofluorescence. Wild-type or ARF-null MEFs ($4 \times 10^4$ cells) were seeded on gelatin-coated coverslips 16 hours before virus infection. Cells were infected three times with empty vector, or vectors expressing murine DMP1, human c-Myc, human E2F-1, or human Ets1. Cells were labeled 36 hours after virus infection with bromodeoxyuridine (BrdU, Sigma) for 14 hours in complete medium. For pulse labeling, MEFs were treated with 2 $\mu$M 4-HT for 36 hours and labeled with BrdU for three hours at different intervals throughout the inductive phase. Cells were fixed in ice-cold methanol-acetone (1:1) for 10 min at −20° C. and then were stained with affinity-purified antibodies to DMP1 (AF) [Hirai and Sherr, *Mol. Cell. Biol.* 16:6457–6467 (1996)], $p19^{ARF}$ [Quelle et al., *Cell* 83:993–1000 (1995)], c-Myc (Upstate Biotech. Inc.), or Ets-1 (C-20, Santa Cruz) and counterstained with a 1:1 dilution of monoclonal antibodies to BrdU (Amersham Life Science) as described [Inoue and Sherr, *Mol. Cell. Biol.* 18:1590–1600 (1998)].

Apoptosis assays. Wild-type MEFs infected with the indicated retroviruses for 36 hours were starved for serum for 24 hours. Viability was determined by trypan blue dye exclusion, and DNA fragmentation was monitored by a terminal deoxynucleotidyl transferase (FACS-TUNEL) assay and by measurement of subdiploid DNA content of propidium iodide-stained nuclei [Zindy et al., *Genes Dev.* 12:2424–2433 (1998)].

Results

Figure 14A:
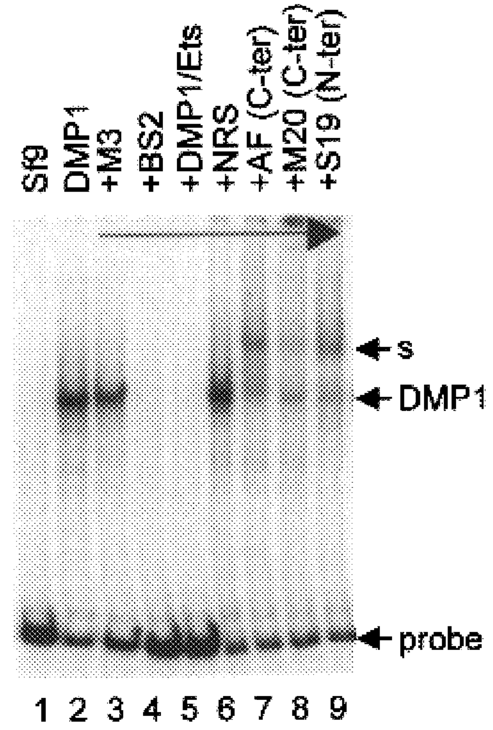
FIGS. 14A–14C show that DMP1 binds and transactivates the ARF promoter.

The nucleotide sequence of the proximal promoter region of the murine ARF gene relative to the transcription initiation site as defined by S1 mapping analysis was determined (FIG. 13). Putative binding sites for known transcription factors were identified in a 300 base pair region 5' to the start site, which included a perfect DMP1/Ets consensus at −189 to −181. A recombinant DMP1 protein produced in baculovirus-infected insect Sf9 cells bound to a radiolabeled 281 base pair fragment from the ARF promoter encompassing nucleotides −225 to +56 (FIG. 14A, lane 2). Binding of DMP1 to the 281 base pair promoter fragment was completely inhibited by a 23 base pair oligonucleotide containing the DMP1/Ets consensus sequence (FIG. 14A, lane 5), as well as by a variant oligonucleotide [CCCGTATGT, previously designated BS2 [Hirai, H. & Sherr, *Mol. Cell. Biol.,* 16:6457–6467 (1996)] that lacks the GGA core sequence required for Ets binding (FIG. 14A, lane 4). Conversely, an oligonucleotide containing a reiterated Ets-specific consensus binding site (CCCGGAAGT, designated M3) to which DMP1 cannot bind did not compete (FIG. 14A, lane 3). DNA:protein complexes containing bound DMP1 were further retarded in mobility in the presence of antibodies directed to different DMP1 epitopes (lanes 7–9), but not by non-immune serum (lane 6).

Figure 14B:
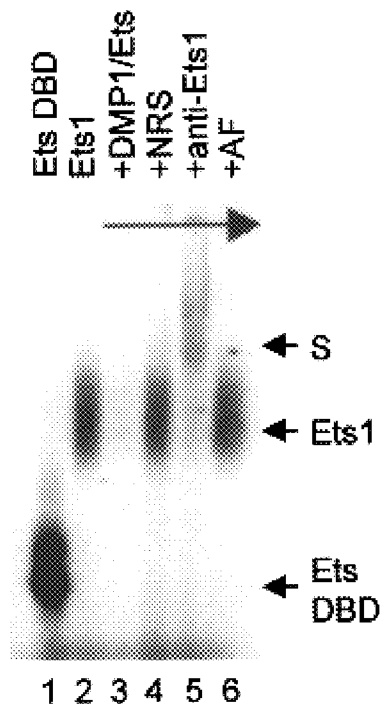

Because the DMP1 site on the ARF promoter contains a GGA core (FIG. 13), Ets family proteins can also bind to it. A recombinant Ets1 protein produced in bacteria or a segment representing its DNA binding domain bound to a short 23 base pair double-stranded oligonucleotide containing the ARF DMP1 consensus site (FIG. 14B, lanes 1 and 2). Binding was competed by the cognate oligonucleotide (FIG. 14B, lane 3), and the mobility of these complexes was retarded using antiserum to Ets1 but not to DMP1 (lanes 5 and 6).

Figure 14C:
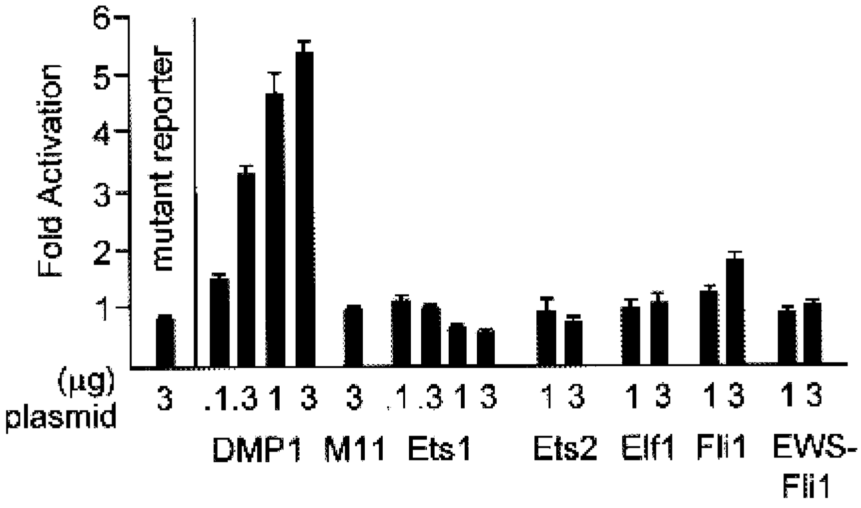

When the 281 bp ARF promoter fragment ligated to a luciferase reporter gene and transfected into NIH-3T3 fibroblasts, cotransfection with increasing concentrations of a DMP1 expression vector enhanced reporter gene expression, whereas a DMP1 point mutant (M11) that is unable to bind to DNA had no activity (FIG. 14C). Similarly, DMP1 deletion mutants defective in transactivation [Inoue and Sherr, *Mol. Cell. Biol.* 18:1590–1600 (1998)] were inactive in this assay. Mutation of the DMP1 binding site within the ARF promoter [changing CCCGGATGC, (SEQ ID NO:33) to CCCGTCGAC, (SEQ ID NO:42)] also completely abolished transactivation by wild-type DMP1 (FIG. 14C, mutant reporter). Therefore, sequences within the −189 to −181 ARF promoter segment were the only ones responsible for DMP1-mediated transactivation. Although Ets1 could bind to a 23 base pair oligonucleotide containing the DMP1 consensus site (FIG. 14B), several Ets proteins were unable to induce significant reporter gene expression from the more complex 281 base pair ARF promoter (FIG. 14C). Only Fli1 showed minimal activity, while Ets1 was slightly inhibitory. Therefore, in the context of the larger promoter fragment, DMP1 binding is strongly preferred.

Figure 15A:
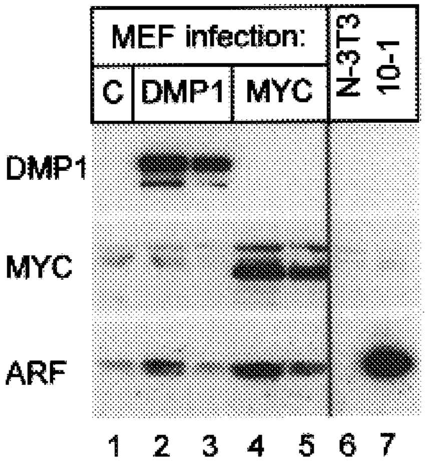
FIGS. 15A–15D show that DMP1 induces $p19^{ARF}$ and cell cycle arrest in wild type but not ARF-null MEFs.
Figure 15B:
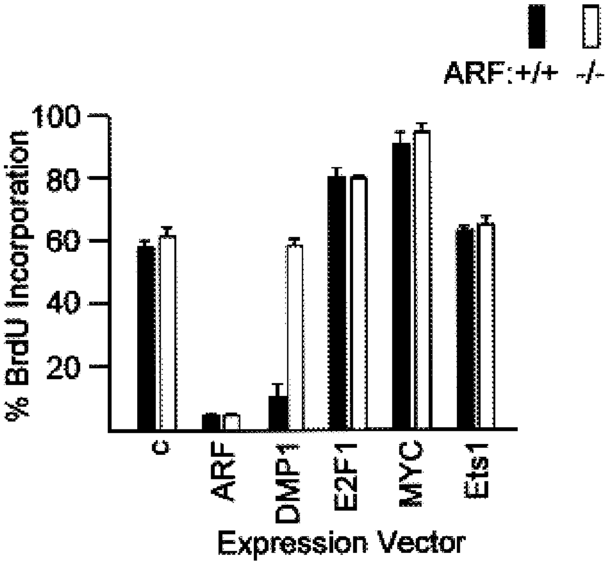

Based on the above observations, it was determined as to whether introduction of DMP1 would induce synthesis of the endogenous ARF protein in normal diploid fibroblast strains. Early passage, mouse embryo fibroblast strains (MEFs) were infected with retroviral vectors encoding either DMP1 or c-Myc, a known rapid inducer of $p19^{ARF}$ protein expression used here as a positive control [Zindy et al., *Genes Dev.* 12:2424–2433 (1998)]. In early passage MEFs, $p19^{ARF}$ levels are low and remained so in cells infected with the naked expression vector (FIG. 15A, lane 1). Both DMP1 (FIG. 15A, lanes 2, 3) and c-Myc (FIG. 15A, lanes 4, 5) induced ARF protein synthesis. Although the blot was normalized for protein input, the levels of $p19^{ARF}$ induced by DMP1 were calculated to be 2-fold higher than those induced by Myc, because fewer cells were productively infected with the DMP1 virus in this experiment (see FIG. 15A). In turn, wild-type MEFs infected with DMP1 underwent cell cycle arrest, similar to cells infected with a retrovirus encoding $p19^{ARF}$ itself (FIG. 15B). In direct contrast, MEF strains derived from ARF-null animals were refractory to DMP1-induced arrest, indicating that ARF function was required for inhibition of S phase entry. Cells infected with a vector encoding Ets-1, whether containing or lacking ARF, behaved indistinguishably from those infected with the control vector (FIG. 15B), consistent with the inability of Ets proteins to stimulate reporter gene expression driven by the ARF promoter fragment (FIG. 14C).

Figure 15C:
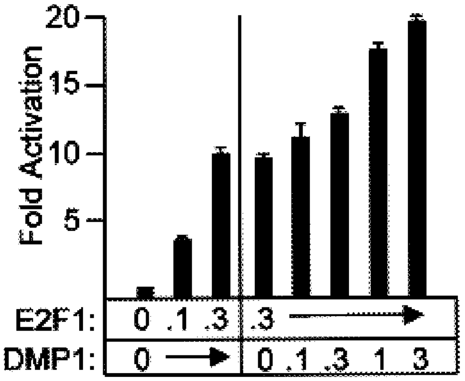

E2F-1, E1A, c-Myc, and v-Ab1 induce $p19^{ARF}$ expression, as part of a checkpoint response that limits their overexpression, but each also triggers the expression of genes that promote both G1 phase progression and apoptosis [Zindy et al., *Genes Dev.* 12:2424–2433 (1998); De Stanchina et al., *Genes Dev.* 12:2434–2442 (1998); Bates et al., *Nature* 395:124–125 (1998)]. Myc and E2F-1 acutely increased the S phase fraction of MEFs following viral infection, and unlike DMP1, neither exhibited differential effects in ARF-positive versus ARF-null MEFs maintained in the presence of serum (FIG. 15B). The mouse ARF promoter contains at least two potential E2F-1 binding sites in the −208 to 127 segment that includes the DMP1 binding site (FIG. 13). Results obtained with human ARF were confirmed demonstrating that E2F-1 could stimulate ARF promoter-dependent gene expression [Bates et al., *Nature* 395:124–125 (1998)] and also could act in conjunction with DMP1 (FIG. 15C). The human ARF promoter [(SEQ ID NO:36), accession no: AF082338, Robertson and Jones, *Mol. Cell. Biol.* 18:6457–6473 (1998)] also was found to contain a high affinity DMP1 binding site (GACGGATGT, SEQ ID NO:35) at nucleotides −397 to −389 as disclosed herein, relative to the transcriptional start site. As for Myc, the growth promoting effects of E2F-1 were sufficient to override ARF-induced arrest (FIG. 15B).

Figure 15D:
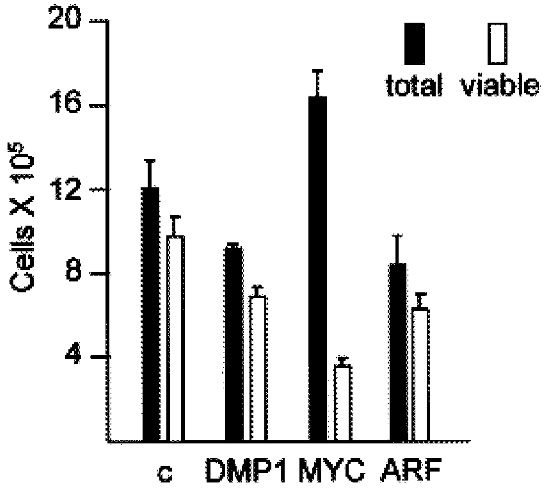

On the other hand, MEFs overexpressing c-Myc, E2F-1, or E1A are exquisitely sensitive to apoptosis. The ability of these proteins to induce cell death is enhanced in MEFs deprived of serum [Evan et al., *Cell* 69:119–128 (1992)] but is significantly attenuated in cells lacking ARF or p53 function [Zindy et al., *Genes Dev.* 12:2424–2433 (1998); De Stanchina et al., *Genes Dev.* 12:2434–2442 (1998)]. Importantly, ARF overexpression per se does not trigger apoptosis [Quelle et al., *Cell* 83:993–1000 (1995)], so the pro-apoptotic functions of Myc or E2F-1, although countered by ARF loss, are likely mediated through other target genes. As expected, in wild-type MEFs deprived of serum, ectopic Myc expression induced cell death, however DMP1, like ARF, led to growth arrest and did not trigger apoptosis (FIG. 15D), as confirmed by FACS-TUNEL assays.

Figure 16:
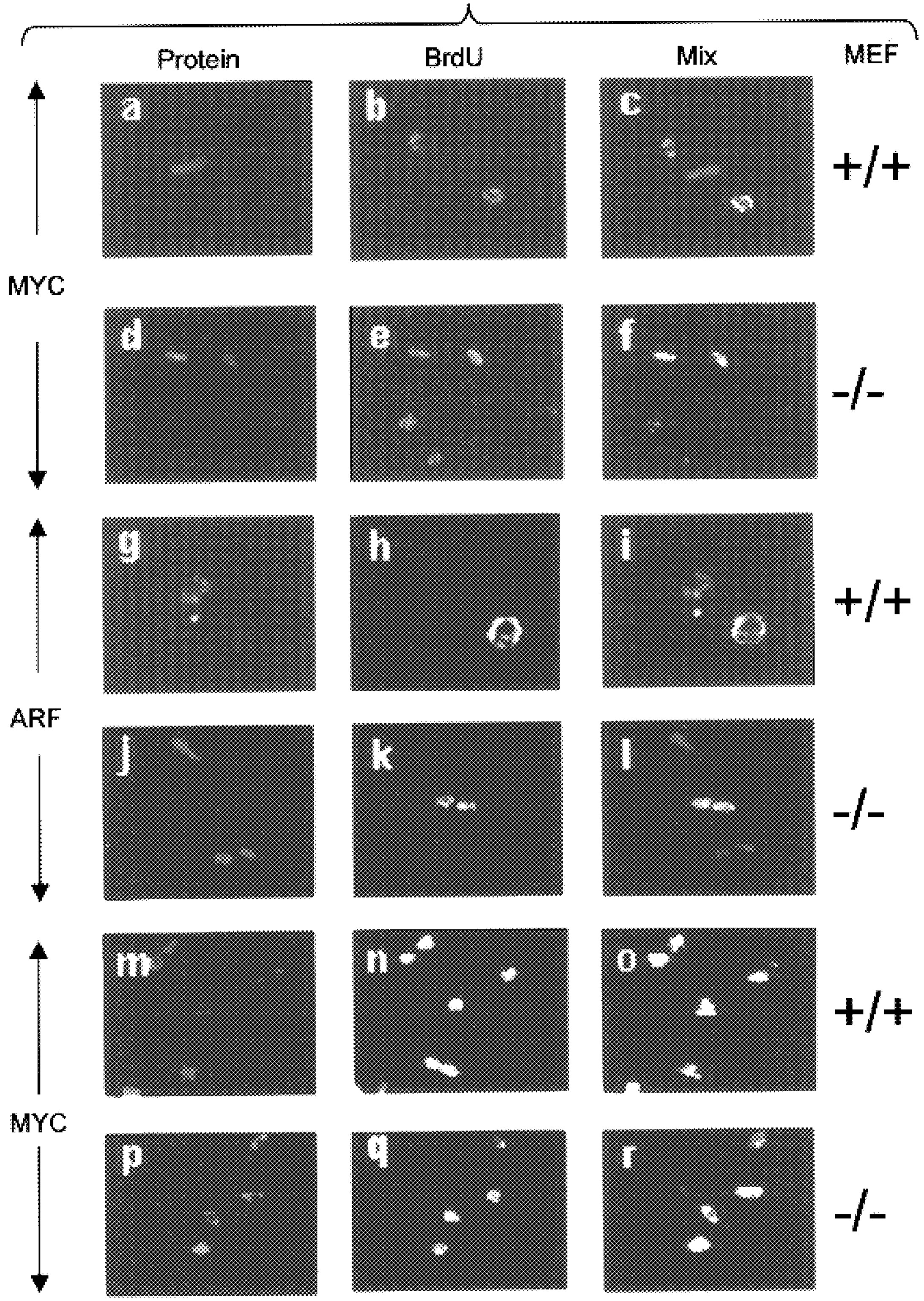
FIGS. 16*a*–16*r* show that DMP1-induced arrest depends on ARF. Wild type or ARF-null MEFs (indicated at the right) were infected for 36 hours with the different expression vectors (noted at the left) and scored for vector-induced protein expression (red fluorescence, left column), BrdU incorporation (green fluorescence, middle column), and mixed fluorescence (yellow, right column). Wild-type DMP1 overexpressing cells failed to incorporate BrdU (FIG. 16*a*–16*c*), whereas ARF-null cells entered S phase (FIG. 16*d*–16*f*). ARF arrests both MEF cell types (FIG. 16*g*–16*l*) and Myc arrests neither (FIG. 16*m*–16*r*).

FIG. 16 illustrates representative data obtained with both wild type and ARF-null MEFs infected with DMP1 virus (FIG. 16, *a–f*), ARF virus (FIG. 16, *g–l*), or c-Myc virus (FIG. 16, *m–r*). Both ectopically expressed DMP1 and ARF induced cell cycle arrest. Cells expressing either of these proteins (red fluorescence) did not incorporate BrdU (green fluorescence), whereas uninfected cells in the same cultures proceeded into S phase. Although both wild-type (FIG. 16, *g–i*) and ARF-null cells (FIG. 16, *j–l*) were arrested by ectopically expressed ARF protein, DMP1 was only effective in ARF-positive cells (FIG. 16, *a–c*). In contrast, cells infected with c-Myc virus continued to proliferate when maintained in serum-containing medium (FIG. 16, *m–r*).

Figure 17A:
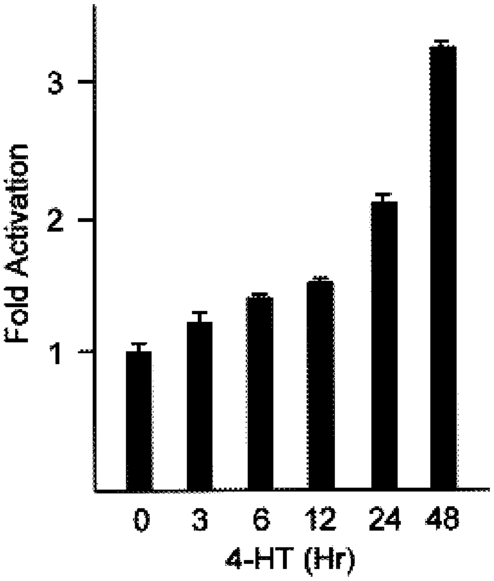
FIGS. 17A–17E show the conditional ARF induction and growth arrest of wild-type MEFs by DMP1-ER™.
Figure 17B:
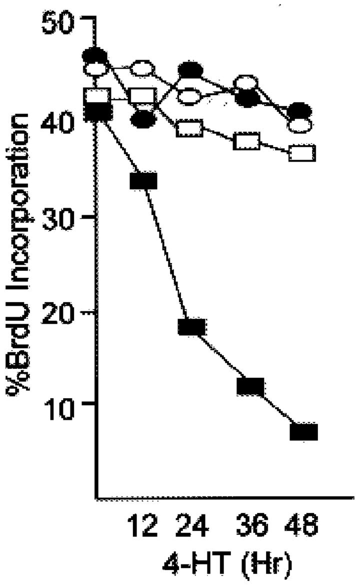
Figure 17C:
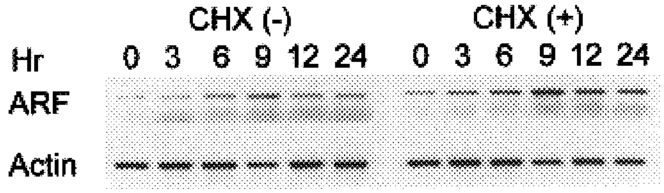
Figure 17D:
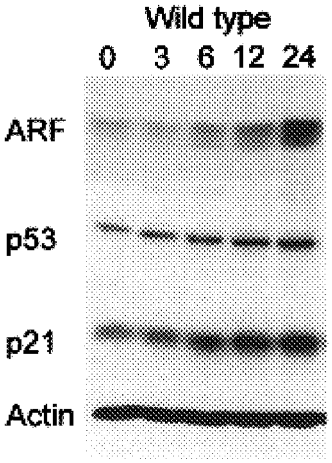
Figure 17E:
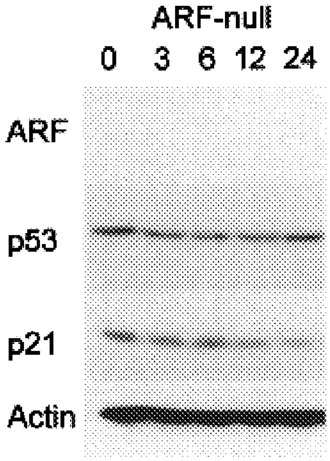

To determine the kinetics of ARF induction in response to DMP1, a DMP1-ER™ fusion protein was constructed that is conditionally regulated in response to 4-hydroxytamoxifen (4-HT). In NIH-3T3 fibroblasts, the DMP1-ER™ construct activated a cotransfected ARF-luciferase promoter-reporter construct in response to 4-HT treatment (FIG. 17A). When wild-type primary MEFs infected with a DMP1-ER™ retrovirus were treated with 4-HT, they underwent growth arrest, whereas ARF-null MEFs did not respond (FIG. 17B). 4-HT treatment of wild-type cells induced expression of ARF mRNA (FIG. 17C) and protein (FIG. 17D–17E). The increase in ARF mRNA was maximal by 9 hours after 4-HT addition and was potentiated when cells were also treated with cycloheximide (CHX) (FIG. 17C), indicating that DMP1-mediated induction does not require new protein synthesis. 4-HT treatment led to increases in p53 and the p53-responsive CDK inhibitor, $p21^{Cip1}$, whereas ARF-null MEFs did not exhibit increases in either protein (FIG. 17D–17E), consistent with results above indicating that DMP1-induced arrest depends upon ARF function. In turn, ARF-induced arrest strictly depends upon functional p53 [Kamijo et al., *Cell* 91:649–659 (1997)], and consistently, the proliferation of MEFs derived from p53-null mice was not affected by DMP1.isis Discussion The DMP1 transcription factor binds to a single consensus site in the mouse ARF promoter to activate gene expression. Mutation of this binding site abolished DMP1-stimulated expression of a reporter gene driven by a DNA fragment containing residues −225 to +56 of the ARF promoter. Conversely, a DMP1 point mutant that no longer binds to DNA was transcriptionally inert. Ets1 and Ets2 transcription factors can also bind to short oligonucleotides containing the DMP1 consensus binding site, but five Ets family members were unable to activate reporter gene expression driven by the larger 281 base pair ARF promoter fragment, indicating that DMP1 is the preferred regulator in this context. Similar effects have been observed with the promoter of the aminopeptidase-N/CD13 gene on which DMP1-DNA complexes were significantly more stable than those containing Ets factors [Inoue et al., *J. Biol. Chem.* 273:29188–29194 (1998)]. In agreement with these findings, ectopic expression of DMP1 in wild-type MEF strains induced expression of the $p19^{ARF}$ protein and caused cell cycle arrest, but Ets1 overexpression was without effect.

Mutants of DMP1 defective in DNA binding or in transactivation do not cause cell cycle arrest underscoring the requirement for target gene expression [Inoue and Sherr, *Mol. Cell. Biol.* 18:1590–1600 (1998)]. The fact that ARF-null MEFs did not stop dividing in response to DMP1 now provides direct evidence that ARF function is required for DMP1's anti-proliferative effects on the cell cycle, at least in primary diploid fibroblasts. ARF-induced arrest depends upon p53 [Kamijo, et al., *Cell* 91:649–659 (1997)], and conditional activation of a DMP1-ER™ fusion protein induced expression of p53 and of the p53-regulated $p21^{Cip1}$ protein in wild-type MEFs, but not in their ARF-null counterparts. As expected, the proliferation of p53-null MEFs was also unaffected by DMP1, and $p21^{Cip1}$ was not induced. Therefore, DMP1 up-regulates ARF gene expression in primary MEFs leading in turn to p53-dependent growth arrest.

These data do not formally preclude the possibility that DMP1 can also activate other genes important in cell cycle control. For example, much higher levels of ectopic DMP1 expression can inhibit cell cycle entry in NIH-3T3 cells that have sustained ARF-deletions, implying that DMP1 co-regulates other relevant targets. Myc can activate p53 through ARF-dependent and ARF-independent pathways, although much higher Myc levels are required to activate p53 when ARF is absent [Zindy et al., *Genes Dev.* 12:2424–2433 (1998)]. As disclosed herein, however, DMP1 does not induce p53 in ARF-null MEFs. In a survey for other DMP1-regulated genes, DMP1 can indirectly up-regulate reporter gene expression from the $p27^{Kip1}$ promoter in NIH-3T3 cells [Inoue, et al., *J. Biol. Chem.* 273:29188–19194 (1998)], even though this promoter fragment lacks a consensus DMP1 binding site. Unlike ARF-null cells, the proliferation of $p27^{Kip1}$-null MEFs is still inhibited by DMP1. DMP1 did not induce $p21^{Cip1}$ in ARF-null MEFs (FIG. 17D–17E), and did not significantly induce reporter gene expression driven by the $p21^{Cip1}$ promoter.

Cell cycle arrest induced by ectopic expression of DMP1 is antagonized by D-type cyclin overexpression [Inoue and Sherr, *Mol. Cell. Biol.* 18:1590–1600 (1998)]. Co-expression of cyclin D1 with DMP1-ER™ in primary MEFs can counter cell cycle arrest induced by 4-HT as disclosed herein. Effects of D-type cyclins on DMP1-mediated gene expression could occur as a result of direct physical interactions between DMP1 and D-type cyclins or, alternatively, through CDK4-dependent phosphorylation of the retinoblastoma protein and up-regulation of E2Fs, which can drive cells into S phase.

The effects of DMP1 on the ARF-p53 pathway differ in several key respects from the consequences of overexpression of Myc, E1A, E2F-1, all of which also activate $p19^{ARF}$ synthesis [Zindy et al., *Genes Dev.* 12:2424–2433 (1998);

De Stanchina et al., *Genes Dev.* 12:2434–2442 (1998); Bates et al., *Nature* 395:124–125 (1998)]. First, Myc has not been demonstrated to bind to the ARF promoter, and its inductive effects on p19$^{ARF}$ protein synthesis may be indirect. Second, ectopic Myc and E2F-1 expression cause conflicting biologic responses in the sense that both stimulate S phase entry and yet trigger programmed cell death. The apoptotic response can be masked by survival factors that are normally present in cell culture medium, so that cell death becomes more pronounced when MEFs overexpressing Myc are deprived of serum [Evan et al., *Cell* 69:119–128 (1992)]. Compared to normal cells, those that have lost ARF or p53 function become relatively resistant to apoptosis induced by Myc, and such variants soon become established as continuously proliferating cell lines [Zindy et al., *Genes Dev.* 12:2424–2433 (1998)]. In the latter populations, the growth promoting effects of Myc are unchecked, and the proliferative rate of the cells is accelerated. Therefore, Myc and E2F overexpression is normally countered by ARF-dependent signals that antagonize rapid cell proliferation and helps to promote apoptosis in a p53-dependent manner [reviewed in Sherr, *Genes Dev.* 12:2984–2991 (1998)]. Because enforced ARF expression arrests wild type cells but does not kill them [Quelle et al., *Cell* 83:993–1000 (1995)], other functions of Myc in addition to activation of the ARF-p53 pathway are required for apoptosis. DMP1 lacks these collateral functions, because like ARF itself, DMP1 induces cell cycle arrest but does not provoke cell death.

Because the ARF and DNA damage pathways that impinge on p53 are distinct, activation of ARF by low levels of Myc or E1A can sensitize cells to the p53-dependent effects of genotoxic drugs or irradiation [De Stanchina et al., *Genes Dev.* 12:2434–2442 (1998)]. However, the growth promoting properties of Myc and E1A also contribute to rapid selection of drug-resistant variants that lose ARF-p53 checkpoint control [Zindy et al., *Genes Dev.* 12:2424–2433 (1998)]. Because DMP1 exhibits no overt growth promoting functions, it may be more useful as a specific sensitizer of p53-dependent killing in response to common chemotherapeutic regimens, without as great a risk of selection for p53-negative variants.

The following is a list of documents related to the above disclosure and particularly to the experimental procedures and discussions. These documents, and all others cited above, should be considered as incorporated by reference in their entirety.

1. Anderson, S. J., M. A. Gonda, C. W. Rettenmier, and C. J. Sherr. 1984. Subcellular localization of glycoproteins encoded by the viral oncogene v-fms. J Virol 51:730–741.
2. Andrews, N. C. and D. V. Faller. 1991. A rapid micropreparation technique for extraction of DNA-binding proteins from limiting numbers of mammalian cells. Nuc Acids Res 19:2499–2510.
3. Anton, I. A. and J. Frampton. 1988. Tryptophans in myb proteins. Nature 336:719
4. Baldin, V., J. Lukas, M. J. Marcote, M. Pagano, and G. Draetta. 1993. Cyclin D1 is a nuclear protein required for cell cycle progression in G1. Genes & Devel 7:812–821.
5. Bartel, P. L., C.-T. Chien, R. Sternglanz, and S. Fields. 1993. Using the two hybrid system to detect protein-protein interactions. p. 153–179. In (ed. D. A. Hartley) In: Cellular interactions in development: a practical approach. Oxford University Press, Oxford UK.
6. Biedenkapp, H., U. Borgmeyer, A. E. Sippel, and K. H. Klempnauer. 1988. Viral myb oncogene encodes a sequence-specific DNA binding activity. Nature 335:835–837.
7. Chen, C. and H. Okayama. 1987. High-efficiency transformation of mammalian cells by plasmid DNA. Mol Cell Biol 7:2745–2752.
8. Chodosh, L. A. 1988. Mobility shift DNA binding assay using gel electrophoresis, p. 12.2.1–12.2.10. In F. M. Ausubel, R. Brent, R. E. Kingston, D. D. Moore, J. G. Seidman, J. A. Smith, and K. Struhl (ed.), Current Protocols in Molecular Biology. Greene Pub., Wiley Inter. New York.
9. Clarke, A. R., E. R. Maandag, M. van Roon, N. M. T. van der Lugt, M. van der Valk, M. L. Hooper, A. Berns, and H. te Riele. 1992. Requirement for a functional Rb-1 gene in murine development. Nature 359:328–330.
10. Davis, J. N. and M. F. Roussel. 1996 Cloning and expression of murine Elf1 *Gene* 171:265–269.
11. Dowdy, S. F., P. W. Hinds, K. Louis, S. I. Reed, A. Arnold, and R. A. Weinberg. 1993. Physical interactions of the retinoblastoma protein with human cyclins. Cell 73:499–511.
12. Downing, J. R., C. W. Rettenmier, and C. J. Sherr. 1988. Ligand-induced tyrosine kinase activity of the colony stimulating factor-1 receptor in a murine macrophage cell line. Mol Cell Biol 8:1795–1799.
13. Downing, J. R., S. A. Shurtleff, and C. J. Sherr. 1991. Peptide antisera to human colony-stimulating factor 1 receptor detect ligand-induced conformational changes and a binding site for phosphatidylinositol 3-kinase. Mol Cell Biol 11:2489–2495.
14. Durfee, T., K. Becherer, P.-L. Chen, S.-H. Yeh, Y. Yang, A. Kilburn, W.-H. Lee, and S. J. Elledge. 1993. The retinoblastoma protein associates with the protein phosphatase type 1 catalytic subunit. Genes & Devel. 7:555–569.
15. Ewen, M. E., H. K. Sluss, C. J. Sherr, H. Matsushime, J. Kato, and D. M. Livingston. 1993. Functional interactions of the retinoblastoma protein with mammalian D-type cyclins. Cell 73:487–497.
16. Gabrielson, O. S., A. Sentenac, and P. Fromageot. 1991. Specific DNA binding by c-myb: evidence for a double helix-turn-helix-related motif. Science 253:1140–1143.
17. Gonda, T. J., N. M. Gough, A. R. Dunn, and J. de Blaquiere. 1985. Nucleotide sequence of cDNA clones of the murine myb proto-oncogene. EMBO J 4:2003–2008.
18. Graham, F. L., J. Smiley, W. C. Russell, and R. Nairn. 1977. Characteristics of a human cell line transformed by DNA from human adenovirus type 5. J Gen Virol 36:59–72.
19. Guan, K., C. W. Jenkins, Y. Li, M. A. Nichols, X. Wú, C. L. O'Keefe, A. G. Matera, and Y. Xiong. 1994. Growth suppression by p18, a p16INK4/MTS1__ and p14INK4/MTS2__ related CDK6 inhibitor, correlates with wild-type pRb function. Genes Devel. 8:2939–2952.
20. Hirai, H., M. F. Roussel, J. Kato, R. A. Ashmun, and C. J. Sherr. 1995. Novel INK4 proteins, p19 and p18, are specific inhibitors of cyclin D-dependent kinases CDK4 and CDK6. Mol Cell Biol. 15:2672–2681.
21. Inaba, T., L. H. Shapiro, T. Funabiki, A. E. Sinclair, B. G. Jones, R. A. Ashmun, and A. T. Look. 1994. DNA-binding specificity and trans-activating potential of the leukemia-associated E2A-hepatic leukemia factor fusion protein. Mol Biol Cell 14:3403–3413.
22. Jacks, T., A. Faxeli, E. M. Schmitt, R. T. Bronson, M. A. Goodell, and R. A. Weinberg. 1992. Effects of an Rb mutation in the mouse. Nature 359:295–300.

23. Kato, J., H. Matsushime, S. W. Hiebert, M. E. Ewen, and C. J. Sherr. 1993. Direct binding of cyclin D to the retinoblastoma gene product (pRb) and pRb phosphorylation by the cyclin D-dependent kinase, CDK4. Genes & Devel 7:331–342.

24. Klempnauer, K. H., T. J. Gonda, and J. M. Bishop. 1982. Nucleotide sequence of the retro viral leukemia gene v-myb and its cellular progenitor c-myb: the architecture of a transduced onco gene. Cell 31:453–463.

25. Klempnauer, K. H. and A. E. Sippel. 1987. The highly conserved amino-terminal region of the protein encoded by the v-myb oncogene functions as a DNA-binding domain. EMBO J 6:2719–2725.

26. Koh, J., G. H. Enders, B. D. Dynlacht, and E. Harlow. 1995. Tumour-derived p16 alleles encoding proteins defective in cell cycle inhibition. Nature 375:506–510.

27. Lee, E. YH. P., C. Chang, N. Hu, Y. J. Wang, C. Lai, K. Herrup, W. Lee, and A. Bradley. 1992. Mice deficient for Rb are nonviable and show defects in neurogenesis and haematopoiesis. Nature 359:288–294.

28. Lukas, J., J. Bartkova, M. Rohde, M. Strauss, and J. Bartek. 1995. Cyclin D1 is dispensable for G1 control in retinoblastoma gene-deficient cells, independent of CDK4 activity. Mol Cell Biol 15:2600–2611.

29. Lukas, J., H. Muller, J. Bartkova, D. Spitkovsky, A. A. Kjerulff, P. Jansen-Durr, M. Strauss, and J. Bartek. 1994. DNA tumor virus oncoproteins and retinoblastoma gene mutations share the ability to relieve the cell's requirement for cyclin D1 function in G1. J Cell Biol 125:625–638.

30. Lukas, J., D. Parry, L. Aagaard, D. J. Mann, J. Bartkova, M. Strauss, G. Peters, and J. Bartek. 1995. Rb-dependent cell cycle inhibition by p16CDKN2 tumour suppressor. Nature 375:503–506.

31. Macleod, K., D. Leprince, and D. Stehelin. 1992. The ets gene family. Trends Biochem Sci 17:251–256.

32. Matsuoka, M., J. Kato, R. P. Fisher, D. O. Morgan, and C. J. Sherr. 1994. Activation of cyclin-dependent kinase-4 (CDK4) by mouse MO15-associated kinase. Mol Cell Biol 14:7265–7275.

33. Matsushime, H., M. E. Ewen, D. K. Strom, J. Kato, S. K. Hanks, M. F. Roussel, and C. J. Sherr. 1992. Identification and properties of an atypical catalytic subunit (p34PSKJ3/CDK4) for mammalian D-type G1 cyclins. Cell 71:323–334.

34. Matsushime, H., D. E. Quelle, S. A. Shurtleff, M. Shibuya, C. J. Sherr, and J. Kato. 1994. D-type cyclin-dependent kinase activity in mammalian cells. Mol Cell Biol 14:2066–2076.

35. Matsushime, H., M. F. Roussel, R. A. Ashmun, and C. J. Sherr. 1991. Colony-stimulating factor 1 regulates novel cyclins during the G1 phase of the cell cycle. Cell 65:701–713.

36. Matsushime, H., M. F. Roussel, and C. J. Sherr. 1991. Novel mammalian cyclin (CYL) genes expressed during G1. p. 69–74. In Anonymous, The Cell Cycle. Cold Spring Harbor Symp Quant Biol, Cold Spring Harbor, N.Y.

37. Matsuura, Y., R. D. Possee, H. A. Overton, and D. H. L. Bishop. 1987. Baculovirus expression vectors: The requirements for high level expression of proteins, including glycoproteins. J Gen Virol 68:1233–1250.

38. Medema, R. H., R. E. Herrera, F. Lam, and R. A. Weinberg. 1995. Growth suppression by p16ink4 requires functional retinoblastoma protein. Proc. Natl. Acad. Sci. USA 92:6289–6293.

39. Meyerson, M. and E. Harlow. 1994. Identification of a G1 kinase activity for cdk6, a novel cyclin D partner. Mol Cell Biol 14:2077–2086.

40. Nakagoshi, H., T. Nagese, C. Kanei-Ishii, Y. Ueno, and S. Ishii. 1990. Binding of the c-myb proto-oncogene product to the simian virus 40 enhancer stimulates transcription. J Biol Chem 265:3479–3483.

41. Ness, S. A., A. Marknell, and T. Graf. 1989. The v-myb oncogene product binds to and activates the promyelocyte-specific mim-1 gene. Cell 59:1115–1125.

42. Ogata, K., S. Morikawa, H. Nakamura, A. Sekikawa, T. Inoue, H. Kanai, A. Sarai, S. Ishii, and Y. Nishimura. 1994. Solution structure of a specific DNA complex of the myb DNA-binding domain with cooperative recognition helices. Cell 79:639–648.

43. Pardee, A. B. 1989. G1 events and regulation of cell proliferation. Science 246:603–608.

44. Quelle, D. E., R. A. Ashmun, S. A. Shurtleff, J. Kato, D. Bar-Sagi, M. F. Roussel, and C. J. Sherr. 1993. Overexpression of mouse D-type cyclins accelerates G1 phase in rodent fibroblasts. Genes & Devel 7:1559–1571.

45. Rosson, D. and E. P. Reddy. 1986. Nucleotide sequence of chicken c-myb complementary cDNA and implications for myb oncogene activation. Nature 319:604–606.

46. Serrano, M., E. Gomez-Lahoz, R. A. DePinho, D. Beach, and D. Bar-Sagi. 1995. Inhibition of ras-induced proliferation and cellular transformation by p16INK4. Science 267:249–252.

47. Sherr, C. J. 1993. Mammalian G1 cyclins: Review. Cell 73:1059–1065.

48. Sherr, C. J. 1994. G1 phase progression: cycling on cue. Cell 79:551–555.

49. Tice-Baldwin, K., G. R. Fink, and K. T. Arndt. 1989. BAS1 has a myb motif and activates HIS4 transcription only in combination with BAS2. Science 246:931–935.

50. Wasylyk, B., S. L. Hahn, and A. Giovane. 1993. The ets family of transcription factors. Eur J Biochem 211:7–18.

51. Weinberg, R. A. 1995. The retinoblastoma protein and cell cycle control. Cell 81:323–330.

52. Weston, K. and J. M. Bishop. 1989. Transcriptional activation by the v-myb oncogene and its cellular progenitor, c-myb. Cell 58:85–93.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications in addition to the immediately foregoing are cited herein, the disclosures of which are incorporated by reference in their entireties.

What is claimed is:

1. An isolated nucleic acid that encodes an amino acid polymer comprising an amino acid sequence that is greater then 75% identical to the amino acid sequence of SEQ ID NO:1; wherein the amino acid polymer:

(a) has a binding affinity for a D-type cyclin, in vitro;

(b) has a binding affinity for the nonamer consensus sequence CCCGTATGT; and (c) can act as a transcription factor involved in the activation of genes that prevent cell proliferation.

2. An isolated nucleic acid that encodes an amino acid polymer comprising an amino acid sequence that is greater then 75% identical to the amino acid sequence of SEQ ID NO:29; wherein the amino acid polymer:

(a) has a binding affinity for a D-type cyclin, in vitro;

(b) has a binding affinity for the nonamer consensus sequence CCCGTATGT; and (c) can act as a transcription factor involved in the activation of genes that prevent cell proliferation.

3. The nucleic acid of claim 1 wherein the amino acid polymer has the amino acid sequence SEQ ID NO:1, or SEQ ID NO:1 with one or more conservative amino acid substitutions.

4. The nucleic acid of claim 2 wherein the amino acid polymer is a human protein that is encoded on human chromosome 7 at a position which corresponds to $7_q21$; and contains about 760 amino acids, including the 262 amino acids of SEQ ID NO:24.

5. The nucleic acid of claim 4 wherein the nucleic acid comprises the coding region of the nucleotide sequence of SEQ ID NO:25.

6. An expression vector comprising the nucleic acid of claim 1 under the control of an expression control sequence, wherein the nucleic acid is a DNA.

7. An expression vector comprising the nucleic acid of claim 2 under the control of an expression control sequence, wherein the nucleic acid is a DNA.

8. An isolated nucleic acid having a nucleotide sequence selected from the group consisting of (a) a DNA sequence of SEQ ID NO:2;

(b) an RNA sequence corresponding to SEQ ID NO:3;

(c) a DNA sequence of SEQ ID NO:28;

(d) a RNA sequence of SEQ ID NO:30; and (e) a nucleotide sequence of at least 24 nucleotides that hybridizes to any of the foregoing nucleotide sequences under stringent hybridization conditions.

9. An expression vector having a recombinant gene or a cassette insertion site for a recombinant gene under the control of a transcription control sequence; wherein said transcription control sequence comprises the nonamer sequence CCCGTATGT.

10. An isolated nucleic acid comprising nucleotides −225 to +56 of FIG. 13, nucleotides 76–356 of SEQ ID NO:34.

11. An expression vector having a recombinant gene or a cassette insertion site for a recombinant gene under the control of a transcription control sequence; wherein said transcription control sequence comprises the nucleic acid of claim 10.

12. An isolated nucleic acid consisting of the nonamer sequence GACGGATGT (SEQ ID NO:35).

13. The nucleic acid of claim 12 further comprising a heterologous nucleotide sequence.

14. The nucleic acid of claim 8 further comprising a heterologous nucleotide sequence.

15. The nucleic acid of claim 1 wherein the nucleic acid comprises the coding region of the nucleotide sequence of SEQ ID NO:2.

16. An expression vector comprising the nucleic acid of claim 15 under the control of an expression control sequence, wherein the nucleic acid is a DNA.

17. A cell comprising the expression vector of claim 16.

18. An expression vector comprising the nucleic acid of claim 5 under the control of an expression control sequence, wherein the nucleic acid is a DNA.

19. A cell comprising the expression vector of claim 18.

20. The nucleic acid of claim 2 further comprising a heterologous nucleotide sequence.

21. The nucleic acid of claim 1 further comprising a heterologous nucleotide sequence.

22. A nucleic acid encoding a DNA-binding domain of DMP1; wherein the DNA-binding domain comprises an amino acid sequence selected from the group consisting of SEQ ID NO:16, SEQ ID NO:16 comprising one or more conservative amino acid substitutions; amino acids 87–458 of SEQ ID NO:29, and amino acids 87–458 of SEQ ID NO:29 comprising one or more conservative amino acid substitutions; wherein the DNA-binding domain has a binding affinity for the nonamer consensus sequence CCCGTATGT.

23. The nucleic acid of claim 22 having the nucleic acid sequence of SEQ ID NO:17.

24. The nucleic acid of claim 22 further comprising a heterologous nucleotide sequence.

25. A nucleic acid encoding a cyclin binding domain of DMP1; wherein the cyclin binding domain comprises an amino acid sequence selected from the group consisting of SEQ ID NO:22, SEQ ID NO:22 comprising one or more conservative amino acid substitutions; amino acids 1–223 of SEQ ID NO:29, and amino acids 1–223 of SEQ ID NO:29 comprising one or more conservative amino acid substitutions; wherein the cyclin binding domain has a binding affinity for a D-type cyclin, in vitro.

26. The nucleic acid of claim 25 having the nucleic acid sequence of SEQ ID NO:23.

27. The nucleic acid of claim 25 further comprising a heterologous nucleotide sequence.

28. A nucleic acid encoding a transactivation domain; wherein the transactivation domain comprises an amino acid sequence selected from the group consisting of SEQ ID NO:18, SEQ ID NO:18 comprising one or more conservative amino acid substitutions; amino acids 459–760 of SEQ ID NO:29, or amino acids 459–760 of SEQ ID NO:29 comprising one or more conservative amino acid substitutions; wherein the transactivation domain can stimulate the expression of the genes under control of DMP1-responsive promoters.

29. The nucleic acid of claim 28 having the nucleic acid sequence of SEQ ID NO:19.

30. The nucleic acid of claim 28 further comprising a heterologous nucleotide sequence.

31. A nucleic acid encoding an N-terminal fragment of the amino acid polymer; wherein the N-terminal fragment comprises SEQ ID NO:20, or SEQ ID NO:20 comprising a conservative amino acid substitution.

32. The nucleic acid of claim 31 having the nucleic acid sequence of SEQ ID NO:21.

33. The nucleic acid of claim 31 further comprising a heterologous nucleotide sequence.

34. A nucleic acid which encodes three myb repeats of DMP1; wherein the three myb repeats comprise the amino acid sequence of SEQ ID NO:45, or SEQ ID NO:45 comprising a conservative amino acid substitution.

35. The nucleic acid of claim 34 further comprising a heterologous nucleotide sequence.

36. A fragment of the nucleic acid of claim 2 which encodes a C-terminal fragment of the amino acid polymer; wherein the C-terminal fragment comprises SEQ ID NO:24, or SEQ ID NO:24 comprising a conservative amino acid substitution.

37. The nucleic acid fragment of claim 36 further comprising a heterologous nucleotide sequence.

38. The nucleic acid of claim 2 wherein the amino acid polymer is a human protein that has the amino acid sequence SEQ ID NO:29, or SEQ ID NO:29 with one or more conservative amino acid substitutions.

39. The nucleic acid of claim 38 wherein the nucleic acid comprises the coding region of the nucleotide sequence of SEQ ID NO:28.

40. The nucleic acid of claim 9 further comprising a heterologous nucleotide sequence.

41. A nucleic acid that encodes an amino acid polymer comprising the amino acid sequence of SEQ ID NO:1 except the lysine at position 319 of SEQ ID NO:1 is replaced by a glutamic acid.

42. The nucleic acid of claim 41 further comprising a heterologous nucleotide sequence.

43. An expression vector having a recombinant gene or a cassette insertion site for a recombinant gene under the control of a transcription control sequence; wherein said transcription control sequence comprises the nucleic acid of claim 40.

44. An expression vector having a recombinant gene or a cassette insertion site for a recombinant gene under the control of a transcription control sequence; wherein said transcription control sequence comprises the nucleic acid of claim 13.

45. An isolated nucleic acid consisting of the nonamer sequence CCCGGATGC (SEQ ID NO:33).

* * * * *

SEQUENCE LISTING (1) GENERAL INFORMATION:

(iii) NUMBER OF SEQUENCES: 46

(2) INFORMATION FOR SEQ ID NO: 1:

(i) SEQUENCE CHARACTERISTICS:
(A) LENGTH: 761 amino acids
(B) TYPE: amino acid
(C) STRANDEDNESS: <Unknown>
(D) TOPOLOGY: linear (ii) MOLECULE TYPE: protein (iii) HYPOTHETICAL: YES (v) FRAGMENT TYPE: <Unknown>

(vi) ORIGINAL SOURCE:
(A) ORGANISM: Mus musculus (xi) SEQUENCE DESCRIPTION: SEQ ID NO: 1:

```
Met Ser Thr Val Glu Glu Asp Ser Asp Thr Val Thr Val Glu Thr Val
1               5                   10                  15

Asn Ser Val Thr Phe Thr Gln Asp Thr Asp Gly Asn Leu Ile Leu His
            20                  25                  30

Cys Pro Gln Asn Asp Pro Asp Glu Val Asp Ser Glu Asp Ser Thr Glu
        35                  40                  45

Pro Pro His Lys Arg Leu Cys Leu Ser Ser Glu Asp Asp Gln Ser Ile
    50                  55                  60

Asp Asp Ala Thr Pro Cys Ile Ser Val Val Ala Leu Pro Leu Ser Glu
65                  70                  75                  80

Asn Asp Gln Ser Phe Glu Val Thr Met Thr Ala Thr Thr Glu Val Ala
                85                  90                  95

Asp Asp Glu Leu Ser Glu Gly Thr Val Thr Gln Ile Gln Ile Leu Gln
            100                 105                 110

Asn Asp Gln Leu Asp Glu Ile Ser Pro Leu Gly Thr Glu Glu Val Ser
        115                 120                 125

Ala Val Ser Gln Ala Trp Phe Thr Thr Lys Glu Asp Lys Asp Ser Leu
    130                 135                 140

Thr Asn Lys Gly His Lys Trp Lys Gln Gly Met Trp Ser Lys Glu Glu
145                 150                 155                 160

Ile Asp Ile Leu Met Asn Asn Ile Glu Arg Tyr Leu Lys Ala Arg Gly
                165                 170                 175

Ile Lys Asp Ala Thr Glu Ile Ile Phe Glu Met Ser Lys Asp Glu Arg
            180                 185                 190

Lys Asp Phe Tyr Arg Thr Ile Ala Trp Gly Leu Asn Arg Pro Leu Phe
        195                 200                 205

Ala Val Tyr Arg Arg Val Leu Arg Met Tyr Asp Asp Arg Asn His Val
    210                 215                 220

Gly Lys Tyr Thr Pro Glu Glu Ile Glu Lys Leu Lys Glu Leu Arg Ile
225                 230                 235                 240

Lys His Gly Asn Asp Trp Ala Thr Ile Gly Ala Ala Leu Gly Arg Ser
                245                 250                 255

Ala Ser Ser Val Lys Asp Arg Cys Arg Leu Met Lys Asp Thr Cys Asn
            260                 265                 270

Thr Gly Lys Trp Thr Glu Glu Glu Glu Lys Arg Leu Ala Glu Val Val
```

-continued

```
        275                 280                 285

His Glu Leu Thr Ser Thr Glu Pro Gly Asp Ile Val Thr Gln Gly Val
    290                 295                 300

Ser Trp Ala Ala Val Ala Glu Arg Val Gly Thr Arg Ser Glu Lys Gln
305                 310                 315                 320

Cys Arg Ser Lys Trp Leu Asn Tyr Leu Asn Trp Lys Gln Ser Gly Gly
                325                 330                 335

Thr Glu Trp Thr Lys Glu Asp Glu Ile Asn Leu Ile Leu Arg Ile Ala
            340                 345                 350

Glu Leu Asp Val Ala Asp Glu Asn Asp Ile Asn Trp Asp Leu Leu Ala
        355                 360                 365

Glu Gly Trp Ser Ser Val Arg Ser Pro Gln Trp Leu Arg Ser Lys Trp
    370                 375                 380

Trp Thr Ile Lys Arg Gln Ile Ala Asn His Lys Asp Val Ser Phe Pro
385                 390                 395                 400

Val Leu Ile Lys Gly Leu Lys Gln Leu His Glu Asn Gln Lys Asn Asn
                405                 410                 415

Pro Val Leu Leu Glu Asn Lys Ser Gly Ser Gly Val Pro Asn Ser Asn
            420                 425                 430

Cys Asn Ser Ser Val Gln His Val Gln Ile Arg Val Ala Arg Leu Glu
        435                 440                 445

Asp Asn Thr Ala Ile Ser Pro Ser Pro Met Ala Ala Leu Gln Ile Pro
    450                 455                 460

Val Gln Ile Thr His Val Ser Ser Thr Asp Ser Pro Ala Ala Ser Ala
465                 470                 475                 480

Asp Ser Glu Thr Ile Thr Leu Asn Ser Gly Thr Leu Gln Thr Phe Glu
                485                 490                 495

Ile Leu Pro Ser Phe Pro Leu Gln Pro Thr Gly Thr Pro Gly Thr Tyr
            500                 505                 510

Leu Leu Gln Thr Ser Ser Ser Gln Gly Leu Pro Leu Thr Leu Thr Thr
        515                 520                 525

Asn Pro Thr Leu Thr Leu Ala Ala Ala Ala Pro Ala Ser Pro Glu Gln
    530                 535                 540

Ile Ile Val His Ala Leu Ser Pro Glu His Leu Leu Asn Thr Ser Asp
545                 550                 555                 560

Asn Val Thr Val Gln Cys His Thr Pro Arg Val Ile Ile Gln Thr Val
                565                 570                 575

Ala Thr Glu Asp Ile Thr Ser Ser Leu Ser Gln Glu Glu Leu Thr Val
            580                 585                 590

Asp Ser Asp Leu His Ser Ser Asp Phe Pro Glu Pro Pro Asp Ala Leu
        595                 600                 605

Glu Ala Asp Thr Phe Pro Asp Glu Ile Pro Arg Pro Lys Met Thr Ile
    610                 615                 620

Gln Pro Ser Phe Asn Asn Ala His Val Ser Lys Phe Ser Asp Gln Asn
625                 630                 635                 640

Ser Thr Glu Leu Met Asn Ser Val Met Val Arg Thr Glu Glu Glu Ile
                645                 650                 655

Ala Asp Thr Asp Leu Lys Gln Glu Glu Pro Pro Ser Asp Leu Ala Ser
            660                 665                 670

Ala Tyr Val Thr Glu Asp Leu Glu Ser Pro Thr Ile Val His Gln Val
        675                 680                 685

His Gln Thr Ile Asp Asp Glu Thr Ile Leu Ile Val Pro Ser Pro His
    690                 695                 700
```

-continued

```
Gly Phe Ile Gln Ala Ser Asp Val Ile Asp Thr Glu Ser Val Leu Pro
705                 710                 715                 720

Leu Thr Thr Leu Thr Asp Pro Ile Phe Gln His His Gln Glu Ala Ser
                725                 730                 735

Asn Ile Ile Gly Ser Ser Leu Gly Ser Pro Val Ser Glu Asp Ser Lys
            740                 745                 750

Asp Val Glu Asp Leu Val Asn Cys His
        755                 760
```

(2) INFORMATION FOR SEQ ID NO: 2:

(i) SEQUENCE CHARACTERISTICS:
(A) LENGTH: 2903 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Mus musculus (ix) FEATURE:
(A) NAME/KEY: CDS
(B) LOCATION: 248..2533
(D) OTHER INFORMATION: /codon_start= 248
/product= "DMP-1"

(xi) SEQUENCE DESCRIPTION: SEQ ID NO: 2:

```
GAATCCGGCT CGCTCACCCC AGCTGCAGCC ACTCTCTCCC GCGGCTGCTT CCTCCATCCT     60

GGTATTTTTT GGAGCCTCCA TCCTGGTTCT TCCAAAGTGC CCGGACCCAA AACAGGAAAG    120

GATCACAGAT GCACAAGCAT GGAGGAGAAG CAGTCTGGTT AACGTGAGTG ATGCTGCTGG    180

CCGAAGCACA GAGGTGGGAT TCTATGGGAA GGCCTGTAGC TAATCCACCT GTGGTCTAGA    240

TTTGAGTATG AGCACAGTTG AAGAGGATTC TGACACAGTA ACAGTAGAAA CTGTGAACTC    300

TGTGACGTTT ACTCAGGACA CGGACGGGAA TCTCATTCTT CATTGCCCTC AGAATGACCC    360

TGATGAAGTA GACTCAGAAG ACAGTACTGA ACCTCCACAT AAGAGGCTTT GTTTGTCCTC    420

TGAGGATGAT CAAAGCATTG ATGACGCTAC GCCATGCATA TCAGTCGTGG CACTCCCACT    480

TTCAGAAAAT GATCAGAGCT TTGAGGTGAC CATGACGGCA ACTACAGAGG TGGCAGATGA    540

TGAACTTTCT GAGGGAACTG TGACACAAAT TCAGATTTTA CAGAATGATC AACTAGATGA    600

AATATCTCCA TTGGGTACTG AGGAAGTCTC AGCAGTTAGC CAAGCGTGGT TTACAACTAA    660

AGAAGATAAG GATTCTCTCA CTAACAAAGG ACATAAATGG AAGCAGGGGA TGTGGTCCAA    720

GGAAGAAATT GATATTTTAA TGAACAACAT CGAGCGCTAT CTGAAGGCTC GCGGAATAAA    780

AGATGCTACA GAAATCATCT TTGAGATGTC AAAAGACGAA AGAAAAGATT TCTACAGGAC    840

TATAGCGTGG GGGCTGAACC GGCCTTTGTT TGCAGTTTAT AGAAGAGTGC TGCGCATGTA    900

TGATGACAGG AACCATGTGG GAAAATACAC TCCTGAAGAG ATCGAGAAGC TCAAGGAGCT    960

CCGGATAAAA CACGGCAATG ACTGGGCAAC AATAGGGGCG GCCCTAGGAA GAAGCGCCTC   1020

TTCTGTCAAA GACCGCTGCC GGCTGATGAA GGATACCTGC AACACAGGGA AATGGACAGA   1080

AGAAGAAGAA AAGAGACTTG CAGAGGTAGT TCATGAATTA ACAAGCACGG AGCCAGGTGA   1140

CATCGTCACA CAGGGTGTGT CTTGGGCAGC TGTAGCTGAA AGAGTGGGTA CCCGCTCAGA   1200
```

-continued

```
AAAGCAATGC CGTTCTAAAT GGCTCAACTA CCTGAACTGG AAGCAGAGTG GGGGTACTGA   1260

ATGGACCAAG GAAGATGAAA TCAATCTCAT CCTAAGGATA GCTGAGCTTG ATGTGGCCGA   1320

TGAAAATGAC ATAAACTGGG ATCTTTTAGC TGAAGGATGG AGCAGTGTCC GTTCACCACA   1380

GTGGCTTCGA AGTAAATGGT GGACCATCAA AAGGCAAATT GCAAACCATA AGGATGTTTC   1440

ATTTCCTGTC CTAATAAAAG GTCTTAAACA GTTACATGAG AACCAAAAAA ACAACCCAGT   1500

GCTTTTGGAG AATAAATCAG GATCTGGAGT TCCAAACAGT AATTGCAATT CCAGTGTACA   1560

GCATGTTCAG ATCAGAGTCG CCCGCTTGGA AGATAATACA GCCATCTCTC CAAGCCCCAT   1620

GGCAGCGTTG CAGATTCCAG TCCAGATCAC CCACGTCTCT TCAACAGACT CCCCTGCTGC   1680

TTCTGCCGAC TCAGAAACAA TCACACTAAA CAGTGGAACA CTACAAACAT TTGAGATTCT   1740

TCCATCTTTT CCATTACAGC CCACTGGTAC TCCAGGCACC TACCTTCTTC AAACAAGCTC   1800

AAGTCAAGGC CTTCCCCTAA CACTGACCAC AAATCCCACA CTAACCCTGG CAGCTGCTGC   1860

TCCTGCTTCT CCTGAACAGA TCATTGTTCA TGCTTTATCC CCAGAACATT TGTTGAACAC   1920

AAGCGATAAT GTCACGGTAC AATGTCACAC ACCAAGAGTC ATCATTCAGA CGGTAGCTAC   1980

AGAGGACATC ACTTCTTCAT TATCCCAAGA GGAACTGACA GTTGATAGTG ATCTTCATTC   2040

ATCTGATTTC CCTGAGCCTC CAGATGCACT AGAAGCAGAC ACTTTCCCAG ACGAAATTCC   2100

TCGGCCTAAG ATGACTATAC AACCATCATT TAATAATGCT CATGTATCTA AATTCAGCGA   2160

CCAAAATAGC ACAGAACTGA TGAACAGTGT CATGGTCAGA ACAGAGGAAG AAATTGCCGA   2220

CACTGACCTT AAGCAGGAAG AACCGCCGTC TGACTTAGCC AGTGCTTATG TTACTGAGGA   2280

TTTAGAGTCT CCCACCATAG TGCACCAAGT TCATCAGACA ATTGATGATG AAACAATACT   2340

TATCGTTCCT TCACCTCATG GCTTTATCCA GGCATCTGAT GTTATAGATA CTGAATCTGT   2400

CTTGCCTTTG ACAACACTAA CAGATCCAAT ATTCCAGCAT CATCAGGAAG CATCAAATAT   2460

AATTGGATCA TCTTTGGGCA GTCCTGTTTC TGAAGACTCA AAGGATGTTG AGGACTTAGT   2520

AAACTGTCAC TAGATTATTA GAAACAGGTA CTTCAAGAAG CCACATTGTG ACTACATTGT   2580

CTCCAAAGAA AGGAGCCATC CCAGGAGTTG TGGTTTGCCA TTCCTCTGGC TTGTACTTAG   2640

CTGCCATGCT TAAGCCATGC ACATTGTTGC TGCTGTTACT TTTACCTCCT TCTCAGTAGA   2700

TCATCTAGGG TCCAATTTTA TAACAGTTGT TATGATGGAG GATAGGAAGT GTGAATTGCC   2760

CAGACTTGTT AGGTTTTATG TCAAGAGGGA GTTGCAGTCA CTGCAGCTAC TTATCATCAC   2820

CAGAGCTTAA CTACTCTGGT TTAAATATAA GTAGTAATAG TGATCTCTGC AGTTAGACAC   2880

ACAGCTCTCG TCCAGACTCA AGC                                           2903
```

(2) INFORMATION FOR SEQ ID NO: 3:

(i) SEQUENCE CHARACTERISTICS:
(A) LENGTH: 2903 base pairs
(B) TYPE: nucleic acid
(C) STRANDEDNESS: single
(D) TOPOLOGY: linear (ii) MOLECULE TYPE: cDNA to mRNA (iii) HYPOTHETICAL: YES (iv) ANTI-SENSE: NO (vi) ORIGINAL SOURCE:
(A) ORGANISM: Mus musculus (xi) SEQUENCE DESCRIPTION: SEQ ID NO: 3:

```
GAAUCCGGCU CGCUCACCCC AGCUGCAGCC ACUCUCUCCC GCGGCUGCUU CCUCCAUCCU     60
```

-continued

```
GGUAUUUUUU GGAGCCUCCA UCCUGGUUCU UCCAAAGUGC CCGGACCCAA AACAGGAAAG    120
GAUCACAGAU GCACAAGCAU GGAGGAGAAG CAGUCUGGUU AACGUGAGUG AUGCUGCUGG    180
CCGAAGCACA GAGGUGGGAU UCUAUGGGAA GGCCUGUAGC UAAUCCACCU GUGGUCUAGA    240
UUUGAGUAUG AGCACAGUUG AAGAGGAUUC UGACACAGUA ACAGUAGAAA CUGUGAACUC    300
UGUGACGUUU ACUCAGGACA CGGACGGGAA UCUCAUUCUU CAUUGCCCUC AGAAUGACCC    360
UGAUGAAGUA GACUCAGAAG ACAGUACUGA ACCUCCACAU AAGAGGCUUU GUUUGUCCUC    420
UGAGGAUGAU CAAAGCAUUG AUGACGCUAC GCCAUGCAUA UCAGUCGUGG CACUCCCACU    480
UUCAGAAAAU GAUCAGAGCU UUGAGGUGAC CAUGACGGCA ACUACAGAGG UGGCAGAUGA    540
UGAACUUUCU GAGGGAACUG UGACACAAAU UCAGAUUUUA CAGAAUGAUC AACUAGAUGA    600
AAUAUCUCCA UUGGGUACUG AGGAAGUCUC AGCAGUUAGC CAAGCGUGGU UUACAACUAA    660
AGAAGAUAAG GAUUCUCUCA CUAACAAAGG ACAUAAAUGG AAGCAGGGGA UGUGGUCCAA    720
GGAAGAAAUU GAUAUUUUAA UGAACAACAU CGAGCGCUAU CUGAAGGCUC GCGGAAUAAA    780
AGAUGCUACA GAAAUCAUCU UUGAGAUGUC AAAAGACGAA AGAAAAGAUU UCUACAGGAC    840
UAUAGCGUGG GGGCUGAACC GGCCUUUGUU UGCAGUUUAU AGAAGAGUGC UGCGCAUGUA    900
UGAUGACAGG AACCAUGUGG GAAAAUACAC UCCUGAAGAG AUCGAGAAGC UCAAGGAGCU    960
CCGGAUAAAA CACGGCAAUG ACUGGGCAAC AAUAGGGGCG GCCCUAGGAA GAAGCGCCUC   1020
UUCUGUCAAA GACCGCUGCC GGCUGAUGAA GGAUACCUGC AACACAGGGA AAUGGACAGA   1080
AGAAGAAGAA AAGAGACUUG CAGAGGUAGU UCAUGAAUUA ACAAGCACGG AGCCAGGUGA   1140
CAUCGUCACA CAGGGUGUGU CUUGGGCAGC UGUAGCUGAA AGAGUGGGUA CCCGCUCAGA   1200
AAAGCAAUGC CGUUCUAAAU GGCUCAACUA CCUGAACUGG AAGCAGAGUG GGGGUACUGA   1260
AUGGACCAAG GAAGAUGAAA UCAAUCUCAU CCUAAGGAUA GCUGAGCUUG AUGUGGCCGA   1320
UGAAAAUGAC AUAAACUGGG AUCUUUUAGC UGAAGGAUGG AGCAGUGUCC GUUCACCACA   1380
GUGGCUUCGA AGUAAAUGGU GGACCAUCAA AAGGCAAAUU GCAAACCAUA AGGAUGUUUC   1440
AUUUCCUGUC CUAAUAAAAG GUCUUAAACA GUUACAUGAG AACCAAAAAA ACAACCCAGU   1500
GCUUUUGGAG AAUAAAUCAG GAUCUGGAGU UCCAAACAGU AAUUGCAAUU CCAGUGUACA   1560
GCAUGUUCAG AUCAGAGUCG CCCGCUUGGA AGAUAAUACA GCCAUCUCUC CAAGCCCCAU   1620
GGCAGCGUUG CAGAUUCCAG UCCAGAUCAC CCACGUCUCU UCAACAGACU CCCCUGCUGC   1680
UUCUGCCGAC UCAGAAACAA UCACACUAAA CAGUGGAACA CUACAAACAU UUGAGAUUCU   1740
UCCAUCUUUU CCAUUACAGC CCACUGGUAC UCCAGGCACC UACCUUCUUC AAACAAGCUC   1800
AAGUCAAGGC CUUCCCCUAA CACUGACCAC AAAUCCCACA CUAACCCUGG CAGCUGCUGC   1860
UCCUGCUUCU CCUGAACAGA UCAUUGUUCA UGCUUUAUCC CCAGAACAUU UGUUGAACAC   1920
AAGCGAUAAU GUCACGGUAC AAUGUCACAC ACCAAGAGUC AUCAUUCAGA CGGUAGCUAC   1980
AGAGGACAUC ACUUCUUCAU UAUCCCAAGA GGAACUGACA GUUGAUAGUG AUCUUCAUUC   2040
AUCUGAUUUC CCUGAGCCUC CAGAUGCACU AGAAGCAGAC ACUUUCCCAG ACGAAAUUCC   2100
UCGGCCUAAG AUGACUAUAC AACCAUCAUU UAAUAAUGCU CAUGUAUCUA AAUUCAGCGA   2160
CCAAAAUAGC ACAGAACUGA UGAACAGUGU CAUGGUCAGA ACAGAGGAAG AAAUUGCCGA   2220
CACUGACCUU AAGCAGGAAG AACCGCCGUC UGACUUAGCC AGUGCUUAUG UUACUGAGGA   2280
UUUAGAGUCU CCCACCAUAG UGCACCAAGU UCAUCAGACA AUUGAUGAUG AAACAAUACU   2340
UAUCGUUCCU UCACCUCAUG GCUUUAUCCA GGCAUCUGAU GUUAUAGAUA CUGAAUCUGU   2400
```

-continued

```
CUUGCCUUUG ACAACACUAA CAGAUCCAAU AUUCCAGCAU CAUCAGGAAG CAUCAAAUAU   2460

AAUUGGAUCA UCUUUGGGCA GUCCUGUUUC UGAAGACUCA AAGGAUGUUG AGGACUUAGU   2520

AAACUGUCAC UAGAUUAUUA GAAACAGGUA CUUCAAGAAG CCACAUUGUG ACUACAUUGU   2580

CUCCAAAGAA AGGAGCCAUC CCAGGAGUUG UGGUUUGCCA UUCCUCUGGC UUGUACUUAG   2640

CUGCCAUGCU UAAGCCAUGC ACAUUGUUGC UGCUGUUACU UUUACCUCCU UCUCAGUAGA   2700

UCAUCUAGGG UCCAAUUUUA UAACAGUUGU UAUGAUGGAG GAUAGGAAGU GUGAAUUGCC   2760

CAGACUUGUU AGGUUUUAUG UCAAGAGGGA GUUGCAGUCA CUGCAGCUAC UUAUCAUCAC   2820

CAGAGCUUAA CUACUCUGGU UUAAAUAUAA GUAGUAAUAG UGAUCUCUGC AGUUAGACAC   2880

ACAGCUCUCG UCCAGACUCA AGC                                           2903
```

(2) INFORMATION FOR SEQ ID NO: 4:

(i) SEQUENCE CHARACTERISTICS:
(A) LENGTH: 156 amino acids
(B) TYPE: amino acid
(C) STRANDEDNESS: <Unknown>
(D) TOPOLOGY: linear (ii) MOLECULE TYPE: protein (iii) HYPOTHETICAL: NO (v) FRAGMENT TYPE: internal (vi) ORIGINAL SOURCE:
(A) ORGANISM: Mus musculus (xi) SEQUENCE DESCRIPTION: SEQ ID NO: 4:

```
Leu Gly Lys Thr Arg Trp Thr Arg Glu Glu Asp Glu Lys Leu Lys Lys
1               5                   10                  15

Leu Val Glu Gln Asn Gly Thr Asp Asp Trp Lys Val Ile Ala Asn Tyr
            20                  25                  30

Leu Pro Asn Arg Thr Asp Val Gln Cys Gln His Arg Trp Gln Lys Val
        35                  40                  45

Leu Asn Pro Glu Leu Ile Lys Gly Pro Trp Thr Lys Glu Glu Asp Gln
    50                  55                  60

Arg Val Ile Lys Leu Val Gln Lys Tyr Gly Pro Lys Arg Trp Ser Val
65                  70                  75                  80

Ile Ala Lys His Leu Lys Gly Arg Ile Gly Lys Gln Cys Arg Glu Arg
                85                  90                  95

Trp His Asn His Leu Asn Pro Glu Val Lys Lys Thr Ser Trp Thr Glu
            100                 105                 110

Glu Glu Asp Arg Ile Ile Tyr Gln Ala His Lys Arg Leu Gly Asn Arg
        115                 120                 125

Trp Ala Glu Ile Ala Lys Leu Leu Pro Gly Arg Thr Asp Asn Ala Ile
    130                 135                 140

Lys Asn His Trp Asn Ser Thr Met Arg Arg Lys Val
145                 150                 155
```

(2) INFORMATION FOR SEQ ID NO: 5:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = “primer”

-continued (iii) HYPOTHETICAL: NO (xi) SEQUENCE DESCRIPTION: SEQ ID NO: 5:

CGCGGATCCT GCAGCTCGAG 20

(2) INFORMATION FOR SEQ ID NO: 6:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = “primer”

(iii) HYPOTHETICAL: NO (xi) SEQUENCE DESCRIPTION: SEQ ID NO: 6:

TGCTCTAGAA GCTTGTCGAC 20

(2) INFORMATION FOR SEQ ID NO: 7:

(i) SEQUENCE CHARACTERISTICS:
(A) LENGTH: 4 amino acids
(B) TYPE: amino acid
(C) STRANDEDNESS: single
(D) TOPOLOGY: unknown (ii) MOLECULE TYPE: peptide (iii) HYPOTHETICAL: NO (v) FRAGMENT TYPE: internal (xi) SEQUENCE DESCRIPTION: SEQ ID NO: 7:

Ser Pro Xaa Glx
1

(2) INFORMATION FOR SEQ ID NO: 8:

(i) SEQUENCE CHARACTERISTICS:
(A) LENGTH: 9 amino acids
(B) TYPE: amino acid
(C) STRANDEDNESS: <Unknown>
(D) TOPOLOGY: unknown (ii) MOLECULE TYPE: peptide (iii) HYPOTHETICAL: NO (v) FRAGMENT TYPE: internal (xi) SEQUENCE DESCRIPTION: SEQ ID NO: 8:

Lys Gln Cys Arg Xaa Xaa Trp Xaa Asn
1 5

(2) INFORMATION FOR SEQ ID NO: 9:

(i) SEQUENCE CHARACTERISTICS:
(A) LENGTH: 5 amino acids
(B) TYPE: amino acid
(C) STRANDEDNESS: <Unknown>
(D) TOPOLOGY: unknown (ii) MOLECULE TYPE: peptide (iii) HYPOTHETICAL: NO (v) FRAGMENT TYPE: internal -continued (xi) SEQUENCE DESCRIPTION: SEQ ID NO: 9:

Leu Xaa Cys Xaa Glu
1 5

(2) INFORMATION FOR SEQ ID NO: 10:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "probe/competitor BS1"

(iii) HYPOTHETICAL: NO (xi) SEQUENCE DESCRIPTION: SEQ ID NO: 10:

AATTGACCCG GATGTAGGTA CGC 23

(2) INFORMATION FOR SEQ ID NO: 11:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "probe/competitor BS2"

(iii) HYPOTHETICAL: NO (xi) SEQUENCE DESCRIPTION: SEQ ID NO: 11:

AATTGACCCG TATGTAGGTA CGC 23

(2) INFORMATION FOR SEQ ID NO: 12:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "probe/competitor M1"

(iii) HYPOTHETICAL: NO (xi) SEQUENCE DESCRIPTION: SEQ ID NO: 12:

AATTGACCCT GCGGTAGGTA CGC 23

(2) INFORMATION FOR SEQ ID NO: 13:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "probe/competitor M2"

(iii) HYPOTHETICAL: NO (xi) SEQUENCE DESCRIPTION: SEQ ID NO: 13:

AATTGATTTG GATGTAGGTA CGC 23

-continued (2) INFORMATION FOR SEQ ID NO: 14:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "probe/competitor M3"

(iii) HYPOTHETICAL: NO (xi) SEQUENCE DESCRIPTION: SEQ ID NO: 14:

AATTGACCCG GAAGTAGGTA CGC 23

(2) INFORMATION FOR SEQ ID NO: 15:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "probe/competitor M4"

(iii) HYPOTHETICAL: NO (xi) SEQUENCE DESCRIPTION: SEQ ID NO: 15:

AATTGACCAG GATGTAGGTA CGC 23

(2) INFORMATION FOR SEQ ID NO: 16:

(i) SEQUENCE CHARACTERISTICS:
(A) LENGTH: 372 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Mus musculus (xi) SEQUENCE DESCRIPTION: SEQ ID NO: 16:

```
Val Thr Met Thr Ala Thr Thr Glu Val Ala Asp Asp Glu Leu Ser Glu
1               5                   10                  15

Gly Thr Val Thr Gln Ile Gln Ile Leu Gln Asn Asp Gln Leu Asp Glu
            20                  25                  30

Ile Ser Pro Leu Gly Thr Glu Glu Val Ser Ala Val Ser Gln Ala Trp
        35                  40                  45

Phe Thr Thr Lys Glu Asp Lys Asp Ser Leu Thr Asn Lys Gly His Lys
    50                  55                  60

Trp Lys Gln Gly Met Trp Ser Lys Glu Glu Ile Asp Ile Leu Met Asn
65                  70                  75                  80

Asn Ile Glu Arg Tyr Leu Lys Ala Arg Gly Ile Lys Asp Ala Thr Glu
                85                  90                  95

Ile Ile Phe Glu Met Ser Lys Asp Glu Arg Lys Asp Phe Tyr Arg Thr
            100                 105                 110

Ile Ala Trp Gly Leu Asn Arg Pro Leu Phe Ala Val Tyr Arg Arg Val
        115                 120                 125
```

-continued

```
Leu Arg Met Tyr Asp Asp Arg Asn His Val Gly Lys Tyr Thr Pro Glu
    130                 135                 140

Glu Ile Glu Lys Leu Lys Glu Leu Arg Ile Lys His Gly Asn Asp Trp
145                 150                 155                 160

Ala Thr Ile Gly Ala Ala Leu Gly Arg Ser Ala Ser Ser Val Lys Asp
                165                 170                 175

Arg Cys Arg Leu Met Lys Asp Thr Cys Asn Thr Gly Lys Trp Thr Glu
            180                 185                 190

Glu Glu Glu Lys Arg Leu Ala Glu Val Val His Glu Leu Thr Ser Thr
        195                 200                 205

Glu Pro Gly Asp Ile Val Thr Gln Gly Val Ser Trp Ala Ala Val Ala
    210                 215                 220

Glu Arg Val Gly Thr Arg Ser Glu Lys Gln Cys Arg Ser Lys Trp Leu
225                 230                 235                 240

Asn Tyr Leu Asn Trp Lys Gln Ser Gly Gly Thr Glu Trp Thr Lys Glu
                245                 250                 255

Asp Glu Ile Asn Leu Ile Leu Arg Ile Ala Glu Leu Asp Val Ala Asp
            260                 265                 270

Glu Asn Asp Ile Asn Trp Asp Leu Leu Ala Glu Gly Trp Ser Ser Val
        275                 280                 285

Arg Ser Pro Gln Trp Leu Arg Ser Lys Trp Trp Thr Ile Lys Arg Gln
    290                 295                 300

Ile Ala Asn His Lys Asp Val Ser Phe Pro Val Leu Ile Lys Gly Leu
305                 310                 315                 320

Lys Gln Leu His Glu Asn Gln Lys Asn Asn Pro Val Leu Leu Glu Asn
                325                 330                 335

Lys Ser Gly Ser Gly Val Pro Asn Ser Asn Cys Asn Ser Ser Val Gln
            340                 345                 350

His Val Gln Ile Arg Val Ala Arg Leu Glu Asp Asn Thr Ala Ile Ser
        355                 360                 365

Pro Ser Pro Met
    370
```

(2) INFORMATION FOR SEQ ID NO: 17:

(i) SEQUENCE CHARACTERISTICS:
(A) LENGTH: 1116 base pairs
(B) TYPE: nucleic acid
(C) STRANDEDNESS: double
(D) TOPOLOGY: linear (ii) MOLECULE TYPE: cDNA (iii) HYPOTHETICAL: NO (vi) ORIGINAL SOURCE:
(A) ORGANISM: Mus musculus (xi) SEQUENCE DESCRIPTION: SEQ ID NO: 17:

```
GTGACCATGA CGGCAACTAC AGAGGTGGCA GATGATGAAC TTTCTGAGGG AACTGTGACA     60

CAAATTCAGA TTTTACAGAA TGATCAACTA GATGAAATAT CTCCATTGGG TACTGAGGAA    120

GTCTCAGCAG TTAGCCAAGC GTGGTTTACA ACTAAAGAAG ATAAGGATTC TCTCACTAAC    180

AAAGGACATA AATGGAAGCA GGGGATGTGG TCCAAGGAAG AAATTGATAT TTTAATGAAC    240

AACATCGAGC GCTATCTGAA GGCTCGCGGA ATAAAAGATG CTACAGAAAT CATCTTTGAG    300

ATGTCAAAAG ACGAAAGAAA AGATTTCTAC AGGACTATAG CGTGGGGGCT GAACCGGCCT    360

TTGTTTGCAG TTTATAGAAG AGTGCTGCGC ATGTATGATG ACAGGAACCA TGTGGGAAAA    420
```

-continued

```
TACACTCCTG AAGAGATCGA GAAGCTCAAG GAGCTCCGGA TAAAACACGG CAATGACTGG    480

GCAACAATAG GGGCGGCCCT AGGAAGAAGC GCCTCTTCTG TCAAAGACCG CTGCCGGCTG    540

ATGAAGGATA CCTGCAACAC AGGGAAATGG ACAGAAGAAG AAGAAAAGAG ACTTGCAGAG    600

GTAGTTCATG AATTAACAAG CACGGAGCCA GGTGACATCG TCACACAGGG TGTGTCTTGG    660

GCAGCTGTAG CTGAAAGAGT GGGTACCCGC TCAGAAAAGC AATGCCGTTC TAAATGGCTC    720

AACTACCTGA ACTGGAAGCA GAGTGGGGGT ACTGAATGGA CCAAGGAAGA TGAAATCAAT    780

CTCATCCTAA GGATAGCTGA GCTTGATGTG GCCGATGAAA ATGACATAAA CTGGGATCTT    840

TTAGCTGAAG GATGGAGCAG TGTCCGTTCA CCACAGTGGC TTCGAAGTAA ATGGTGGACC    900

ATCAAAAGGC AAATTGCAAA CCATAAGGAT GTTTCATTTC CTGTCCTAAT AAAAGGTCTT    960

AAACAGTTAC ATGAGAACCA AAAAAACAAC CCAGTGCTTT TGGAGAATAA ATCAGGATCT   1020

GGAGTTCCAA ACAGTAATTG CAATTCCAGT GTACAGCATG TTCAGATCAG AGTCGCCCGC   1080

TTGGAAGATA ATACAGCCAT CTCTCCAAGC CCCATG                             1116
```

(2) INFORMATION FOR SEQ ID NO: 18:

(i) SEQUENCE CHARACTERISTICS:
(A) LENGTH: 303 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: C-terminal (vi) ORIGINAL SOURCE:
(A) ORGANISM: Mus musculus (xi) SEQUENCE DESCRIPTION: SEQ ID NO: 18:

```
Ala Ala Leu Gln Ile Pro Val Gln Ile Thr His Val Ser Ser Thr Asp
1               5                   10                  15

Ser Pro Ala Ala Ser Ala Asp Ser Glu Thr Ile Thr Leu Asn Ser Gly
            20                  25                  30

Thr Leu Gln Thr Phe Glu Ile Leu Pro Ser Phe Pro Leu Gln Pro Thr
        35                  40                  45

Gly Thr Pro Gly Thr Tyr Leu Leu Gln Thr Ser Ser Ser Gln Gly Leu
    50                  55                  60

Pro Leu Thr Leu Thr Thr Asn Pro Thr Leu Thr Leu Ala Ala Ala Ala
65                  70                  75                  80

Pro Ala Ser Pro Glu Gln Ile Ile Val His Ala Leu Ser Pro Glu His
                85                  90                  95

Leu Leu Asn Thr Ser Asp Asn Val Thr Val Gln Cys His Thr Pro Arg
            100                 105                 110

Val Ile Ile Gln Thr Val Ala Thr Glu Asp Ile Thr Ser Ser Leu Ser
        115                 120                 125

Gln Glu Glu Leu Thr Val Asp Ser Asp Leu His Ser Ser Asp Phe Pro
    130                 135                 140

Glu Pro Pro Asp Ala Leu Glu Ala Asp Thr Phe Pro Asp Glu Ile Pro
145                 150                 155                 160

Arg Pro Lys Met Thr Ile Gln Pro Ser Phe Asn Asn Ala His Val Ser
                165                 170                 175

Lys Phe Ser Asp Gln Asn Ser Thr Glu Leu Met Asn Ser Val Met Val
```

-continued

```
            180                 185                 190

Arg Thr Glu Glu Glu Ile Ala Asp Thr Asp Leu Lys Gln Glu Glu Pro
        195                 200                 205

Pro Ser Asp Leu Ala Ser Ala Tyr Val Thr Glu Asp Leu Glu Ser Pro
    210                 215                 220

Thr Ile Val His Gln Val His Gln Thr Ile Asp Asp Glu Thr Ile Leu
225                 230                 235                 240

Ile Val Pro Ser Pro His Gly Phe Ile Gln Ala Ser Asp Val Ile Asp
                245                 250                 255

Thr Glu Ser Val Leu Pro Leu Thr Thr Leu Thr Asp Pro Ile Phe Gln
            260                 265                 270

His His Gln Glu Ala Ser Asn Ile Ile Gly Ser Ser Leu Gly Ser Pro
        275                 280                 285

Val Ser Glu Asp Ser Lys Asp Val Glu Asp Leu Val Asn Cys His
    290                 295                 300
```

(2) INFORMATION FOR SEQ ID NO: 19:

(i) SEQUENCE CHARACTERISTICS:
(A) LENGTH: 909 base pairs
(B) TYPE: nucleic acid
(C) STRANDEDNESS: double
(D) TOPOLOGY: linear (ii) MOLECULE TYPE: cDNA (iii) HYPOTHETICAL: NO (vi) ORIGINAL SOURCE:
(A) ORGANISM: Mus musculus (xi) SEQUENCE DESCRIPTION: SEQ ID NO: 19:

```
GCAGCGTTGC AGATTCCAGT CCAGATCACC CACGTCTCTT CAACAGACTC CCCTGCTGCT     60

TCTGCCGACT CAGAAACAAT CACACTAAAC AGTGGAACAC TACAAACATT TGAGATTCTT    120

CCATCTTTTC CATTACAGCC CACTGGTACT CCAGGCACCT ACCTTCTTCA AACAAGCTCA    180

AGTCAAGGCC TTCCCCTAAC ACTGACCACA AATCCCACAC TAACCCTGGC AGCTGCTGCT    240

CCTGCTTCTC CTGAACAGAT CATTGTTCAT GCTTTATCCC CAGAACATTT GTTGAACACA    300

AGCGATAATG TCACGGTACA ATGTCACACA CCAAGAGTCA TCATTCAGAC GGTAGCTACA    360

GAGGACATCA CTTCTTCATT ATCCCAAGAG GAACTGACAG TTGATAGTGA TCTTCATTCA    420

TCTGATTTCC CTGAGCCTCC AGATGCACTA GAAGCAGACA CTTTCCCAGA CGAAATTCCT    480

CGGCCTAAGA TGACTATACA ACCATCATTT AATAATGCTC ATGTATCTAA ATTCAGCGAC    540

CAAAATAGCA CAGAACTGAT GAACAGTGTC ATGGTCAGAA CAGAGGAAGA AATTGCCGAC    600

ACTGACCTTA AGCAGGAAGA ACCGCCGTCT GACTTAGCCA GTGCTTATGT TACTGAGGAT    660

TTAGAGTCTC CCACCATAGT GCACCAAGTT CATCAGACAA TTGATGATGA AACAATACTT    720

ATCGTTCCTT CACCTCATGG CTTTATCCAG GCATCTGATG TTATAGATAC TGAATCTGTC    780

TTGCCTTTGA CAACACTAAC AGATCCAATA TTCCAGCATC ATCAGGAAGC ATCAAATATA    840

ATTGGATCAT CTTTGGGCAG TCCTGTTTCT GAAGACTCAA AGGATGTTGA GGACTTAGTA    900

AACTGTCAC                                                            909
```

(2) INFORMATION FOR SEQ ID NO: 20:

(i) SEQUENCE CHARACTERISTICS:
(A) LENGTH: 86 amino acids
(B) TYPE: amino acid

-continued (C) STRANDEDNESS: single
(D) TOPOLOGY: linear (ii) MOLECULE TYPE: peptide (iii) HYPOTHETICAL: NO (v) FRAGMENT TYPE: N-terminal (vi) ORIGINAL SOURCE:
(A) ORGANISM: Mus musculus (xi) SEQUENCE DESCRIPTION: SEQ ID NO: 20:

```
Met Ser Thr Val Glu Glu Asp Ser Asp Thr Val Thr Val Glu Thr Val
1               5                   10                  15

Asn Ser Val Thr Phe Thr Gln Asp Thr Asp Gly Asn Leu Ile Leu His
            20                  25                  30

Cys Pro Gln Asn Asp Pro Asp Glu Val Asp Ser Glu Asp Ser Thr Glu
        35                  40                  45

Pro Pro His Lys Arg Leu Cys Leu Ser Ser Glu Asp Asp Gln Ser Ile
    50                  55                  60

Asp Asp Ala Thr Pro Cys Ile Ser Val Val Ala Leu Pro Leu Ser Glu
65                  70                  75                  80

Asn Asp Gln Ser Phe Glu
                85
```

(2) INFORMATION FOR SEQ ID NO: 21:

(i) SEQUENCE CHARACTERISTICS:
(A) LENGTH: 258 base pairs
(B) TYPE: nucleic acid
(C) STRANDEDNESS: double
(D) TOPOLOGY: linear (ii) MOLECULE TYPE: cDNA (iii) HYPOTHETICAL: NO (vi) ORIGINAL SOURCE:
(A) ORGANISM: Mus musculus (xi) SEQUENCE DESCRIPTION: SEQ ID NO: 21:

```
ATGAGCACAG TTGAAGAGGA TTCTGACACA GTAACAGTAG AAACTGTGAA CTCTGTGACG     60

TTTACTCAGG ACACGGACGG GAATCTCATT CTTCATTGCC CTCAGAATGA CCCTGATGAA    120

GTAGACTCAG AAGACAGTAC TGAACCTCCA CATAAGAGGC TTTGTTTGTC CTCTGAGGAT    180

GATCAAAGCA TTGATGACGC TACGCCATGC ATATCAGTCG TGGCACTCCC ACTTTCAGAA    240

AATGATCAGA GCTTTGAG                                                  258
```

(2) INFORMATION FOR SEQ ID NO: 22:

(i) SEQUENCE CHARACTERISTICS:
(A) LENGTH: 223 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: N-terminal (vi) ORIGINAL SOURCE:
(A) ORGANISM: Mus musculus (xi) SEQUENCE DESCRIPTION: SEQ ID NO: 22:

-continued

```
Met Ser Thr Val Glu Glu Asp Ser Asp Thr Val Thr Val Glu Thr Val
1               5                   10                  15

Asn Ser Val Thr Phe Thr Gln Asp Thr Asp Gly Asn Leu Ile Leu His
            20                  25                  30

Cys Pro Gln Asn Asp Pro Asp Glu Val Asp Ser Glu Asp Ser Thr Glu
        35                  40                  45

Pro Pro His Lys Arg Leu Cys Leu Ser Ser Glu Asp Asp Gln Ser Ile
    50                  55                  60

Asp Asp Ala Thr Pro Cys Ile Ser Val Val Ala Leu Pro Leu Ser Glu
65                  70                  75                  80

Asn Asp Gln Ser Phe Glu Val Thr Met Thr Ala Thr Thr Glu Val Ala
                85                  90                  95

Asp Asp Glu Leu Ser Glu Gly Thr Val Thr Gln Ile Gln Ile Leu Gln
            100                 105                 110

Asn Asp Gln Leu Asp Glu Ile Ser Pro Leu Gly Thr Glu Glu Val Ser
        115                 120                 125

Ala Val Ser Gln Ala Trp Phe Thr Thr Lys Glu Asp Lys Asp Ser Leu
    130                 135                 140

Thr Asn Lys Gly His Lys Trp Lys Gln Gly Met Trp Ser Lys Glu Glu
145                 150                 155                 160

Ile Asp Ile Leu Met Asn Asn Ile Glu Arg Tyr Leu Lys Ala Arg Gly
                165                 170                 175

Ile Lys Asp Ala Thr Glu Ile Ile Phe Glu Met Ser Lys Asp Glu Arg
            180                 185                 190

Lys Asp Phe Tyr Arg Thr Ile Ala Trp Gly Leu Asn Arg Pro Leu Phe
        195                 200                 205

Ala Val Tyr Arg Arg Val Leu Arg Met Tyr Asp Asp Arg Asn His
    210                 215                 220
```

(2) INFORMATION FOR SEQ ID NO: 23:

(i) SEQUENCE CHARACTERISTICS:
(A) LENGTH: 669 base pairs
(B) TYPE: nucleic acid
(C) STRANDEDNESS: double
(D) TOPOLOGY: linear (ii) MOLECULE TYPE: cDNA (iii) HYPOTHETICAL: NO (vi) ORIGINAL SOURCE:
(A) ORGANISM: Mus musculus (xi) SEQUENCE DESCRIPTION: SEQ ID NO: 23:

```
ATGAGCACAG TTGAAGAGGA TTCTGACACA GTAACAGTAG AAACTGTGAA CTCTGTGACG     60

TTTACTCAGG ACACGGACGG GAATCTCATT CTTCATTGCC CTCAGAATGA CCCTGATGAA    120

GTAGACTCAG AAGACAGTAC TGAACCTCCA CATAAGAGGC TTTGTTTGTC CTCTGAGGAT    180

GATCAAAGCA TTGATGACGC TACGCCATGC ATATCAGTCG TGGCACTCCC ACTTTCAGAA    240

AATGATCAGA GCTTTGAGGT GACCATGACG GCAACTACAG AGGTGGCAGA TGATGAACTT    300

TCTGAGGGAA CTGTGACACA AATTCAGATT TTACAGAATG ATCAACTAGA TGAAATATCT    360

CCATTGGGTA CTGAGGAAGT CTCAGCAGTT AGCCAAGCGT GGTTTACAAC TAAAGAAGAT    420

AAGGATTCTC TCACTAACAA AGGACATAAA TGGAAGCAGG GGATGTGGTC CAAGGAAGAA    480

ATTGATATTT TAATGAACAA CATCGAGCGC TATCTGAAGG CTCGCGGAAT AAAAGATGCT    540
```

-continued

```
ACAGAAATCA TCTTTGAGAT GTCAAAAGAC GAAAGAAAAG ATTTCTACAG GACTATAGCG    600

TGGGGGCTGA ACCGGCCTTT GTTTGCAGTT TATAGAAGAG TGCTGCGCAT GTATGATGAC    660

AGGAACCAT                                                            669
```

(2) INFORMATION FOR SEQ ID NO: 24:

(i) SEQUENCE CHARACTERISTICS:
(A) LENGTH: 262 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: C-terminal (vi) ORIGINAL SOURCE:
(A) ORGANISM: Homo sapiens (xi) SEQUENCE DESCRIPTION: SEQ ID NO: 24:

```
Ser Phe His Leu Gln Pro Thr Gly Thr Pro Gly Thr Tyr Leu Leu Gln
1               5                   10                  15

Thr Ser Ser Ser Gln Gly Leu Pro Leu Thr Leu Thr Ala Ser Pro Thr
            20                  25                  30

Val Thr Leu Thr Ala Ala Ala Pro Ala Ser Pro Glu Gln Ile Ile Val
        35                  40                  45

His Ala Leu Ser Pro Glu His Leu Leu Asn Thr Ser Asp Asn Val Thr
    50                  55                  60

Val Gln Cys His Thr Pro Arg Val Ile Ile Gln Thr Val Ala Thr Glu
65                  70                  75                  80

Asp Ile Thr Ser Ser Ile Ser Gln Ala Glu Leu Thr Val Asp Ser Asp
                85                  90                  95

Ile Gln Ser Ser Asp Phe Pro Glu Pro Pro Asp Ala Leu Glu Ala Asp
            100                 105                 110

Thr Phe Pro Asp Glu Ile His His Pro Lys Met Thr Val Glu Pro Ser
        115                 120                 125

Phe Asn Asp Ala His Val Ser Lys Phe Ser Asp Gln Asn Ser Thr Glu
    130                 135                 140

Leu Met Asn Ser Val Met Val Arg Thr Glu Glu Glu Ile Ser Asp Thr
145                 150                 155                 160

Asp Leu Lys Gln Glu Glu Ser Pro Ser Asp Leu Ala Ser Ala Tyr Val
                165                 170                 175

Thr Glu Gly Leu Glu Ser Pro Thr Ile Glu Glu Gln Val Asp Gln Thr
            180                 185                 190

Ile Asp Asp Glu Thr Ile Leu Ile Val Pro Ser Pro His Gly Phe Ile
        195                 200                 205

Gln Ala Ser Asp Val Ile Asp Thr Glu Ser Val Leu Pro Leu Thr Thr
    210                 215                 220

Leu Thr Asp Pro Ile Leu Gln His His Gln Glu Glu Ser Asn Ile Ile
225                 230                 235                 240

Gly Ser Ser Leu Gly Ser Pro Val Ser Glu Asp Ser Lys Asp Val Glu
                245                 250                 255

Asp Leu Val Asn Cys His
            260
```

(2) INFORMATION FOR SEQ ID NO: 25:

-continued (i) SEQUENCE CHARACTERISTICS:
(A) LENGTH: 800 base pairs
(B) TYPE: nucleic acid
(C) STRANDEDNESS: double
(D) TOPOLOGY: linear (ii) MOLECULE TYPE: cDNA (iii) HYPOTHETICAL: NO (vi) ORIGINAL SOURCE:
(A) ORGANISM: Homo sapiens (xi) SEQUENCE DESCRIPTION: SEQ ID NO: 25:

```
CCTCTTTCCA TCTACAGCCC ACTGGCACTC CAGGCACCTA CCTACTTCAA ACAAGCTCAA     60
GCCAAGGCCT TCCCCTAACT CTGACTGCTA GTCCCACAGT AACCCTGACA GCTGCTGCTC    120
CTGCTTCTCC TGAACAGATT ATTGTTCATG CTTTATCCCC AGAACATTTG TTGAACACAA    180
GTGATAATGT TACAGTGCAG TGTCACACAC CAAGAGTCAT CATTCAGACT GTTGCCACAG    240
AGGACATCAC TTCTTCCATA TCCCAAGCAG AACTGACCGT CGATAGTGAT ATTCAGTCAT    300
CTGATTTTCC TGAGCCTCCA GACGCCCTAG AAGCAGACAC TTTCCCAGAT GAAATTCATC    360
ACCCTAAGAT GACTGTGGAG CCATCATTTA ATGATGCTCA TGTATCCAAA TTCAGTGACC    420
AAAATAGCAC AGAACTGATG AATAGTGTTA TGGTCAGAAC AGAAGAAGAA ATCTCTGACA    480
CCGACCTTAA ACAAGAGGAA TCACCCTCTG ATTTAGCCAG TGCTTATGTT ACTGAGGGTT    540
TAGAGTCTCC CACTATAGAA GAACAAGTTG ATCAAACAAT TGATGATGAA ACAATACTTA    600
TCGTTCCTTC ACCACATGGC TTTATCCAGG CATCTGATGT TATAGATACT GAATCTGTCT    660
TGCCTTTGAC AACACTAACA GATCCCATAC TCCAACATCA TCAGGAAGAA TCAAATATCA    720
TTGGATCATC CTTGGGCAGT CCTGTTTCAG AAGATTCAAA GGATGTCGAA GATTTGGTAA    780
ACTGTCATTA GAATAATTCT                                                800
```

(2) INFORMATION FOR SEQ ID NO: 26:

(i) SEQUENCE CHARACTERISTICS:
(A) LENGTH: 800 base pairs
(B) TYPE: nucleic acid
(C) STRANDEDNESS: single
(D) TOPOLOGY: linear (ii) MOLECULE TYPE: RNA (genomic)

(iii) HYPOTHETICAL: NO (vi) ORIGINAL SOURCE:
(A) ORGANISM: Homo sapiens (xi) SEQUENCE DESCRIPTION: SEQ ID NO: 26:

```
CCUCUUUCCA UCUACAGCCC ACUGGCACUC CAGGCACCUA CCUACUUCAA ACAAGCUCAA     60
GCCAAGGCCU UCCCCUAACU CUGACUGCUA GUCCCACAGU AACCCUGACA GCUGCUGCUC    120
CUGCUUCUCC UGAACAGAUU AUUGUUCAUG CUUUAUCCCC AGAACAUUUG UUGAACACAA    180
GUGAUAAUGU UACAGUGCAG UGUCACACAC CAAGAGUCAU CAUUCAGACU GUUGCCACAG    240
AGGACAUCAC UUCUUCCAUA UCCCAAGCAG AACUGACCGU CGAUAGUGAU AUUCAGUCAU    300
CUGAUUUUCC UGAGCCUCCA GACGCCCUAG AAGCAGACAC UUUCCCAGAU GAAAUUCAUC    360
ACCCUAAGAU GACUGUGGAG CCAUCAUUUA AUGAUGCUCA UGUAUCCAAA UUCAGUGACC    420
AAAAUAGCAC AGAACUGAUG AAUAGUGUUA UGGUCAGAAC AGAAGAAGAA AUCUCUGACA    480
CCGACCUUAA ACAAGAGGAA UCACCCUCUG AUUUAGCCAG UGCUUAUGUU ACUGAGGGUU    540
```

-continued

UAGAGUCUCC CACUAUAGAA GAACAAGUUG AUCAAACAAU UGAUGAUGAA ACAAUACUUA 600

UCGUUCCUUC ACCACAUGGC UUUAUCCAGG CAUCUGAUGU UAUAGAUACU GAAUCUGUCU 660

UGCCUUUGAC AACACUAACA GAUCCCAUAC UCCAACAUCA UCAGGAAGAA UCAAAUAUCA 720

UUGGAUCAUC CUUGGGCAGU CCUGUUUCAG AAGAUUCAAA GGAUGUCGAA GAUUUGGUAA 780

ACUGUCAUUA GAAUAAUUCU 800

(2) INFORMATION FOR SEQ ID NO: 27:

(i) SEQUENCE CHARACTERISTICS:
(A) LENGTH: 850 base pairs
(B) TYPE: nucleic acid
(C) STRANDEDNESS: double
(D) TOPOLOGY: linear (ii) MOLECULE TYPE: cDNA (iii) HYPOTHETICAL: NO (vi) ORIGINAL SOURCE:
(A) ORGANISM: Homo sapiens (xi) SEQUENCE DESCRIPTION: SEQ ID NO: 27:

CCTCTTTCCA TCTACAGCCC ACTGGCACTC CAGGCACCTA CCTACTTCAA ACAAGCTCAA 60

GCCAAGGCCT TCCCCTAACT CTGACTGCTA GTCCCACAGT AACCCTGACA GCTGCTGCTC 120

CTGCTTCTCC TGAACAGATT ATTGTTCATG CTTTATCCCC AGAACATTTG TTGAACACAA 180

GTGATAATGT TACAGTGCAG TGTCACACAC CAAGAGTCAT CATTCAGACT GTTGCCACAG 240

AGGACATCAC TTCTTCCATA TCCCAAGCAG AACTGACCGT CGATAGTGAT ATTCAGTCAT 300

CTGATTTTCC TGAGCCTCCA GACGCCCTAG AAGCAGACAC TTTCCCAGAT GAAATTCATC 360

ACCCTAAGAT GACTGTGGAG CCATCATTTA ATGATGCTCA TGTATCCAAA TTCAGTGACC 420

AAAATAGCAC AGAACTGATG AATAGTGTTA TGGTCAGAAC AGAAGAAGAA ATCTCTGACA 480

CCGACCTTAA ACAAGAGGAA TCACCCTCTG ATTTAGCCAG TGCTTATGTT ACTGAGGGTT 540

TAGAGTCTCC CACTATAGAA GAACAAGTTG ATCAAACAAT TGATGATGAA ACAATACTTA 600

TCGTTCCTTC ACCACATGGC TTTATCCAGG CATCTGATGT TATAGATACT GAATCTGTCT 660

TGCCTTTGAC AACACTAACA GATCCCATAC TCCAACATCA TCAGGAAGAA TCAAATATCA 720

TTGGATCATC CTTGGGCAGT CCTGTTTCAG AAGATTCAAA GGATGTCGAA GATTTGGTAA 780

ACTGTCATTA GAATAATTCT TAGAAATAGG CAGTTCAAGC AAAGAAGGCA CACTGTTAAT 840

TACAACCTCT 850

(2) INFORMATION FOR SEQ ID NO: 28:

(i) SEQUENCE CHARACTERISTICS:
(A) LENGTH: 3767 base pairs
(B) TYPE: nucleic acid
(C) STRANDEDNESS: double
(D) TOPOLOGY: linear (ii) MOLECULE TYPE: cDNA (iii) HYPOTHETICAL: NO (vi) ORIGINAL SOURCE:
(A) ORGANISM: Homo sapiens (xi) SEQUENCE DESCRIPTION: SEQ ID NO: 28:

GCGGCCGCAG CTCCGTTTCC GGTGGCTCGT CGCGCTCGCT CACTCCAGCT GCAGCCACTC 60

-continued

```
TCGCCCGTGG CTGCTTCCTC CATCCTGGTA TTTTTTGGAG CTTCCATCCT GGTTCTTCCA    120
AAGTGCCCGG ACCCAAAACA GGAAAGTGTT GCGGAGATAG GAACATGGGA GAGAAACAAT    180
CTGGGTAACA TGAAAGTGAT GCTGGTTGCT AAGGGAAGGC AACTTGATTC TGTGGGAAGG    240
GCTGTAGCTG ATCCATCCGT TGTCTAGATT TGAGTATGAG CACAGTGGAA GAGGATTCTG    300
ACACAGTAAC AGTAGAAACT GTGAACTCTG TGACTTTGAC TCAGGACACA GAAGGGAATC    360
TCATTCTTCA CTGCCCTCAG AATGAAGCGG ATGAAATAGA CTCAGAAGAT AGTATTGAAC    420
CTCCACATAA AAGGCTTTGT TTGTCCTCTG AGGATGATCA GAGTATTGAT GATTCTACTC    480
CTTGCATATC AGTTGTTGCA CTTCCACTTT CAGAAAATGA TCAGAGCTTT GAAGTGACCA    540
TGACTGCAAC CACAGAAGTA GCAGATGATG AGGTTACTGA GGGGACTGTG ACACAGATAC    600
AGATTTTGCA GAATGAGCAA CTAGATGAAA TATCTCCCTT GGGTAACGAG GAAGTTTCAG    660
CAGTTAGCCA AGCATGGTTT ACAACTAAAG AAGATAAGGA TTCTCTGACT AATAAAGGAC    720
ATAAATGGAA GCAGGGGATG TGGTCCAAGG AAGAAATTGA TATTTTGATG AACAATATTG    780
AACGCTATCT TAAGGCACGC GGAATAAAAG ATGCTACAGA AATCATCTTT GAGATGTCAA    840
AAGACGAAAG AAAAGATTTC TACAGGACTA TAGCATGGGG TCTGAACCGG CCTTTGTTTG    900
CAGTTTATAG AAGAGTGCTT CGCATGTATG ATGACAGAAA CCATGTGGGA AAATATACAC    960
CTGAAGAAAT TGAGAAGCTC AAGGAGCTCC GGATAAAGCA TGGCAATGAC TGGGCAACAA   1020
TAGGGGCGGC GCTAGGAAGA AGTGCATCTT CTGTCAAAGA TCGGTGCCGA CTGATGAAGG   1080
ATACTTGCAA CACAGGGAAG TGGACAGAAG AAGAAGAAAA GAGACTTGCA GAAGTGGTTC   1140
ATGAGTTGAC AAGCACTGAG CCAGGTGACA TAGTCACACA GGGTGTGTCT TGGGCAGCTG   1200
TGGCTGAACG AGTCGGTACC CGCTCAGAAA AGCAATGTCG TTCTAAATGG CTCAACTACC   1260
TGAATTGGAA ACAGAGTGGG GGTACTGAAT GGACCAAGGA AGATGAAATC AATCTCATCC   1320
TCAGGATAGC AGAACTTGAT GTAGCTGATG AAAATGACAT TAACTGGGAT CTGTTAGCTG   1380
AGGGATGGAG TAGTGTCCGT TCACCACAAT GGCTACGAAG TAAATGGTGG ACCATCAAAA   1440
GGCAAATTGC AAACCATAAG GATGTTTCGT TCCCTGTCTT AATAAAAGGT CTTAAACAGT   1500
TACATGAGAA CCAAAAAAAC AACCCAACGC TTTTGGAGAA TAAATCAGGA TCTGGAGTTC   1560
CAAACAGTAA TACCAATTCC AGTGTGCAGC ATGTTCAGAT AAGAGTTGCC CGCTTGGAAG   1620
ATAATACAGC CATCTCTTCT AGCCCCATGG CAGCATTGCA GATTCCAGTC CAGATCACCC   1680
ATGTTTCTTC AGCAGACTCT CCTGCTACCG TTGACTCAGA AACAATAACA CTAAACAGTG   1740
GAACACTACA GACATTTGAG ATTCTTCCCT CTTTCCATCT ACAGCCCACT GGCACTCCAG   1800
GCACCTACCT ACTTCAAACA AGCTCAAGCC AAGGCCTTCC CCTAACTCTG ACTGCTAGTC   1860
CCACAGTAAC CCTGACAGCT GCTGCTCCTG CTTCTCCTGA ACAGATTATT GTTCATGCTT   1920
TATCCCCAGA ACATTTGTTG AACACAAGTG ATAATGTTAC AGTGCAGTGT CACACACCAA   1980
GAGTCATCAT TCAGACTGTT GCCACAGAGG ACATCACTTC TTCCATATCC CAAGCAGAAC   2040
TGACAGTCGA TAGTGATATT CAGTCATCTG ATTTTCCTGA GCCTCCAGAC GCCCTAGAAG   2100
CAGACACTTT CCCAGATGAA ATTCATCACC CTAAGATGAC TGTGGAGCCA TCATTTAATG   2160
ATGCTCATGT ATCCAAATTC AGTGACCAAA ATAGCACAGA ACTGATGAAT AGTGTTATGG   2220
TCAGAACAGA AGAAGAAATC TCTGACACCG ACCTTAAACA AGAGGAATCA CCCTCTGATT   2280
TAGCCAGTGC TTATGTTACT GAGGGTTTAG AGTCTCCCAC TATAGAAGAA CAAGTTGATC   2340
AAACAATTGA TGATGAAACA ATACTTATCG TTCCTTCACC ACATGGCTTT ATCCAGGCAT   2400
CTGATGTTAT AGATACTGAA TCTGTCTTGC CTTTGACAAC ACTAACAGAT CCCATACTCC   2460
```

```
AACATCATCA GGAAGAATCA AATATCATTG GATCATCCTT GGGCAGTCCT GTTTCAGAAG   2520

ATTCAAAGGA TGTCGAAGAT TTGGTAAACT GTCATTAGAA TAATTCTTAG AAATAGGCAG   2580

TTCAAGCAAA GAAGGCACAC TGTTAATTAC AACCTCTTCA AAGAAATAGG AGCAAACCCC   2640

CAAGAGGCTT AATTTACCAA TTTAAATAGC CACAGTCCTT AAGCCACACA CATTGTTGCT   2700

GCTATGACTT TTTACCTCCT TTAAACACAT CATCTGAGGT TGAGTTTTAT GACAGTATGT   2760

AGTTGAGTGG AGGCTGGGAG TTTTAAGCAT AAATCCCTGT TTAGTGTTAC ATGGGAATAA   2820

GGAATTTCAT TCACTTCAGC CACTAAGAAA AGTTTAGAAT CACGAAAGCT TAACTGCTGT   2880

GGTTTAAAGT ACAGTTTCTC TAAAGATCAG ACATGGCACT GTCTCCTCTC AAGCCTGGTT   2940

GTAGTTCAGA TGAGTCTTTT CAACATGGTC TTCAACATGG TCTAGAGCTT ACCAGTGATC   3000

TTCTGATCTT CAAGAAGACT AAGTTTGAGA CTTGACCAGC ATACAAGTAT AGAGACCTAG   3060

GAGGTGGTCT TGTGGTGGTA CATTTGGTTA ACCCATTGCT GGCAGTGGGA GCTGATTTAG   3120

GCAGGGTAAA CAGGAAAGCA TTAAAAGTTA AAATTCACTA CAGGTTTTTT GTTACTTTTA   3180

AAGGGAATAT GGATAAGCAT AGTAACAAAA CCCACCAGAA TCTAAGCAGT TTTCACCCCC   3240

TCAGAAACCA CTGTCATTAG TTTACAAAGT TAGCACTTTG AAGTAAAACT AAATGAGGAA   3300

GGAAGTAATG TTACCTATCC TTGATACCAT GACCATTTAT TAGATGTTTT GCTATATAAA   3360

TTACCGAGAG AATAGTTTGT CATCCACTTA GTGTGTTAGC TGGTGGGGTA CAATATAACC   3420

TCTCATCTCA GGCTATTTTA AAAAAACAAT ATTTGCTTCT ATAACAAAAG GAAACAAATC   3480

TAAGAATCAT TCCTGTACTA CAGAAGGGTT AAGGCAAAGG TAGCCTTTTG GGCTTTTTAA   3540

TGAATATGAC CCCTATAGAA AAGTCAAGAA AAAAAAACCC TTGTATAAAT TATTTTATTT   3600

ATTATTGTAA TTAGATCTTC ACAAAGTTGT CTTTTCACTG TGTTTTGTCA ACGTGAAATT   3660

AAATTGTAGT TATAAGCAAA AGTTGGTTGC CTAGGGAACA ATTGTATATT CAGTTTAACA   3720

GAAATAAAAG AATATTTGTC TTAAAAAAAA AAAAAAAAAA ACTCGAG                 3767
```

(2) INFORMATION FOR SEQ ID NO: 29:

(i) SEQUENCE CHARACTERISTICS:
(A) LENGTH: 760 amino acids
(B) TYPE: amino acid
(C) STRANDEDNESS: single
(D) TOPOLOGY: linear (ii) MOLECULE TYPE: protein (iii) HYPOTHETICAL: NO (vi) ORIGINAL SOURCE:
(A) ORGANISM: Homo sapiens (xi) SEQUENCE DESCRIPTION: SEQ ID NO: 29:

```
Met Ser Thr Val Glu Glu Asp Ser Asp Thr Val Thr Val Glu Thr Val
1               5                   10                  15

Asn Ser Val Thr Leu Thr Gln Asp Thr Glu Gly Asn Leu Ile Leu His
            20                  25                  30

Cys Pro Gln Asn Glu Ala Asp Glu Ile Asp Ser Glu Asp Ser Ile Glu
        35                  40                  45

Pro Pro His Lys Arg Leu Cys Leu Ser Ser Glu Asp Asp Gln Ser Ile
    50                  55                  60

Asp Asp Ser Thr Pro Cys Ile Ser Val Val Ala Leu Pro Leu Ser Glu
65                  70                  75                  80

Asn Asp Gln Ser Phe Glu Val Thr Met Thr Ala Thr Thr Glu Val Ala
```

-continued

```
                85                  90                  95

Asp Asp Glu Val Thr Glu Gly Thr Val Thr Gln Ile Gln Ile Leu Gln
            100                 105                 110

Asn Glu Gln Leu Asp Glu Ile Ser Pro Leu Gly Asn Glu Glu Val Ser
        115                 120                 125

Ala Val Ser Gln Ala Trp Phe Thr Thr Lys Glu Asp Lys Asp Ser Leu
    130                 135                 140

Thr Asn Lys Gly His Lys Trp Lys Gln Gly Met Trp Ser Lys Glu Glu
145                 150                 155                 160

Ile Asp Ile Leu Met Asn Asn Ile Glu Arg Tyr Leu Lys Ala Arg Gly
                165                 170                 175

Ile Lys Asp Ala Thr Glu Ile Ile Phe Glu Met Ser Lys Asp Glu Arg
            180                 185                 190

Lys Asp Phe Tyr Arg Thr Ile Ala Trp Gly Leu Asn Arg Pro Leu Phe
        195                 200                 205

Ala Val Tyr Arg Arg Val Leu Arg Met Tyr Asp Asp Arg Asn His Val
    210                 215                 220

Gly Lys Tyr Thr Pro Glu Glu Ile Glu Lys Leu Lys Glu Leu Arg Ile
225                 230                 235                 240

Lys His Gly Asn Asp Trp Ala Thr Ile Gly Ala Ala Leu Gly Arg Ser
                245                 250                 255

Ala Ser Ser Val Lys Asp Arg Cys Arg Leu Met Lys Asp Thr Cys Asn
            260                 265                 270

Thr Gly Lys Trp Thr Glu Glu Glu Glu Lys Arg Leu Ala Glu Val Val
        275                 280                 285

His Glu Leu Thr Ser Thr Glu Pro Gly Asp Ile Val Thr Gln Gly Val
    290                 295                 300

Ser Trp Ala Ala Val Ala Glu Arg Val Gly Thr Arg Ser Glu Lys Gln
305                 310                 315                 320

Cys Arg Ser Lys Trp Leu Asn Tyr Leu Asn Trp Lys Gln Ser Gly Gly
                325                 330                 335

Thr Glu Trp Thr Lys Glu Asp Glu Ile Asn Leu Ile Leu Arg Ile Ala
            340                 345                 350

Glu Leu Asp Val Ala Asp Glu Asn Asp Ile Asn Trp Asp Leu Leu Ala
        355                 360                 365

Glu Gly Trp Ser Ser Val Arg Ser Pro Gln Trp Leu Arg Ser Lys Trp
    370                 375                 380

Trp Thr Ile Lys Arg Gln Ile Ala Asn His Lys Asp Val Ser Phe Pro
385                 390                 395                 400

Val Leu Ile Lys Gly Leu Lys Gln Leu His Glu Asn Gln Lys Asn Asn
                405                 410                 415

Pro Thr Leu Leu Glu Asn Lys Ser Gly Ser Gly Val Pro Asn Ser Asn
            420                 425                 430

Thr Asn Ser Ser Val Gln His Val Gln Ile Arg Val Ala Arg Leu Glu
        435                 440                 445

Asp Asn Thr Ala Ile Ser Ser Ser Pro Met Ala Ala Leu Gln Ile Pro
    450                 455                 460

Val Gln Ile Thr His Val Ser Ser Ala Asp Ser Pro Ala Thr Val Asp
465                 470                 475                 480

Ser Glu Thr Ile Thr Leu Asn Ser Gly Thr Leu Gln Thr Phe Glu Ile
                485                 490                 495

Leu Pro Ser Phe His Leu Gln Pro Thr Gly Thr Pro Gly Thr Tyr Leu
            500                 505                 510
```

-continued

```
Leu Gln Thr Ser Ser Ser Gln Gly Leu Pro Leu Thr Leu Thr Ala Ser
        515                 520                 525

Pro Thr Val Thr Leu Thr Ala Ala Ala Pro Ala Ser Pro Glu Gln Ile
    530                 535                 540

Ile Val His Ala Leu Ser Pro Glu His Leu Leu Asn Thr Ser Asp Asn
545                 550                 555                 560

Val Thr Val Gln Cys His Thr Pro Arg Val Ile Ile Gln Thr Val Ala
                565                 570                 575

Thr Glu Asp Ile Thr Ser Ser Ile Ser Gln Ala Glu Leu Thr Val Asp
            580                 585                 590

Ser Asp Ile Gln Ser Ser Asp Phe Pro Glu Pro Pro Asp Ala Leu Glu
        595                 600                 605

Ala Asp Thr Phe Pro Asp Glu Ile His His Pro Lys Met Thr Val Glu
    610                 615                 620

Pro Ser Phe Asn Asp Ala His Val Ser Lys Phe Ser Asp Gln Asn Ser
625                 630                 635                 640

Thr Glu Leu Met Asn Ser Val Met Val Arg Thr Glu Glu Glu Ile Ser
                645                 650                 655

Asp Thr Asp Leu Lys Gln Glu Glu Ser Pro Ser Asp Leu Ala Ser Ala
            660                 665                 670

Tyr Val Thr Glu Gly Leu Glu Ser Pro Thr Ile Glu Glu Gln Val Asp
        675                 680                 685

Gln Thr Ile Asp Asp Glu Thr Ile Leu Ile Val Pro Ser Pro His Gly
    690                 695                 700

Phe Ile Gln Ala Ser Asp Val Ile Asp Thr Glu Ser Val Leu Pro Leu
705                 710                 715                 720

Thr Thr Leu Thr Asp Pro Ile Leu Gln His His Gln Glu Glu Ser Asn
                725                 730                 735

Ile Ile Gly Ser Ser Leu Gly Ser Pro Val Ser Glu Asp Ser Lys Asp
            740                 745                 750

Val Glu Asp Leu Val Asn Cys His
        755                 760
```

(2) INFORMATION FOR SEQ ID NO: 30:

(i) SEQUENCE CHARACTERISTICS:
(A) LENGTH: 3767 base pairs
(B) TYPE: nucleic acid
(C) STRANDEDNESS: single
(D) TOPOLOGY: linear (ii) MOLECULE TYPE: RNA (iii) HYPOTHETICAL: NO (vi) ORIGINAL SOURCE:
(A) ORGANISM: Homo sapiens (xi) SEQUENCE DESCRIPTION: SEQ ID NO: 30:

```
GCGGCCGCAG CUCCGUUUCC GGUGGCUCGU CGCGCUCGCU CACUCCAGCU GCAGCCACUC     60

UCGCCCGUGG CUGCUUCCUC CAUCCUGGUA UUUUUUGGAG CUUCCAUCCU GGUUCUUCCA    120

AAGUGCCCGG ACCCAAAACA GGAAAGUGUU GCGGAGAUAG GAACAUGGGA GAGAAACAAU    180

CUGGGUAACA UGAAAGUGAU GCUGGUUGCU AAGGGAAGGC AACUUGAUUC UGUGGGAAGG    240

GCUGUAGCUG AUCCAUCCGU UGUCUAGAUU UGAGUAUGAG CACAGUGGAA GAGGAUUCUG    300

ACACAGUAAC AGUAGAAACU GUGAACUCUG UGACUUUGAC UCAGGACACA GAAGGGAAUC    360
```

-continued

```
UCAUUCUUCA CUGCCCUCAG AAUGAAGCGG AUGAAAUAGA CUCAGAAGAU AGUAUUGAAC    420
CUCCACAUAA AAGGCUUUGU UUGUCCUCUG AGGAUGAUCA GAGUAUUGAU GAUUCUACUC    480
CUUGCAUAUC AGUUGUUGCA CUUCCACUUU CAGAAAAUGA UCAGAGCUUU GAAGUGACCA    540
UGACUGCAAC CACAGAAGUA GCAGAUGAUG AGGUUACUGA GGGGACUGUG ACACAGAUAC    600
AGAUUUUGCA GAAUGAGCAA CUAGAUGAAA UAUCUCCCUU GGGUAACGAG GAAGUUUCAG    660
CAGUUAGCCA AGCAUGGUUU ACAACUAAAG AAGAUAAGGA UUCUCUGACU AAUAAAGGAC    720
AUAAAUGGAA GCAGGGGAUG UGGUCCAAGG AAGAAAUUGA UAUUUUGAUG AACAAUAUUG    780
AACGCUAUCU UAAGGCACGC GGAAUAAAAG AUGCUACAGA AAUCAUCUUU GAGAUGUCAA    840
AAGACGAAAG AAAAGAUUUC UACAGGACUA UAGCAUGGGG UCUGAACCGG CCUUUGUUUG    900
CAGUUUAUAG AAGAGUGCUU CGCAUGUAUG AUGACAGAAA CCAUGUGGGA AAAUAUACAC    960
CUGAAGAAAU UGAGAAGCUC AAGGAGCUCC GGAUAAAGCA UGGCAAUGAC UGGGCAACAA   1020
UAGGGGCGGC GCUAGGAAGA AGUGCAUCUU CUGUCAAAGA UCGGUGCCGA CUGAUGAAGG   1080
AUACUUGCAA CACAGGGAAG UGGACAGAAG AAGAAGAAAA GAGACUUGCA GAAGUGGUUC   1140
AUGAGUUGAC AAGCACUGAG CCAGGUGACA UAGUCACACA GGGUGUGUCU UGGGCAGCUG   1200
UGGCUGAACG AGUCGGUACC CGCUCAGAAA AGCAAUGUCG UUCUAAAUGG CUCAACUACC   1260
UGAAUUGGAA ACAGAGUGGG GGUACUGAAU GGACCAAGGA AGAUGAAAUC AAUCUCAUCC   1320
UCAGGAUAGC AGAACUUGAU GUAGCUGAUG AAAAUGACAU UAACUGGGAU CUGUUAGCUG   1380
AGGGAUGGAG UAGUGUCCGU UCACCACAAU GGCUACGAAG UAAAUGGUGG ACCAUCAAAA   1440
GGCAAAUUGC AAACCAUAAG GAUGUUUCGU UCCCUGUCUU AAUAAAAGGU CUUAAACAGU   1500
UACAUGAGAA CCAAAAAAAC AACCCAACGC UUUUGGAGAA UAAAUCAGGA UCUGGAGUUC   1560
CAAACAGUAA UACCAAUUCC AGUGUGCAGC AUGUUCAGAU AAGAGUUGCC CGCUUGGAAG   1620
AUAAUACAGC CAUCUCUUCU AGCCCCAUGG CAGCAUUGCA GAUUCCAGUC CAGAUCACCC   1680
AUGUUUCUUC AGCAGACUCU CCUGCUACCG UUGACUCAGA AACAAUAACA CUAAACAGUG   1740
GAACACUACA GACAUUUGAG AUUCUUCCCU CUUUCCAUCU ACAGCCCACU GGCACUCCAG   1800
GCACCUACCU ACUUCAAACA AGCUCAAGCC AAGGCCUUCC CCUAACUCUG ACUGCUAGUC   1860
CCACAGUAAC CCUGACAGCU GCUGCUCCUG CUUCUCCUGA ACAGAUUAUU GUUCAUGCUU   1920
UAUCCCCAGA ACAUUUGUUG AACACAAGUG AUAAUGUUAC AGUGCAGUGU CACACACCAA   1980
GAGUCAUCAU UCAGACUGUU GCCACAGAGG ACAUCACUUC UUCCAUAUCC CAAGCAGAAC   2040
UGACAGUCGA UAGUGAUAUU CAGUCAUCUG AUUUUCCUGA GCCUCCAGAC GCCCUAGAAG   2100
CAGACACUUU CCCAGAUGAA AUUCAUCACC CUAAGAUGAC UGUGGAGCCA UCAUUUAAUG   2160
AUGCUCAUGU AUCCAAAUUC AGUGACCAAA AUAGCACAGA ACUGAUGAAU AGUGUUAUGG   2220
UCAGAACAGA AGAAGAAAUC UCUGACACCG ACCUUAAACA AGAGGAAUCA CCCUCUGAUU   2280
UAGCCAGUGC UUAUGUUACU GAGGGUUUAG AGUCUCCCAC UAUAGAAGAA CAAGUUGAUC   2340
AAACAAUUGA UGAUGAAACA AUACUUAUCG UUCCUUCACC ACAUGGCUUU AUCCAGGCAU   2400
CUGAUGUUAU AGAUACUGAA UCUGUCUUGC CUUUGACAAC ACUAACAGAU CCCAUACUCC   2460
AACAUCAUCA GGAAGAAUCA AAUAUCAUUG GAUCAUCCUU GGGCAGUCCU GUUUCAGAAG   2520
AUUCAAAGGA UGUCGAAGAU UUGGUAAACU GUCAUUAGAA UAAUUCUUAG AAAUAGGCAG   2580
UUCAAGCAAA GAAGGCACAC UGUUAAUUAC AACCUCUUCA AAGAAAUAGG AGCAAACCCC   2640
CAAGAGGCUU AAUUUACCAA UUUAAAUAGC CACAGUCCUU AAGCCACACA CAUUGUUGCU   2700
GCUAUGACUU UUUACCUCCU UUAAACACAU CAUCUGAGGU UGAGUUUUAU GACAGUAUGU   2760
```

-continued

AGUUGAGUGG AGGCUGGGAG UUUUAAGCAU AAAUCCCUGU UUAGUGUUAC AUGGGAAUAA 2820

GGAAUUUCAU UCACUUCAGC CACUAAGAAA AGUUUAGAAU CACGAAAGCU UAACUGCUGU 2880

GGUUUAAAGU ACAGUUUCUC UAAAGAUCAG ACAUGGCACU GUCUCCUCUC AAGCCUGGUU 2940

GUAGUUCAGA UGAGUCUUUU CAACAUGGUC UUCAACAUGG UCUAGAGCUU ACCAGUGAUC 3000

UUCUGAUCUU CAAGAAGACU AAGUUUGAGA CUUGACCAGC AUACAAGUAU AGAGACCUAG 3060

GAGGUGGUCU UGUGGUGGUA CAUUUGGUUA ACCCAUUGCU GGCAGUGGGA GCUGAUUUAG 3120

GCAGGGUAAA CAGGAAAGCA UUAAAAGUUA AAAUUCACUA CAGGUUUUUU GUUACUUUUA 3180

AAGGGAAUAU GGAUAAGCAU AGUAACAAAA CCCACCAGAA UCUAAGCAGU UUUCACCCCC 3240

UCAGAAACCA CUGUCAUUAG UUUACAAAGU UAGCACUUUG AAGUAAAACU AAAUGAGGAA 3300

GGAAGUAAUG UUACCUAUCC UUGAUACCAU GACCAUUUAU UAGAUGUUUU GCUAUAUAAA 3360

UUACCGAGAG AAUAGUUUGU CAUCCACUUA GUGUGUUAGC UGGUGGGGUA CAAUAUAACC 3420

UCUCAUCUCA GGCUAUUUUA AAAAAACAAU AUUUGCUUCU AUAACAAAAG GAAACAAAUC 3480

UAAGAAUCAU UCCUGUACUA CAGAAGGGUU AAGGCAAAGG UAGCCUUUUG GGCUUUUUAA 3540

UGAAUAUGAC CCCUAUAGAA AAGUCAAGAA AAAAAAACCC UUGUAUAAAU UAUUUUAUUU 3600

AUUAUUGUAA UUAGAUCUUC ACAAAGUUGU CUUUUCACUG UGUUUUGUCA ACGUGAAAUU 3660

AAAUUGUAGU UAUAAGCAAA AGUUGGUUGC CUAGGGAACA AUUGUAUAUU CAGUUUAACA 3720

GAAAUAAAAG AAUAUUUGUC UUAAAAAAAA AAAAAAAAAA ACUCGAG 3767

(2) INFORMATION FOR SEQ ID NO: 31:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(iii) HYPOTHETICAL: NO (xi) SEQUENCE DESCRIPTION: SEQ ID NO: 31:

GGAGATAGGA ACATGGGAG 19

(2) INFORMATION FOR SEQ ID NO: 32:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(iii) HYPOTHETICAL: NO (xi) SEQUENCE DESCRIPTION: SEQ ID NO: 32:

GGAGGTAAAA AGTCATAGCA G 21

(2) INFORMATION FOR SEQ ID NO: 33:

(i) SEQUENCE CHARACTERISTICS:
(A) LENGTH: 9 base pairs
(B) TYPE: nucleic acid
(C) STRANDEDNESS: single
(D) TOPOLOGY: linear -continued (ii) MOLECULE TYPE: other nucleic acid
(A) DESCRIPTION: /desc = "primer"

(iii) HYPOTHETICAL: NO (xi) SEQUENCE DESCRIPTION: SEQ ID NO: 33:

CCCGGATGC 9

(2) INFORMATION FOR SEQ ID NO: 34:

(i) SEQUENCE CHARACTERISTICS:
(A) LENGTH: 361 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vi) ORIGINAL SOURCE:
(A) ORGANISM: Mus musculus (xi) SEQUENCE DESCRIPTION: SEQ ID NO: 34:

GCTAGGGGGC GGGCGGTGCG CACGCGTCCC GCGGCGCTGG CTGTCACCGC GATGGGTGGC 60

GAGCGAAGCG AGCGGGATCC GGAGCGTGCC CTGCGCGGGA GGCAGCGGGA CCCCGGATGC 120

GGCAGGGCCC GCGCGCGCCT CCCCCTGGGC GCCTCTGGGA AGCTTTCCCG CGCGACTGGG 180

GACCGCGCGC CTTGGGAGTC GGGGGCGCGC CTGAGGGCGG AGATGGGCGT GGAGCAAAGA 240

TGGGCCGGGG GCGGCGCGTG GGTCTCGAGG TGCCTCAACG CCGAAGGGGC TGGGGGCGGC 300

GCTTCTCACC TCGCTTGTCA CGGTGAGGCC GCCGCTGAGG GAGTACAGCA GCGGGAGCAT 360

G 361

(2) INFORMATION FOR SEQ ID NO: 35:

(i) SEQUENCE CHARACTERISTICS:
(A) LENGTH: 9 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(iii) HYPOTHETICAL: NO (xi) SEQUENCE DESCRIPTION: SEQ ID NO: 35:

GACGGATGT 9

(2) INFORMATION FOR SEQ ID NO: 36:

(i) SEQUENCE CHARACTERISTICS:
(A) LENGTH: 5703 base pairs
(B) TYPE: nucleic acid
(C) STRANDEDNESS: double
(D) TOPOLOGY: linear (ii) MOLECULE TYPE: cDNA (iii) HYPOTHETICAL: NO (vi) ORIGINAL SOURCE:
(A) ORGANISM: Homo sapiens (xi) SEQUENCE DESCRIPTION: SEQ ID NO: 36:

AAACAGTCCA GAAAGCAAAA AGTAGTAAGC AAAAATCTGA AATTTTTCCC ACCCTCATTC 60

-continued

```
TTACTACCCA AAGGTAACCA CTATTACAAA TATTTAATTA TCCTTCCAGA AATATAAGTA    120
CATATAATTG CAAACATCTC TCCCCCAGCA TGCATATTTG GAAAACATGA ATGGGATCAT    180
ACTATTCTGT CACTTGCTTT CTTTAATTAG CAATAGATCT TTGACAACTT CCATTGTCAG    240
TGCATATAGA TGTGCTTCAT TATTGTTTAT GGATGCACAG TTTTATTATT TTATGAATGA    300
GCCCTAACAA CAACAACAAC AAAAAAAGTC TCCTCACAAG CATGTCAATC ATTTTTCTCT    360
TTCTTGCACT TTGTTTGCTA ATACACACTG CTATAAAGAA ACATTTCTGC ATACTTATAC    420
AAGTTATCTG TAGCAATTTA TATAGGAGTG AATTGCTTTA GCTGAAGTTA CATATCTAAA    480
TGTGTCTGTA GGTGTAAAAT CTATCCATAT ATACATATGT ATCCATACAT AAAATACATA    540
TATACATATG TATGTATATA TATGTGTACA TGTGTATACA TCTTCCCATA CTTACAGATA    600
TGTGTGTACA TATGTGTATA TAAAGATATG TATTATATAT GTTACATACA TGAGTTATAG    660
GAATAGAATT GCTGAGTCAA AGGGTGTATA TAAGTATATA GATATATACA CAAACATATA    720
ACATACATAT GAACTATATA TACTATATAG TATATATGTG TATATATATT TCCATACATT    780
ATTTGTGTGT GTCTTTACAT ACTTAAAATA GTGGAATAGC TGAGTCAAAG GGTACCTATA    840
TTCTCATACA GTTTTGACTA GATATTGTAA TGCTGCCTTT CAAAACAATT ACACCAAGTT    900
GTAATAGTAA GAGTGATTGT TTCCTGACAA CTTTGTCAAA GTAGTCTTTT TTCTTTTTGC    960
CACACTTGTG GTTATATGCC ATTGTTTCTG TTTACATTTA TTAATGAGTA AGATTATCTT   1020
TTTATTTTTT ACTATTTGCA CATATTCTAC TATAAACTAT TATATCCTTT GCCTTTTTTA   1080
TTGGATTGTT GTTTTACTGG ATTATGTATT TATTTATATA GTCTAGTAAT TAATCTTTTG   1140
ACATATATGA TCAAATAATT GTTTTTTATT CTTGCTTATG TTATCTTTTT TCTTATGACT   1200
TTGGGGTTTT GAGTTTGAGC ATGTGCAATG TTAGGAAAGT TTCTCATGAA ATTTGGATAA   1260
TCAAGAGTTA CCTAAGGGAT AAAGCTAGTG TCATAGGACA TTAAGTTTGG GGAGGAGGAG   1320
AACAAGACAA GGGATATTCA GTAAGATTTT TCTCCCCTAT CCCTGCCTAT GGAATGAATT   1380
TGCTGATCTA AAATAGAAAA TTATTTACCC CTGTTAAAAA AAACTCAATT AACTCAGGTT   1440
TTTAGGCCAG TGGAAGAGAA CCCCAAAAAC TTCCAATATT CAGTGATTCT GTCTGCATAA   1500
GTGACCCACA GATAACTCAC TCCCTATTGA CCCTGGCCTT TGGGACAACA GAAAAGGCAC   1560
AAGGCTTGTA ACCCAAAGGC CTGCCTGATG ATTCCAGCCC TGGCTCTTGC TGGCCATGAA   1620
GTGTTCAAGA TTTGAGCCTT TCTAGGCCTC ATTCTTTCCA CCTGTAAAAC AGGAGTAATA   1680
ATCCCAATTT TGAAAGGCCA CTGTGAGGAT AAAATAAGTA ATATAAGTGA AATTACATGC   1740
TCAGTTCTTC ATTATTAATT TTTTGAAGAG CACATAGCCA ATAGTCACTC CGCATTCCAA   1800
AAGTATTTGG AATACCACAT ACCCATTGTT ATGCTAGAAA GAGTCATCTT CACCATTGTA   1860
TTTTGCTGAG ACTAATATTA AACTTAGAAT TCCCCTGCAT ACTGCAACTG AAAGAGAACA   1920
GGTATTGGGC AGCGGCAGTG GGGGAAACCA AGATGGAATT TAGATGTTCA AACTTTAATA   1980
TTTACATTTT TTGAACAGAG AGCTTACTAT ATAATTATTC TTTTATTCAG ATGGCATTCC   2040
TCTGAAATAA GCAATTACCC TTATCCCTAG GTCTAGTTCC TGTGGAGAGA AAATGATTAT   2100
ACTTTGAGCT ATATGGCTCC AATAAACAAA GATAGATCCC TCAATTTAAA TTTGATCCTC   2160
AGAAAACTGA GGGTCAGAGA ATCCCTCAGG CATGACGGGA TAATGTGACA GTTAATTTGG   2220
TATGTCAACT TGGCTAGGCT GTGGTACCCA GTGTTTGAGT CAAACACCAG TCTAAATATT   2280
GCTGTGGAGG TATTTTTTAG ATATGATTAA CATTTAAGTC AGTAGACTTG AAAAAGCAGA   2340
TTATCCTCAA TAATATGGGT GGTCCTCATC CAAGCAGTTG AAGAGCTTAA GAGAAATGAC   2400
```

-continued

```
TGAGGTCCCT CAAGGAAGAA GAAATTCTGC TTCCAGATTG CCTTTGGATT CAAGTCTTGC   2460
AACAACAACT CTTGCCCTGG GTCTCCAATT TGTCAACCCC CACCATTTTC TGAGACAATT   2520
CCTTAAAATA AGTATTTTCT CTCTTTCTCT TTCTCTCTCT CTCTCTCTCT CTCTCCCTCC   2580
CTCTCTTTCT CTCCCCCACA TATGTGTGTG TAGACATATA ATGTACGTAT ATATAAAATT   2640
GTATACACAC ACAGAGTCAT GTGCTGGATA ACGATGCTTC AGTCAACCAC AGTCACATAT   2700
TGGTGGTGTC CCATAAGATT ATAATGGATG TGAAAAATTC CTATCCCCTA GTGATGTCAT   2760
AGCTGTCCTA AAGTTGTAGC ACAACATACT ACCTTTTCTA TGTTTAGATG TGTTTAGATA   2820
TAAAACTACA TTTTGTTACA ATTATCTACA GTATTCAGTA TAGTAACATG TTGTAAAGGT   2880
TTGCAGCCTA GGAGCAATAG CCCATACCAT ACAGCCTAGA TGTATAATAG ACTATACCAC   2940
CTAGGTTTGT ATATGATGTT TGCACAACAA TGAAATCGCC TAAAGATACA TGTCTGAGAA   3000
TGTATCCCTG TTGTTAAGCA ACCCCATGAC GGTGTGTATA TACATATACA TATGTGTGGT   3060
ACTGGCACGC ACACACACAC AATGGGTTCT GTTTGCCCTG GAGAACTGAC TGATATAGAT   3120
AGCGACTTCA AAAGATGTTT AATACGTGCC TTTTCTCCTT TCCCCACCAT GCTTTATTGC   3180
AACAACTAGT TACATTGTCT AGGCCCAAGA AACCCTCACC GCTCCCACTC CATTCCTCCA   3240
GTATCTTTAA ATGACACTAT GCTGGCATCC GACATCGTTT TTCTTCCAGG ATGAACTAAC   3300
CCTTTCTAAA GCGCCCTTCC TCTGTGGGAC AGAAAACCTA ATGCCCCCCT ACAGAGGCGG   3360
AGGCCGGCTG AAGGTGGTGG TAGGAGGGGA ATGCTGGGGG CGTGGCATAG GTGCAGAGGA   3420
AGACCCATAA AAGGATCTGG TTCCCATAGA GCTGACATTC TACACAACAA ACAAGTAAAC   3480
AAGTACATAA GTAAAATAAT CTCTTCGTCC TAAGTGCTAT AAAGAAAAAA ATCACGGTGG   3540
TATGAGGGTG CCTGAAAAGG GAAGCATTTC TGAGGAAGGG CTACTTACTT CAGAAGAGAC   3600
CTGAAGGAAA AAGAGCTATA TTTGCGAAGA GGGAGAAAGA GCAGCCATAC TAGACAGAAA   3660
GGTGGCATGT GGCCCCAGCA CAAAGCACGG TGTTGGGTAA ATTCTGAGTG AAATCTACCT   3720
ACCGGGGAGG TGCATTTGTA AATATCTAGA TAGATATTTA GAGTGGCTAC GTAAGAGTGA   3780
TCGCTAAATC TCATTTTTCC AAAGGGCCCC GTTTTGTCTT GGGTTTGTAC CGAGGTCCGG   3840
CAGCAACGTC AAGTGATGGG GCGGGGGATG GGGAAAGAGA AGTCTGCCGC TCCTCTAGGC   3900
TACCGCACCG CCTTAAGTGG GTGGCTCGGC CAGTGCAGGC CTCACTTTCC TCCCCTGTAA   3960
GGTCTGGGGG GCTTGACGTC TGATCTGTAA GGCCCTGTCG GCTCACGCTG TGGTTCCACT   4020
TCTTCAACTA GGCCACTAGG CCCAAGCGCA TGAACAGGAA GCCACTGAGA AGCGGGCCAC   4080
ATTTCCAGGT TCCCGGAGCT GGGCCTAGTC CCGAATCCTC TGGCACACAC CCACCCACTC   4140
AGGCCGCGGG TCCAGCCCGC GAGGTTTAGG ACGGATCCAG GCAGACCGCA GGCTCCGGGT   4200
CGGGGCACCG GGTCAGCGCG CCGGCCTGAA GGCGGCGTCC TGGGCTCGAC TTCCCGCGCG   4260
CGGAGAGCCG GCGAGCCCGC GTCCGAGTTC CTGGACGAGA GCCGAGCCTC GCTTAGACCG   4320
CGCTCAGGAC CCGGCTCCTC CGCATTCTCC GGCTGCCCCT GTGTCCTCGA CTCACCCCTC   4380
CTTTCTGCCG CTCCTTCCTT TCCTTGCCCT GCTTTTACTG TTCCCAAACA GGACCGCTTT   4440
TCCTGTCTCC CAGCTGGAAA GGAAGAAGGG AGAGAGTCCA GAAAGGATCG GTGATGTGGA   4500
AGAAAAGGGG AGGAGGGGAC ATGGAGGGGG AGACCGGAGA GAGAACGTAC GCCGAGGAGT   4560
CAGGCGGCGG GATCAAGGGG AGTCGGGGTG TCTGGGCGCG GGGCAGAGCG TGGAGGCGGC   4620
AGCGGCCAAC GGTCGCCAAG ACAACCATTC TACGCGAGGA CGCGGCGACA GGAGGGGAGC   4680
GGCCAGCAGG GGAGGGGAGC GCGGGGGAAG AGGAAAGAGG AAGAAGCGCT CAGATGCTCC   4740
GCGGCTGTCG TGAAGGTTAA AACCGAAAAT AAAAATGGGC TAGACACAAA GGACTCGGTG   4800
```

-continued

CTTGTCCCAG CCAGGCGCCC TCGGCGACGC GGGCAGCTGG GAGGGGAATG GGCGCCCGGA 4860

CCCAGCTGGG ACCCCCGGGT GCGACTCCAC CTACCTAGTC CGGCGCCAGG CCGGGTCGAC 4920

AGCTCCGGCA GCGCCAGCGC CGCGCCGTGT CCAGATGTCG CGTCAGAGGC GTGCAGCGGT 4980

TTAGTTTAAT TTCGCTTGTT TTCCAAATCT AGAAGAGGAG CGGAGCGGCT TTTAGTTCAA 5040

AACTGACATT CAGCCTCCTG ATTGGCGGAT AGAGCAATGA GATGACCTCG CTTTCCTTTC 5100

TTCCTTTTTC ATTTTTAAAT AATCTAGTTT GAAGAATGGA AGACTTTCGA CGAGGGGAGC 5160

CAGGAATAAA ATAAGGGGAA TAGGGGAGCG GGGACGCGAG CAGCACCAGA ATCCGCGGGA 5220

GCGCGGCTGT TCCTGGTAGG GCCGTGTCAG GTGACGGATG TAGCTAGGGG GCGAGCTGCC 5280

TGGAGTTGCG TTCCAGGCGT CCGGCCCCTG GGCCGTCACC GCGGGGCGCC CGCGCTGAGG 5340

GTGGGAAGAT GGTGGTGGGG GTGGGGGCGC ACACAGGGCG GGAAAGTGGC GGTAGGCGGG 5400

AGGGAGAGGA ACGCGGGCCC TGAGCCGCCC GCGCGCGCGC CTCCCTACGG GCGCCTCCTA 5460

CAGCCCTTCC CGCGTGCGCA GGGCTCAGAG CCGTTCCGAG ATCTTGGAGG TCCGGGTGGG 5520

AGTGGGGGTG GGGTGGGGGT GGGGGTGAAG GTGGGGGGCG GGCGCGCTCA GGGAAGGCGG 5580

GTGCGCGCCT GCGGGGCGGA GATGGGCAGG GGGCGGTGCG TGGGTCCCAG TCTGCAGTTA 5640

AGGGGGCAGG AGTGGCGCTG CTCACCTCTG GTGCCAAAGG GCGGCGCAGC GGCTGCCGAG 5700

CTC 5703

(2) INFORMATION FOR SEQ ID NO: 37:

(i) SEQUENCE CHARACTERISTICS:
(A) LENGTH: 56 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 37:

CGGATCCGGA GCGTGCCCTG CGCGGGAGGC AGCGGGACCC CGTCGACGGC AGGGCC 56

(2) INFORMATION FOR SEQ ID NO: 38:

(i) SEQUENCE CHARACTERISTICS:
(A) LENGTH: 56 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 38:

CTGCCGTCGA CGGGGTCCCG CTGCCTCCCG CGCAGGGCAC GCTCCGGATC CGGTAC 56

(2) INFORMATION FOR SEQ ID NO: 39:

(i) SEQUENCE CHARACTERISTICS:
(A) LENGTH: 20 base pairs
(B) TYPE: nucleic acid
(C) STRANDEDNESS: double
(D) TOPOLOGY: linear -continued (ii) MOLECULE TYPE: cDNA (iii) HYPOTHETICAL: NO (iv) ANTI-SENSE: NO (xi) SEQUENCE DESCRIPTION: SEQ ID NO: 39:

CACTGACCTT AAGCAGGAAG 20

(2) INFORMATION FOR SEQ ID NO: 40:

(i) SEQUENCE CHARACTERISTICS:
(A) LENGTH: 37 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 40:

AGAAGCTTGG ATCCGTGTGA CAGTTTACTA AGTCCTC 37

(2) INFORMATION FOR SEQ ID NO: 41:

(i) SEQUENCE CHARACTERISTICS:
(A) LENGTH: 23 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 41:

AATTGGGACC CCGGATGCGG CAG 23

(2) INFORMATION FOR SEQ ID NO: 42:

(i) SEQUENCE CHARACTERISTICS:
(A) LENGTH: 9 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "primer"

(iii) HYPOTHETICAL: NO (xi) SEQUENCE DESCRIPTION: SEQ ID NO: 42:

CCCGTCGAC 9

(2) INFORMATION FOR SEQ ID NO: 43:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligomer"

-continued (iii) HYPOTHETICAL: NO (xi) SEQUENCE DESCRIPTION: SEQ ID NO: 43:

CCTGAACAGA TTATTGTTCA TGCT 24

(2) INFORMATION FOR SEQ ID NO: 44:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligomer"

(iii) HYPOTHETICAL: NO (xi) SEQUENCE DESCRIPTION: SEQ ID NO: 44:

GTGAATTTGG ATACATGAGC A 21

(2) INFORMATION FOR SEQ ID NO: 45:

(i) SEQUENCE CHARACTERISTICS:
(A) LENGTH: 169 amino acids
(B) TYPE: amino acid
(C) STRANDEDNESS: <Unknown>
(D) TOPOLOGY: linear (ii) MOLECULE TYPE: protein (iii) HYPOTHETICAL: YES (v) FRAGMENT TYPE: <Unknown>

(vi) ORIGINAL SOURCE:
(A) ORGANISM: Mus musculus (xi) SEQUENCE DESCRIPTION: SEQ ID NO: 45:

```
Val Gly Lys Tyr Thr Pro Glu Glu Ile Glu Lys Leu Lys Glu Leu Arg
  1               5                  10                  15

Ile Lys His Gly Asn Asp Trp Ala Thr Ile Gly Ala Ala Leu Gly Arg
             20                  25                  30

Ser Ala Ser Ser Val Lys Asp Arg Cys Arg Leu Met Lys Asp Thr Cys
         35                  40                  45

Asn Thr Gly Lys Trp Thr Glu Glu Glu Glu Lys Arg Leu Ala Glu Val
     50                  55                  60

Val His Glu Leu Thr Ser Thr Glu Pro Gly Asp Ile Val Thr Gln Gly
 65                  70                  75                  80

Val Ser Trp Ala Ala Val Ala Glu Arg Val Gly Thr Arg Ser Glu Lys
                 85                  90                  95

Gln Cys Arg Ser Lys Trp Leu Asn Tyr Leu Asn Trp Lys Gln Ser Gly
            100                 105                 110

Gly Thr Glu Trp Thr Lys Glu Asp Glu Ile Asn Leu Ile Leu Arg Ile
        115                 120                 125

Ala Glu Leu Asp Val Ala Asp Glu Asn Asp Ile Asn Trp Asp Leu Leu
    130                 135                 140

Ala Glu Gly Trp Ser Ser Val Arg Ser Pro Gln Trp Leu Arg Ser Lys
145                 150                 155                 160

Trp Trp Thr Ile Lys Arg Gln Ile Ala
                165
```

(2) INFORMATION FOR SEQ ID NO: 46:

-continued

```
      (i) SEQUENCE CHARACTERISTICS:
           (A) LENGTH: 156 amino acids
           (B) TYPE: amino acid
           (C) STRANDEDNESS: <Unknown>
           (D) TOPOLOGY: linear

     (ii) MOLECULE TYPE: protein

    (iii) HYPOTHETICAL: YES

      (v) FRAGMENT TYPE: <Unknown>

     (vi) ORIGINAL SOURCE:
           (A) ORGANISM: Gallus gallus

     (xi) SEQUENCE DESCRIPTION: SEQ ID NO: 46:

Leu Gly Lys Thr Arg Trp Thr Arg Glu Glu Asp Glu Lys Leu Lys Lys
  1               5                  10                  15

Leu Val Glu Gln Asn Gly Thr Glu Asp Trp Lys Val Ile Ala Ser Phe
             20                  25                  30

Leu Pro Asn Arg Thr Asp Val Gln Cys Gln His Arg Trp Gln Lys Val
         35                  40                  45

Leu Asn Pro Glu Leu Ile Lys Gly Pro Trp Thr Lys Glu Glu Asp Gln
     50                  55                  60

Arg Val Ile Glu Leu Val Gln Lys Tyr Gly Pro Lys Arg Trp Ser Val
 65                  70                  75                  80

Ile Ala Lys His Leu Lys Gly Arg Ile Gly Lys Gln Cys Arg Glu Arg
                 85                  90                  95

Trp His Asn His Leu Asn Pro Glu Val Lys Lys Thr Ser Trp Thr Glu
            100                 105                 110

Glu Glu Asp Arg Ile Ile Tyr Gln Ala His Lys Arg Leu Gly Asn Arg
        115                 120                 125

Trp Ala Glu Ile Ala Lys Leu Leu Pro Gly Arg Thr Asp Asn Ala Ile
    130                 135                 140

Lys Asn His Trp Asn Ser Thr Met Arg Arg Lys Val
145                 150                 155
```